United States Patent
Singh et al.

(10) Patent No.: US 8,846,908 B2
(45) Date of Patent: Sep. 30, 2014

(54) TRICYCLIC CARBAMATE JAK INHIBITORS

(75) Inventors: Rajinder Singh, Belmont, CA (US); Somasekhar Bhamidipati, Foster City, CA (US); Vadim Markovtsov, San Mateo, CA (US)

(73) Assignee: Rigel Pharmaceuticals, Inc., South San Francisco, CA (US)

( * ) Notice: Subject to any disclaimer, the term of this patent is extended or adjusted under 35 U.S.C. 154(b) by 599 days.

(21) Appl. No.: 13/119,950

(22) PCT Filed: Sep. 23, 2009

(86) PCT No.: PCT/US2009/057972
§ 371 (c)(1),
(2), (4) Date: Jun. 10, 2011

(87) PCT Pub. No.: WO2010/039518
PCT Pub. Date: Apr. 8, 2010

(65) Prior Publication Data
US 2011/0269749 A1     Nov. 3, 2011

Related U.S. Application Data

(60) Provisional application No. 61/099,507, filed on Sep. 23, 2008.

(51) Int. Cl.
| | |
|---|---|
| *C07D 239/48* | (2006.01) |
| *C07D 265/36* | (2006.01) |
| *C07D 263/62* | (2006.01) |
| *C07D 413/14* | (2006.01) |
| *A61K 31/506* | (2006.01) |
| *A61K 31/538* | (2006.01) |
| *A61K 31/5383* | (2006.01) |
| *A61K 31/423* | (2006.01) |
| *A61P 35/00* | (2006.01) |
| *C07D 413/12* | (2006.01) |

(52) U.S. Cl.
CPC ............ *C07D 413/14* (2013.01); *A61K 31/538* (2013.01); *A61K 31/423* (2013.01); *C07D 265/36* (2013.01); *A61K 31/506* (2013.01); *C07D 263/62* (2013.01); *A61K 31/5383* (2013.01); *C07D 239/48* (2013.01); *C07D 413/12* (2013.01)
USPC ......... 544/101; 544/324; 514/229.8; 514/275

(58) Field of Classification Search
CPC .. C07D 239/48; C07D 263/62; C07D 265/36; C07D 413/14; A61K 31/506; A61K 31/423; A61K 31/538; A61K 31/5383
USPC ....................... 544/101, 324; 514/275, 229.8
See application file for complete search history.

(56) References Cited

U.S. PATENT DOCUMENTS 7,332,484 B2    2/2008   Singh et al.
2006/0270694 A1   11/2006   Wong

OTHER PUBLICATIONS

Verstovsek S., American Society of Hematology, 636-642, 2009.*
Cornejo et al., Int J Biochem Cell Biol. 41(12): 2376-2379, 2009.*
Mass, R. D., Int. J. Radiation Oncology Bio. Phys.vol. 58(3): 932-940, 2004.*
Fabbro et al. Pharmacology & therapeutics 93, 79-98, 2002.*
Cohen et al., Current Opinion in Chemical Biology, 3,459-465, 1999.*
Freshney et al.,Culture of Animal Cells, A Manual of Basic Technique, Alan R. Liss, Inc., 1983, New York, p. 4.*
Dermer et al., Bio/Technology, 1994, 12:320.*
Golub et al., Science, 286, 531-537, 1999.*
Cecil Textbook of Medicine, edited by Bennet, J.C., and Plum F., 20th edition,vol. 1, 1004-101 O, 1996.*
Vos, J.D., et al., 'JAK2 tyrosine kinase inhibitor tyrphost in AG490 downregulates the mitogen-activated protein kinase and signal transducer and activator of transcription pathways and induces apoptosis in myeloma cells', British Journal of Haematology, 2000, vol. 109, pp. 823-828 (6 pgs).
Wernig, G., et al., 'Efficacy of TG101348, a selective JAK2 Inhibitor, in Treatment of a Murine Model of JAK2V617F-Induced Polycythemia Vera', Cancer Cell, Apr. 8, 2008, vol. 13, No. 4, pp. 311-320 (10 pgs).

* cited by examiner

*Primary Examiner* — Venkataraman Balasubramanian
(74) *Attorney, Agent, or Firm* — Travis Young; Klarquist Sparkman, LLP

(57) ABSTRACT

The present disclosure relates to 2,4-pyrimidinediamines substituted with tricyclic carbamates and the compositions and methods using these compounds in the treatment of conditions in which modulation of the JAK pathway or inhibition of JAK kinases, such as JAK2 or JAK3, is therapeutically useful.

24 Claims, No Drawings

TRICYCLIC CARBAMATE JAK INHIBITORS

CROSS REFERENCE TO RELATED APPLICATIONS

This application is a national stage filing under 35 U.S.C. 371 of International Application PCT/US2009/057972, filed Sep. 23, 2009, which claims the benefit of U.S. provisional patent application No. 61/099,507, filed Sep. 23, 2008. The entire teachings of the referenced applications are incorporated herein by reference. International Application PCT/US2009/057972 was published under PCT Article 21(2) in English.

INTRODUCTION

1. Field

The present disclosure concerns compounds, pharmaceutically acceptable salts thereof and pharmaceutical compositions comprising the compounds or salts. The compounds are useful as modulators of the JAK pathway or as inhibitors of JAK kinases, particularly JAK2, JAK3 or both.

2. Background

Protein kinases constitute a large family of structurally related enzymes that are responsible for the control of a variety of signal transduction processes within cells (see, e.g., Hardie and Hanks, *The Protein Kinase Facts Book*, I and II, Academic Press, San Diego, Calif., 1995). Protein kinases are thought to have evolved from a common ancestral gene due to the conservation of their structure and catalytic function. Almost all kinases contain a similar 250-300 amino acid catalytic domain. The kinases can be categorized into families by the substrates they phosphorylate (e.g., protein-tyrosine, protein-serine/threonine, lipids, etc.). Sequence motifs have been identified that generally correspond to each of these families (see, e.g., Hanks & Hunter, (1995), *FASEB J.* 9:576-596; Knighton et al., (1991), *Science* 253:407-414; Hiles et al., (1992), *Cell* 70:419-429; Kunz et al., (1993), *Cell* 73:585-596; Garcia-Bustos et al., (1994), *EMBO J.* 13:2352-2361).

JAK kinases (JAnus Kinases) are a family of cytoplasmic protein tyrosine kinases including JAK1, JAK2, JAK3 and TYK2. Each of the JAK kinases is selective for the receptors of certain cytokines, though multiple JAK kinases can be affected by particular cytokine or signaling pathways. Studies suggest that JAK3 associates with the common gamma (γc) chain of the various cytokine receptors. JAK3 in particular selectively binds to receptors and is part of the cytokine signaling pathway for IL-2, IL-4, IL-7, IL-9, IL-15 and IL-21. JAK1 interacts with, among others, the receptors for cytokines IL-2, IL-4, IL-7, IL-9 and IL-21, while JAK2 interacts with, among others, the receptors for IL-9 and TNF-α. Upon the binding of certain cytokines to their receptors (e.g., IL-2, IL-4, IL-7, IL-9, IL-15 and IL-21), receptor oligomerization occurs, resulting in the cytoplasmic tails of associated JAK kinases being brought into proximity and facilitating the trans-phosphorylation of tyrosine residues on the JAK kinase. This trans-phosphorylation results in the activation of the JAK kinase.

Phosphorylated JAK kinases bind various STAT (Signal Transducer and Activator of Transcription) proteins. STAT proteins, which are DNA binding proteins activated by phosphorylation of tyrosine residues, function both as signaling molecules and transcription factors and ultimately bind to specific DNA sequences present in the promoters of cytokine-responsive genes (Leonard et al., (2000), *J. Allergy Clin. Immunol.* 105:877-888). JAK/STAT signaling has been implicated in the mediation of many abnormal immune responses such as allergies, asthma, autoimmune diseases such as transplant (allograft) rejection, rheumatoid arthritis, amyotrophic lateral sclerosis and multiple sclerosis, as well as in solid and hematologic malignancies such as leukemia and lymphomas. For a review of the pharmaceutical intervention of the JAK/STAT pathway see Frank, (1999), *Mol. Med.* 5:432:456 and Seidel et al., (2000), *Oncogene* 19:2645-2656.

In view of the numerous conditions that are contemplated to benefit by treatment involving modulation of the JAK pathway it is immediately apparent that new compounds that modulate JAK pathways and methods of using these compounds should provide substantial therapeutic benefits to a wide variety of patients.

SUMMARY OF THE INVENTION

This invention is directed to 2,4-pyrimidinediamines substituted at N2 with tricyclic carbamates, tautomers, N-oxides, salts thereof, and methods of using these in the treatment of conditions in which modulation of the JAK pathway or inhibition of JAK kinases, particularly JAK2, will be therapeutically useful.

In one embodiment, the present disclosure embraces compounds of formula I:

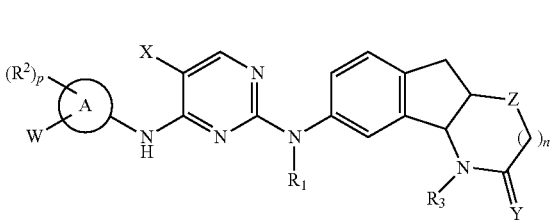

as well as tautomers, N-oxides, and salts thereof, wherein:
  ring A is aryl or heteroaryl;
  n is 0 or 1;
  p is 0, 1, 2 or 3 when ring A is monocyclic aryl or heteroaryl or p is 0, 1, 2, 3, 4, or 5 when ring A is bicyclic or tricyclic aryl or heteroaryl;
  X is selected from the group consisting of alkyl, substituted alkyl, hydroxy, alkoxy, substituted alkoxy, amino, substituted amino, carboxyl, carboxyl ester, cyano, halo, nitro, alkenyl, substituted alkenyl, alkynyl, and substituted alkynyl;
  Y is O or S;
  Z is O, S, or NH;
  W is hydrogen, —$SO_2N(R^4)R^5$, -alk-$SO_2N(R^4)R^5$, —$N(R^4)SO_2R^5$, or -alk-$N(R^4)SO_2R^5$;
  -alk- is selected from the group consisting of straight or branched chain $C_{1-6}$ alkylene group, and straight or branched chain substituted $C_{1-6}$ alkylene group;
  $R^1$ is hydrogen or $C_{1-3}$ alkyl;
  each $R^2$ independently is selected from the group consisting of alkyl, substituted alkyl, alkoxy, substituted alkoxy, alkenyl, substituted alkenyl, alkynyl, substituted alkynyl, cycloalkenyl, substituted cycloalkenyl, alkynyloxy, amino, substituted amino, aryl, substituted aryl, aryloxy, substituted aryloxy, cyano, cycloalkyl, substituted cycloalkyl, cycloalkoxy, substituted cycloalkoxy, heteroaryl, substituted heteroaryl, heteroaryloxy, substituted heteroaryloxy, heterocyclic, substituted heterocyclic, heterocyclyloxy, substituted heterocyclyloxy, aminocarbonyl, aminocarbonyloxy, carboxyl, carboxyl ester, (carboxyl ester)oxy, nitro, halo, and oxo, wherein if $R^2$ is oxo, then the oxo substituent is attached to a nonaromatic portion of ring A; or $R^3$ is hydrogen or $C_{1-3}$ alkyl;

$R^4$ is selected from the group consisting of hydrogen, alkyl, substituted alkyl, cycloalkyl, substituted cycloalkyl, heterocyclic, substituted heterocyclic, aryl, substituted aryl, heteroaryl, substituted heteroaryl, acyl and $M^+$, wherein $M^+$ is a counterion selected from the group consisting of $K^+$, $Na^+$, $Li^+$ and $^+N(R^8)_4$, wherein each $R^8$ is independently hydrogen or alkyl, and the nitrogen of $-SO_2N(R^4)R^5$ or $-N(R^4)SO_2R^5$ is $N^-$; and $R^5$ is selected from the group consisting of hydrogen, alkyl, substituted alkyl, amino, alkylamino, dialkylamino, cycloalkylamino, cycloalkyl, substituted cycloalkyl, heterocyclic, substituted heterocyclic, aryl, substituted aryl, heteroaryl, substituted heteroaryl, and acyl; or $R^4$ and $R^5$ together with the intervening atom or atoms to which they are bound form a heterocyclic or a substituted heterocyclic group.

Particular examples of disclosed compounds include, without limitation, those selected from the group consisting of:

In another embodiment, disclosed is a method of inhibiting an activity of a JAK kinase, comprising contacting the JAK kinase with an amount of a compound of this invention effective to inhibit an activity of the JAK kinase.

In another embodiment, this invention provides a method of inhibiting an activity of a JAK kinase, comprising contacting in vitro a JAK kinase, such as JAK2 or JAK3, with an amount of a compound of this invention to inhibit an activity of the JAK kinase.

In another embodiment, this invention provides a method of treating a disease or condition associated with JAK activity in a subject, wherein the method comprises administering to the subject a therapeutically effective amount of a compound of this invention.

It will be appreciated by one of skill in the art that the embodiments summarized above may be used together in any suitable combination to generate embodiments not expressly recited above and that such embodiments are considered to be part of the present invention.

DETAILED DESCRIPTION

Overview

The present disclosure relates, in part, to 2,4-pyrimidinediamines substituted at N2 with tricyclic carbamates and the compositions and methods using these compounds in the treatment of conditions in which modulation of the JAK pathway or inhibition of JAK kinases is therapeutically useful.

Definitions

As used herein, the following definitions shall apply unless otherwise indicated.

"Alkyl" refers to monovalent saturated aliphatic hydrocarbyl groups having from 1 to 10 carbon atoms and preferably 1 to 6 carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3$)$_2$CH—), n-butyl ($CH_3CH_2CH_2CH_2$—), isobutyl (($CH_3$)$_2$CHCH$_2$—), sec-butyl (($CH_3$)($CH_3CH_2$)CH—), t-butyl (($CH_3$)$_3$C—), n-pentyl ($CH_3CH_2CH_2CH_2CH_2$—), and neopentyl (($CH_3$)$_3$CCH$_2$—). Also by way of example, a methyl group, an ethyl group, an n-propyl and an isopropyl group are all represented by the term $C_{1-3}$ alkyl. Likewise terms indicating larger numerical ranges of carbon atoms are representative of any linear or branched hydrocarbyl falling within the numerical range. This inclusiveness applies to other hydrocarbyl terms bearing such numerical ranges.

"Alkylene" refers to divalent saturated aliphatic hydrocarbyl groups preferably having from 1 to 6 and more preferably 1 to 3 carbon atoms that are either straight-chained or branched. This term is exemplified by groups such as methylene (—$CH_2$—), ethylene (—$CH_2CH_2$—), n-propylene (—$CH_2CH_2CH_2$—), iso-propylene (—$CH_2CH(CH_3)$—) or (—$CH(CH_3)CH_2$—), and the like.

"Substituted alkylene" refers to an alkylene group having from 1 to 3 hydrogens replaced with substituents as described for carbons in the definition of "substituted" below.

"Alkoxy" refers to the group —O-alkyl, wherein alkyl is as defined herein. Alkoxy includes, by way of example, methoxy, ethoxy, n-propoxy, isopropoxy, n-butoxy, t-butoxy, sec-butoxy, n-pentoxy, and the like.

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, cycloalkenyl-C(O)—, substituted cycloalkenyl-C(O)—, aryl-C(O)—, substituted aryl-C(O)—, heteroaryl-C(O)—, substituted heteroaryl-C(O)—, heterocyclic-C(O)—, and substituted heterocyclic-C(O)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. By way of example, "acyl" includes the "acetyl" group $CH_3C(O)$—.

"Amino" refers to the group —$NH_2$.

"Substituted amino" refers to —$NR^{21}R^{22}$, wherein $R^{21}$ and $R^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{21}$ and $R^{22}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminocarbonyl" refers to the group —$C(O)NR^{21}R^{22}$, wherein $R^{21}$ and $R^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{21}$ and $R^{22}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminocarbonyloxy" refers to the group —O—C(O)$NR^{21}R^{22}$, wherein $R^{21}$ and $R^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{21}$ and $R^{22}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aryl" or "Ar" refers to a monovalent aromatic carbocyclic group of from 6 to 15 carbon atoms having a single ring (e.g., phenyl) or multiple condensed rings (e.g., naphthyl or anthryl) which condensed rings may or may not be aromatic (e.g., 2-benzoxazolinone, 2H-1,4-benzoxazin-3(4H)-one-7-yl, 9,10-dihydrophenanthrene, and the like), provided that the point of attachment is through an atom of the aromatic aryl group. Preferred aryl groups include phenyl and naphthyl.

"Aryloxy" refers to the group —O-aryl, wherein aryl is as defined herein, including, by way of example, phenoxy, naphthoxy, and the like.

"Alkenyl" refers to straight chain or branched hydrocarbyl groups having from 2 to 6 carbon atoms and preferably 2 to 4 carbon atoms and having at least 1 and preferably from 1 to 2 sites of double bond unsaturation. Such groups are exemplified, for example, bi-vinyl, allyl, and but-3-en-1-yl. Included within this term are the cis and trans isomers or mixtures of these omers.

"Alkynyl" refers to straight or branched monovalent hydrocarbyl groups having from 2 to 6 carbon atoms and preferably 2 to 3 carbon atoms and having at least 1 and preferably from 1 to 2 sites of triple bond unsaturation. Examples of such alkynyl groups include acetylenyl (—C≡CH), and propargyl (—CH$_2$C≡CH).

"Alkynyloxy" refers to the group —O-alkynyl, wherein alkynyl is as defined herein. Alkynyloxy includes, by way of example, ethynyloxy, propynyloxy, and the like.

"Carboxyl," "carboxy" or "carboxylate" refers to —CO$_2$H or salts thereof.

"Carboxyl ester" or "carboxy ester" refers to the groups —C(O)O-alkyl, —C(O)O-substituted alkyl, —C(O)O-alkenyl, —C(O)O-substituted alkenyl, —C(O)O-alkynyl, —C(O)O-substituted alkynyl, —C(O)O-aryl, —C(O)O-substituted aryl, —C(O)O-cycloalkyl, —C(O)O-substituted cycloalkyl, —C(O)O-cycloalkenyl, —C(O)O-substituted cycloalkenyl, —C(O)O-heteroaryl, —C(O)O-substituted heteroaryl, —C(O)O-heterocyclic, and —C(O)O-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"(Carboxyl ester)oxy" or "carbonate" refers to the groups —O—C(O)O-alkyl, —O—C(O)O-substituted alkyl, —O—C(O)O-alkenyl, —O—C(O)O-substituted alkenyl, —O—C(O)O-alkynyl, —O—C(O)O-substituted alkynyl, —O—C(O)O-aryl, —O—C(O)O-substituted aryl, —O—C(O)O-cycloalkyl, —O—C(O)O-substituted cycloalkyl, —O—C(O)O-cycloalkenyl, —O—C(O)O-substituted cycloalkenyl, —O—C(O)O-heteroaryl, —O—C(O)O-substituted heteroaryl, —O—C(O)O-heterocyclic, and —O—C(O)O-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Cyano" or "nitrile" refers to the group —CN.

"Cycloalkyl" refers to cyclic alkyl groups of from 3 to 10 carbon atoms having single or multiple cyclic rings including fused, bridged, and spiro ring systems. Examples of suitable cycloalkyl groups include, for instance, adamantyl, cyclopropyl, cyclobutyl, cyclopentyl, cyclooctyl and the like.

"Cycloalkylalkyl" refers to a cycloalkyl-alkylene group, for example cyclopropyl-CH$_2$— where the cycloalkyl is bonded to the parent structure via an alkylene divalent linking group.

"Cycloalkenyl" refers to non-aromatic cyclic alkyl groups of from 3 to 10 carbon atoms having single or multiple rings and having at least one double bond and preferably from 1 to 2 double bonds.

"Cycloalkoxy" refers to —O-cycloalkyl.

"Halo" or "halogen" refers to fluoro, chloro, bromo, and iodo and is preferably fluoro or chloro.

"Hydroxy" or "hydroxyl" refers to the group —OH.

"Heteroaryl" refers to an aromatic group of from 1 to 10 carbon atoms and 1 to 4 heteroatoms selected from the group consisting of oxygen, nitrogen, and sulfur within the ring. Such heteroaryl groups can have a single ring (e.g., pyridinyl, imidazolyl or furyl) or multiple condensed rings (e.g., indolizinyl, quinolinyl, benzimidazolyl or benzothienyl), wherein the condensed rings may or may not be aromatic and/or contain a heteroatom, provided that the point of attachment is through an atom of the aromatic heteroaryl group. In one embodiment, the nitrogen and/or sulfur ring atom(s) of the heteroaryl group are optionally oxidized to provide for the N-oxide (N→O), sulfinyl, or sulfonyl moieties. Preferred heteroaryls include pyridinyl, pyrrolyl, indolyl, thiophenyl, and furanyl.

"Heteroaryloxy" refers to —O-heteroaryl.

"Heterocycle," "heterocyclic," "heterocycloalkyl," and "heterocyclyl" refer to a saturated or unsaturated group having a single ring or multiple condensed rings, including fused bridged and spiro ring systems, and having from 3 to 15 ring atoms, including 1 to 4 hetero atoms. These ring atoms are selected from the group consisting of nitrogen, sulfur, or oxygen, wherein, in fused ring systems, one or more of the rings can be cycloalkyl, aryl, or heteroaryl, provided that the point of attachment is through the non-aromatic ring. In one embodiment, the nitrogen and/or sulfur atom(s) of the heterocyclic group are optionally oxidized to provide for the N-oxide, —S(O)—, or —SO$_2$— moieties.

"Heterocycloalkylalkyl" refers to a heterocyclyl group linked to the parent structure via an alkylene linker, for example (tetrahydrofuran-3-yl)methyl-:

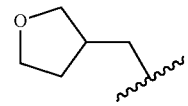

Examples of heterocycle and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, tetrahydrofuranyl, and the like.

"Heterocyclyloxy" refers to the group —O-heterocycyl.

"Nitro" refers to the group —$NO_2$.

"Oxo" refers to the atom (=O).

"Oxy radical" refers to —O. (also designated as →O), that is, a single bond oxygen radical. By way of example, N-oxides are nitrogens with an oxy radical. A specific example is where $R^{2a}$, $R^{2b}$, $R^{4a}$ and $R^{4b}$ are methyl, n is 1 and $R^3$ is oxy radical, that is, where the ring bearing $R^{2a}$, $R^{2b}$, $R^{4a}$, $R^{4b}$ and $R^3$ is 2,2,6,6-tetramethylpiperidin-N-oxide (commonly known as TEMPO).

Unless indicated otherwise, the nomenclature of substituents that are not explicitly defined herein are arrived at by naming the terminal portion of the functionality followed by the adjacent functionality toward the point of attachment. For example, the substituent "arylalkyloxycarbonyl" refers to the group (aryl)-(alkyl)-O—C(O)—.

The term "substituted," when used to modify a specified group or radical, means that one or more hydrogen atoms of the specified group or radical are each, independently of one another, replaced with the same or different substituent groups as defined below. By way of example, a pyrrolidinyl group on a compound of the invention can be substituted or unsubstituted. A specific example of a substituted pyrrolidine is where $R^{2a}$, $R^{2b}$ are methyl, $R^3$, $R^{4a}$ and $R^{4b}$ are H, and n is 0, that is, where the ring bearing $R^{2a}$, $R^{2b}$, $R^3$, $R^{4a}$ and $R^{4b}$ is 2,2-dimethylpyrrolidinyl.

Substituent groups for substituting for one or more hydrogens (any two hydrogens on a single carbon can be replaced with =O, =$NR^{70}$, =N—$OR^{70}$, =$N_2$ or =S) on saturated carbon atoms in the specified group or radical are, unless otherwise specified, —$R^{60}$, halo, =O, —$OR^{70}$, —$SR^{70}$, —$NR^{80}R^{80}$, trihalomethyl, —CN, —OCN, —SCN, —NO, —$NO_2$, =$N_2$, —$N_3$, —$SO_2R^{70}$, —$SO_2^-M^+$, —$SO_2OR^{70}$, —$OSO_2R^{70}$, —$OSO_2O\ M^+$, —$OSO_2OR^{70}$, —P(O)(O)$_2$ $(M^+)_2$, —P(O)($OR^{70}$)O $M^+$, —P(O)($OR^{70}$)$_2$, —C(O)$R^{70}$, —C(S)$R^{70}$, —C($NR^{70}$)$R^{70}$, —C(O)O$^-M^+$, —C(O)$OR^{70}$, —C(S)$OR^{70}$, —C(O)$NR^{80}R^{80}$, —C($NR^{70}$)$NR^{80}R^{80}$, —OC(O)$R^{70}$, —OC(S)$R^{70}$, —OC(O)O$^-M^+$, —OC(O)$OR^{70}$, —OC(S)$OR^{70}$, —$NR^{70}$C(O)$R^{70}$, —$NR^{70}$C(S)$R^{70}$, —$NR^{70}$$CO_2^-M^+$, —$NR^{70}$$CO_2R^{70}$, —$NR^{70}$C(S)$OR^{70}$, —$NR^{70}$C(O)$NR^{80}R^{80}$, —$NR^{70}$C($NR^{70}$)$R^{70}$ and —$NR^{70}$C($NR^{70}$)$NR^{80}R^{80}$, where $R^{60}$ is selected from the group consisting of optionally substituted alkyl, cycloalkyl, heteroalkyl, heterocycloalkylalkyl, cycloalkylalkyl, aryl, arylalkyl, heteroaryl and heteroarylalkyl, each $R^{70}$ is independently hydrogen or $R^{60}$; each $R^{80}$ is independently $R^{70}$ or alternatively, two $R^{80}$'s, taken together with the nitrogen atom to which they are bonded, form a 5-, 6- or 7-membered heterocycloalkyl which may optionally include from 1 to 4 of the same or different additional heteroatoms selected from the group consisting of O, N and S, of which N may have —H or $C_1$-$C_3$ alkyl substitution; and each $M^+$ is a counter ion with a net single positive charge. Each $M^+$ may independently be, for example, an alkali ion, such as $K^+$, $Na^+$, $Li^+$; an ammonium ion, such as $^+N(R^{60})_4$; or an alkaline earth ion, such as $[Ca^{2+}]_{0.5}$, $[Mg^{2+}]_{0.5}$, or $[Ba^{2+}]_{0.5}$ ("subscript 0.5 means e.g. that one of the counter ions for such divalent alkali earth ions can be an ionized form of a compound of the invention and the other a typical counter ion such as chloride, or two ionized compounds of the invention can serve as counter ions for such divalent alkali earth ions, or a doubly ionized compound of the invention can serve as the counter ion for such divalent alkali earth ions). As specific examples, —$NR^{80}R^{80}$ is meant to include —$NH_2$, —NH-alkyl, N-pyrrolidinyl, N-piperazinyl, 4N-methyl-piperazin-1-yl and N-morpholinyl.

Substituent groups for hydrogens on unsaturated carbon atoms in "substituted" alkene, cycloalkene, alkyne, aryl and heteroaryl groups are, unless otherwise specified, —$R^{60}$, halo, —$O^-M^+$, —$OR^{70}$, —$SR^{70}$, —$S^-M^+$, —$NR^{80}R^{80}$, trihalomethyl, —$CF_3$, —CN, —OCN, —SCN, —NO, —$NO_2$, —$N_3$, —$SO_2R^{70}$, —$SO_3^-M^+$, —$SO_3R^{70}$, —$OSO_2R^{70}$, —$OSO_3^-M^+$, —$OSO_3R^{70}$, —$PO_3^{-2}(M^+)_2$, —P(O)($OR^{70}$)$O^-M^+$, —P(O)($OR^{70}$)$_2$, —C(O)$R^{70}$, —C(S)$R^{70}$, —C($NR^{70}$)$R^{70}$, —$CO_2^-M^+$, —$CO_2R^{70}$ —C(S)$OR^{70}$, —C(O)$NR^{80}R^{80}$, —C($NR^{70}$)$NR^{80}R^{80}$, —OC(O)$R^{70}$, —OC(S)$R^{70}$, —$OCO_2^-M^+$, —$OCO_2R^{70}$, —OC(S)$OR^{70}$, —$NR^{70}$C(O)$R^{70}$, —$NR^{70}$C(S)$R^{70}$, —$NR^{70}$$CO_2^-M^+$, —$NR^{70}$$CO_2R^{70}$, —$NR^{70}$C(S)$OR^{70}$, —$NR^{70}$C(O)$NR^{80}R^{80}$, —$NR^{70}$C($NR^{70}$)$R^{70}$ and —$NR^{70}$C($NR^{70}$)$NR^{80}R^{80}$, where $R^{60}$, $R^{70}$, $R^{80}$ and $M^+$ are as previously defined, provided that in case of substituted alkene or alkyne, the substituents are not —$O^-M^+$, —$OR^{70}$, —$SR^{70}$, or —$S^-M^+$.

Substituent groups for replacing hydrogens on nitrogen atoms in"substituted" heterocyclic groups are, unless otherwise specified, —$R^{60}$, —$O^-M^+$, —$OR^{70}$, —$SR^{70}$, —$S^-M^+$, —$NR^{80}R^{80}$, trihalomethyl, —$CF_3$, —CN, —NO, —$NO_2$, —S(O)$_2R^{70}$, —S(O)$_2O^-M^+$, —S(O)$_2OR^{70}$, —OS(O)$_2R^{70}$, —OS(O)$_2O^-M^+$, OS(O)$_2OR^{70}$, —P(O)($O^-$)$_2(M^+)_2$, —P(O)($OR^{70}$)$O^-M^+$, —P(O)($OR^{70}$)($OR^{70}$), —C(O)$R^{70}$, —C(S)$R^{70}$, —C($NR^{70}$)$R^{70}$, —C(O)$OR^{70}$, —C(S)$OR^{70}$, —C(O)$NR^{80}R^{80}$, —C($NR^{70}$)$NR^{80}R^{80}$, —OC(O)$R^{70}$, —OC(S)$R^{70}$, —OC(O)$OR^{70}$, —OC(S)$OR^{70}$, —$NR^{70}$C(O)$R^{70}$, —$NR^{70}$C(S)$R^{70}$, —$NR^{70}$C(O)$OR^{70}$, —$NR^{70}$C(S)$OR^{70}$, —$NR^{70}$C(O)$NR^{80}R^{80}$, —$NR^{70}$C($NR^{70}$)$R^{70}$ and —$NR^{70}$C($NR^{70}$)$NR^{80}R^{80}$, where $R^{60}$, $R^{70}$, $R^{80}$ and $M^+$ are as previously defined.

In a preferred embodiment, a group that is substituted has 1, 2, 3, or 4 substituents, 1, 2, or 3 substituents, 1 or 2 substituents, or 1 substituent.

It is understood that in all substituted groups defined above, polymers arrived at by defining substituents with further substituents to themselves (e.g., substituted aryl having a substituted aryl group as a substituent which is itself substituted with a substituted aryl group, which is further substituted by a substituted aryl group, etc.) are not intended for inclusion herein. In such cases, the maximum number of such iterative substitutions is three. For example, serial substitutions of substituted aryl groups are limited to substituted aryl-(substituted aryl)-substituted aryl.

"Stereoisomer" and "stereoisomers" refer to compounds that have same atomic connectivity but different atomic arrangement in space. Stereoisomers include cis-trans isomers, E and Z isomers, enantiomers, and diastereomers. The compounds of the invention, or their pharmaceutically acceptable salts may contain one or more asymmetric centres and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, such as HPLC using a chiral column. When the compounds described herein contain olefinic double bonds or other centers of geometric asymmetry, and unless specified otherwise, it is intended that the compounds include both E and Z geometric isomers.

"Tautomer" refers to alternate forms of a molecule that differ only in electronic bonding of atoms and/or in the position of a proton, such as enol-keto and imine-enamine tautomers, or the tautomeric forms of heteroaryl groups containing a —N=C(H)—NH— ring atom arrangement, such as pyrazoles, imidazoles, benzimidazoles, triazoles, and tetrazoles. A person of ordinary skill in the art would recognize that other tautomeric ring atom arrangements are possible.

"Patient" or "Subject" refers to human and non-human animals, especially mammals.

"Pharmaceutically acceptable salt" refers to pharmaceutically acceptable salts of a compound, which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate, and the like.

"Pharmaceutically effective amount" and "therapeutically effective amount" refer to an amount of a compound sufficient to treat a specified disorder or disease or one or more of its symptoms and/or to prevent the occurrence of the disease or disorder. In reference to tumorigenic proliferative disorders, a pharmaceutically or therapeutically effective amount comprises an amount sufficient to, among other things, cause the tumor to shrink or decrease the growth rate of the tumor.

"Solvate" refers to a complex formed by combination of solvent molecules with molecules or ions of the solute. The solvent can be an organic compound, an inorganic compound, or a mixture of both. Some examples of solvents include, but are not limited to, methanol, N,N-dimethylformamide, tetrahydrofuran, dimethylsulfoxide, and water.

"Treating" or "treatment" as used herein covers the treatment of the disease or condition of interest in a mammal, preferably a human, having the disease or condition of interest, and includes:

(i) preventing the disease or condition from occurring in a mammal, in particular, when such mammal is predisposed to the condition but has not yet been diagnosed as having it;
(ii) inhibiting the disease or condition, i.e., arresting its development;
(iii) relieving the disease or condition, i.e., causing regression of the disease or condition; or
(iv) stabilizing the disease or condition.

As used herein, the terms "disease" and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

Unless indicated otherwise, the nomenclature of substituents that are not explicitly defined herein are arrived at by naming the terminal portion of the functionality followed by the adjacent functionality toward the point of attachment. For example, the substituent "arylalkyloxycarbonyl" refers to the group (aryl)-(alkyl)-O—C(O)—.

Similarly, it is understood that the above definitions are not intended to include impermissible substitution patterns (e.g., methyl substituted with 5 fluoro groups). Such impermissible substitution patterns are easily recognized by a person having ordinary skill in the art.

Compounds

This invention provides novel 2,4-pyrimidinediamines substituted at N2 with tricyclic carbamates, tautomers, N-oxides, salts thereof, methods of making the compounds, and methods of using these compounds in the treatment of conditions in which targeting of the JAK pathway or inhibition of JAK kinases, particularly JAK2, are therapeutically useful.

These conditions include, but are not limited to, debilitating and fatal diseases and disorders that affect both children and adults. Examples of these conditions include oncological diseases such as leukemia, including childhood leukemia and lymphoma; autoimmune conditions, such as transplant rejection; and the other conditions described herein. Given the severity of and suffering caused by these conditions, it is vital that new treatments are developed to treat these conditions.

In aspect, the present disclosure relates to a compound according to formula I:

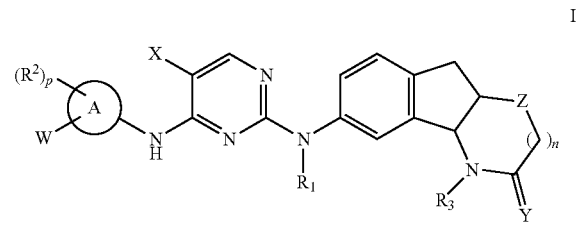

a tautomer, N-oxide, or salt thereof, wherein:
  ring A is aryl or heteroaryl;
  n is 0 or 1;
  p is 0, 1, 2 or 3 when ring A is monocyclic aryl or heteroaryl or p is 0, 1, 2, 3, 4, or 5 when ring A is bicyclic or tricyclic aryl or heteroaryl;
  X is selected from the group consisting of alkyl, substituted alkyl, hydroxy, alkoxy, substituted alkoxy, amino, substituted amino, carboxyl, carboxyl ester, cyano, halo, nitro, alkenyl, substituted alkenyl, alkynyl, and substituted alkynyl;
  Y is O or S;
  Z is O, S, or NH;
  W is hydrogen, —SO$_2$N(R$^4$)R$^5$, -alk-SO$_2$N(R$^4$)R$^5$, —N(R$^4$)SO$_2$R$^5$, or -alk-N(R$^4$)SO$_2$R$^5$;
  -alk- is selected from the group consisting of straight or branched chain C$_{1-6}$ alkylene group, and straight or branched chain substituted C$_{1-6}$ alkylene group;
  R$^1$ is hydrogen or C$_{1-3}$ alkyl;
  each R$^2$ independently is selected from the group consisting of alkyl, substituted alkyl, alkoxy, substituted alkoxy, alkenyl, substituted alkenyl, alkynyl, substituted alkynyl, cycloalkenyl, substituted cycloalkenyl, alkynyloxy, amino, substituted amino, aryl, substituted aryl, aryloxy, substituted aryloxy, cyano, cycloalkyl, substituted cycloalkyl, cycloalkoxy, substituted cycloalkoxy, heteroaryl, substituted heteroaryl, heteroaryloxy, substituted heteroaryloxy, heterocyclic, substituted heterocyclic, heterocyclyloxy, substituted heterocyclyloxy, aminocarbonyl, aminocarbonyloxy, carboxyl, carboxyl ester, (carboxyl ester)oxy, nitro, halo, and oxo, wherein if R$^2$ is oxo, then the oxo substituent is attached to a nonaromatic portion of ring A; or
  R$^3$ is hydrogen or C$_{1-3}$ alkyl;
  R$^4$ is selected from the group consisting of hydrogen, alkyl, substituted alkyl, cycloalkyl, substituted cycloalkyl, heterocyclic, substituted heterocyclic, aryl, substituted aryl, heteroaryl, substituted heteroaryl, acyl and M$^+$, wherein M$^+$ is a counterion selected from the group consisting of K$^+$, Na$^+$, Li$^+$ and $^+$N(R$^8$)$_4$, wherein each R$^8$ is independently hydrogen or alkyl, and the nitrogen of —SO$_2$N(R$^4$)R$^5$ or —N(R$^4$)SO$_2$R$^5$ is N$^-$; and
  R$^5$ is selected from the group consisting of hydrogen, alkyl, substituted alkyl, amino, alkylamino, dialkylamino, cycloalkylamino, cycloalkyl, substituted cycloalkyl, heterocyclic, substituted heterocyclic, aryl, substituted aryl, heteroaryl, substituted heteroaryl, and acyl; or $R^4$ and $R^5$ together with the intervening atom or atoms bound thereto form a heterocyclic or a substituted heterocyclic group.

In another embodiment, $R^1$ is hydrogen. In another embodiment, each of Z and Y is O and $R^3$ is hydrogen. In a further embodiment, W is hydrogen.

In another embodiment, this invention provides a compound according to formula IIa:

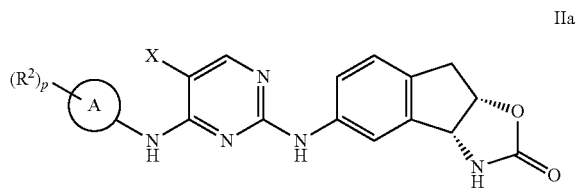

IIa a tautomer, N-oxide, or salt thereof, wherein:
 ring A is aryl or heteroaryl;
 p is 0, 1, 2 or 3 when ring A is monocyclic aryl or heteroaryl or p is 0, 1, 2, 3, 4, or 5 when ring A is bicyclic or tricyclic aryl or heteroaryl;
 X is selected from the group consisting of alkyl, substituted alkyl, hydroxy, alkoxy, substituted alkoxy, amino, substituted amino, carboxyl, carboxyl ester, cyano, halo, nitro, alkenyl, substituted alkenyl, alkynyl, and substituted alkynyl; and
 each $R^2$ independently is selected from the group consisting of alkyl, substituted alkyl, alkoxy, substituted alkoxy, alkenyl, substituted alkenyl, alkynyl, substituted alkynyl, cycloalkenyl, substituted cycloalkenyl, alkynyloxy, amino, substituted amino, aryl, substituted aryl, aryloxy, substituted aryloxy, cyano, cycloalkyl, substituted cycloalkyl, cycloalkoxy, substituted cycloalkoxy, heteroaryl, substituted heteroaryl, heteroaryloxy, substituted heteroaryloxy, heterocyclic, substituted heterocyclic, heterocyclyloxy, substituted heterocyclyloxy, aminocarbonyl, aminocarbonyloxy, carboxyl, carboxyl ester, (carboxyl ester)oxy, nitro, halo, and oxo, wherein if $R^2$ is oxo, then the oxo substituent is attached to a nonaromatic portion of ring A.

In another embodiment, this invention provides a compound according to formula IIb:

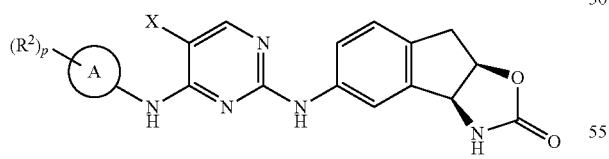

IIb a tautomer, N-oxide, or salt thereof, wherein:
 ring A is aryl or heteroaryl;
 p is 0, 1, 2 or 3 when ring A is monocyclic aryl or heteroaryl or p is 0, 1, 2, 3, 4, or 5 when ring A is bicyclic or tricyclic aryl or heteroaryl;
 X is selected from the group consisting of alkyl, substituted alkyl, hydroxy, alkoxy, substituted alkoxy, amino, substituted amino, carboxyl, carboxyl ester, cyano, halo, nitro, alkenyl, substituted alkenyl, alkynyl, and substituted alkynyl; and each $R^2$ independently is selected from the group consisting of alkyl, substituted alkyl, alkoxy, substituted alkoxy, alkenyl, substituted alkenyl, alkynyl, substituted alkynyl, cycloalkenyl, substituted cycloalkenyl, alkynyloxy, amino, substituted amino, aryl, substituted aryl, aryloxy, substituted aryloxy, cyano, cycloalkyl, substituted cycloalkyl, cycloalkoxy, substituted cycloalkoxy, heteroaryl, substituted heteroaryl, heteroaryloxy, substituted heteroaryloxy, heterocyclic, substituted heterocyclic, heterocyclyloxy, substituted heterocyclyloxy, aminocarbonyl, aminocarbonyloxy, carboxyl, carboxyl ester, (carboxyl ester)oxy, nitro, halo, and oxo, wherein if $R^2$ is oxo, then the oxo substituent is attached to a nonaromatic portion of ring A.

In another embodiment, this invention provides a compound according to formula IIa or IIB as described herein, wherein ring A is bicyclic heteroaryl. In another embodiment, X is alkyl or halo. In another embodiment, X is selected from the group consisting of methyl, chloro, and fluoro. In a further embodiment,

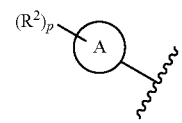

is:

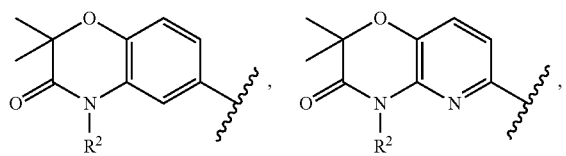

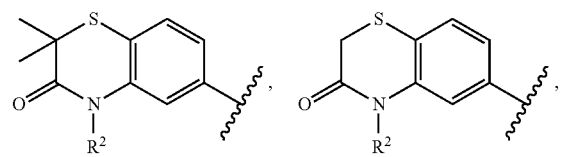

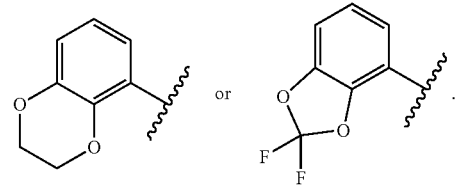

In another embodiment, this invention provides a compound according to formula IIa or IIa as described herein, wherein ring A is monocyclic or bicyclic aryl. In another embodiment, X is alkyl or halo. In another embodiment, X is selected from the group consisting of methyl, chloro, and fluoro. In a further embodiment,

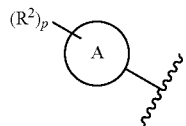

is:

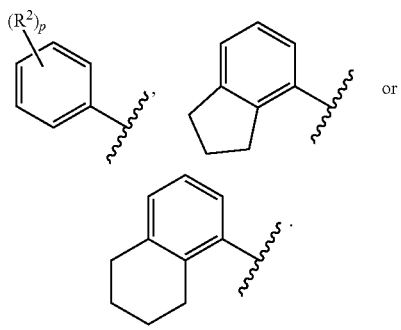

In another embodiment, this invention provides a compound according to formula IIIa:

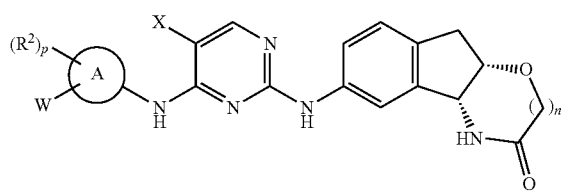

a tautomer, N-oxide, or salt thereof, wherein:
ring A is aryl or heteroaryl;
n is 0 or 1;
p is 0, 1, 2 or 3 when ring A is monocyclic aryl or heteroaryl or p is 0, 1, 2, 3, 4, or 5 when ring A is bicyclic or tricyclic aryl or heteroaryl;
X is selected from the group consisting of alkyl, substituted alkyl, hydroxy, alkoxy, substituted alkoxy, amino, substituted amino, carboxyl, carboxyl ester, cyano, halo, nitro, alkenyl, substituted alkenyl, alkynyl, and substituted alkynyl;
W is —SO$_2$N(R$^4$)R$^5$, -alk-SO$_2$N(R$^4$)R$^5$, —N(R$^4$)SO$_2$R$^5$, or -alk-N(R$^4$)SO$_2$R$^5$;
-alk- is selected from the group consisting of straight or branched chain C$_{1-6}$ alkylene group, and straight or branched chain substituted C$_{1-6}$ alkylene group;
each R$^2$ independently is selected from the group consisting of alkyl, substituted alkyl, alkoxy, substituted alkoxy, alkenyl, substituted alkenyl, alkynyl, substituted alkynyl, cycloalkenyl, substituted cycloalkenyl, alkynyloxy, amino, substituted amino, aryl, substituted aryl, aryloxy, substituted aryloxy, cyano, cycloalkyl, substituted cycloalkyl, cycloalkoxy, substituted cycloalkoxy, heteroaryl, substituted heteroaryl, heteroaryloxy, substituted heteroaryloxy, heterocyclic, substituted heterocyclic, heterocyclyloxy, substituted heterocyclyloxy, aminocarbonyl, aminocarbonyloxy, carboxyl, carboxyl ester, (carboxyl ester)oxy, nitro, halo, and oxo, wherein if R$^2$ is oxo, then the oxo substituent is attached to a nonaromatic portion of ring A; or
R$^4$ is selected from the group consisting of hydrogen, alkyl, substituted alkyl, cycloalkyl, substituted cycloalkyl, heterocyclic, substituted heterocyclic, aryl, substituted aryl, heteroaryl, substituted heteroaryl, acyl and M$^+$, wherein M$^+$ is a counterion selected from the group consisting of K$^+$, Na$^+$, Li$^+$ and $^+$N(R$^8$)$_4$, wherein each R$^8$ is independently hydrogen or alkyl, and the nitrogen of —SO$_2$N(R$^4$)R$^5$ or —N(R$^4$)SO$_2$R$^5$ is N$^-$; and
R$^5$ is selected from the group consisting of hydrogen, alkyl, substituted alkyl, amino, alkylamino, dialkylamino, cycloalkylamino, cycloalkyl, substituted cycloalkyl, heterocyclic, substituted heterocyclic, aryl, substituted aryl, heteroaryl, substituted heteroaryl, and acyl; or
R$^4$ and R$^5$ together with the intervening atom or atoms bound thereto form a heterocyclic or a substituted heterocyclic group.

In another embodiment, this invention provides a compound according to formula IIIb:

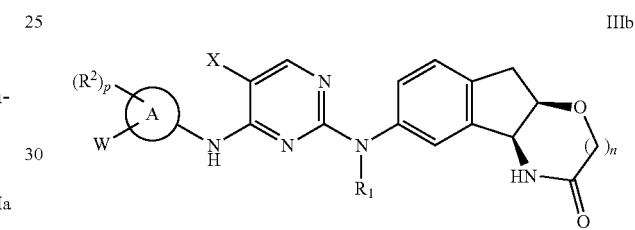

a tautomer, N-oxide, or salt thereof, wherein:
ring A is aryl or heteroaryl;
n is 0 or 1;
p is 0, 1, 2 or 3 when ring A is monocyclic aryl or heteroaryl or p is 0, 1, 2, 3, 4, or 5 when ring A is bicyclic or tricyclic aryl or heteroaryl;
X is selected from the group consisting of alkyl, substituted alkyl, hydroxy, alkoxy, substituted alkoxy, amino, substituted amino, carboxyl, carboxyl ester, cyano, halo, nitro, alkenyl, substituted alkenyl, alkynyl, and substituted alkynyl;
W is —SO$_2$N(R$^4$)R$^5$, -alk-SO$_2$N(R$^4$)R$^5$, —N(R$^4$)SO$_2$R$^5$, or -alk-N(R$^4$)SO$_2$R$^5$;
-alk- is selected from the group consisting of straight or branched chain C$_{1-6}$ alkylene group, and straight or branched chain substituted C$_{1-6}$ alkylene group;
each R$^2$ independently is selected from the group consisting of alkyl, substituted alkyl, alkoxy, substituted alkoxy, alkenyl, substituted alkenyl, alkynyl, substituted alkynyl, cycloalkenyl, substituted cycloalkenyl, alkynyloxy, amino, substituted amino, aryl, substituted aryl, aryloxy, substituted aryloxy, cyano, cycloalkyl, substituted cycloalkyl, cycloalkoxy, substituted cycloalkoxy, heteroaryl, substituted heteroaryl, heteroaryloxy, substituted heteroaryloxy, heterocyclic, substituted heterocyclic, heterocyclyloxy, substituted heterocyclyloxy, aminocarbonyl, aminocarbonyloxy, carboxyl, carboxyl ester, (carboxyl ester)oxy, nitro, halo, and oxo, wherein if R$^2$ is oxo, then the oxo substituent is attached to a nonaromatic portion of ring A; or
R$^4$ is selected from the group consisting of hydrogen, alkyl, substituted alkyl, cycloalkyl, substituted cycloalkyl, heterocyclic, substituted heterocyclic, aryl, substituted aryl, heteroaryl, substituted heteroaryl, acyl and M⁺, wherein M⁺ is a counterion selected from the group consisting of K⁺, Na⁺, Li⁺ and ⁺N(R⁸)₄, wherein each R⁸ is independently hydrogen or alkyl, and the nitrogen of —SO₂N(R⁴)R⁵ or —N(R⁴)SO₂R⁵ is N⁻; and R⁵ is selected from the group consisting of hydrogen, alkyl, substituted alkyl, amino, alkylamino, dialkylamino, cycloalkylamino, cycloalkyl, substituted cycloalkyl, heterocyclic, substituted heterocyclic, aryl, substituted aryl, heteroaryl, substituted heteroaryl, and acyl; or R⁴ and R⁵ together with the intervening atom or atoms bound thereto form a heterocyclic or a substituted heterocyclic group.

In another embodiment, this invention provides a compound according to formula IIIa or IIIB as described herein, wherein ring A is phenyl. In another embodiment, X is alkyl or halo. In another embodiment, X is methyl or chloro. In a further embodiment, W is -alk-N(R⁴)SO₂R⁵. In a preferred embodiment, alk is —CH₂— or —CH₂CH₂—. In a preferred embodiment, this invention provides a compound according to formula IVa:

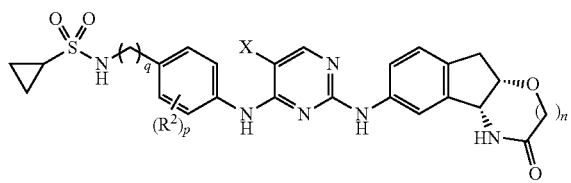

IVa a tautomer, N-oxide, or salt thereof, wherein:
n is 0 or 1;
p is 0, 1, 2 or 3;
q is 1 or 2;
X is alkyl or halo; and
each R² independently is selected from the group consisting of alkyl, substituted alkyl, alkoxy, substituted alkoxy, alkenyl, substituted alkenyl, alkynyl, substituted alkynyl, cycloalkenyl, substituted cycloalkenyl, alkynyloxy, amino, substituted amino, aryl, substituted aryl, aryloxy, substituted aryloxy, cyano, cycloalkyl, substituted cycloalkyl, cycloalkoxy, substituted cycloalkoxy, heteroaryl, substituted heteroaryl, heteroaryloxy, substituted heteroaryloxy, heterocyclic, substituted heterocyclic, heterocyclyloxy, substituted heterocyclyloxy, aminocarbonyl, aminocarbonyloxy, carboxyl, carboxyl ester, (carboxyl ester)oxy, nitro, halo, and oxo, wherein if R² is oxo, then the oxo substituent is attached to a nonaromatic portion of ring A.

In another preferred embodiment, this invention provides a compound according to formula IVb:

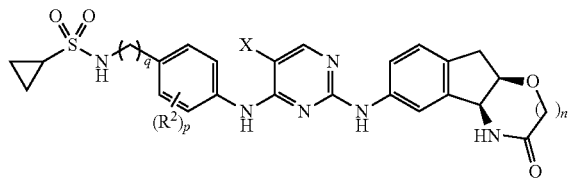

IVb a tautomer, N-oxide, or salt thereof, wherein:

n is 0 or 1;
p is 0, 1, 2 or 3;
q is 1 or 2;
X is alkyl or halo; and
each R² independently is selected from the group consisting of alkyl, substituted alkyl, alkoxy, substituted alkoxy, alkenyl, substituted alkenyl, alkynyl, substituted alkynyl, cycloalkenyl, substituted cycloalkenyl, alkynyloxy, amino, substituted amino, aryl, substituted aryl, aryloxy, substituted aryloxy, cyano, cycloalkyl, substituted cycloalkyl, cycloalkoxy, substituted cycloalkoxy, heteroaryl, substituted heteroaryl, heteroaryloxy, substituted heteroaryloxy, heterocyclic, substituted heterocyclic, heterocyclyloxy, substituted heterocyclyloxy, aminocarbonyl, aminocarbonyloxy, carboxyl, carboxyl ester, (carboxyl ester)oxy, nitro, halo, and oxo, wherein if R² is oxo, then the oxo substituent is attached to a nonaromatic portion of ring A.

In another embodiment, this invention provides a compound according to formula IVa or IVB as described herein, wherein p is 1 and R² is methyl.

In another embodiment, this invention provides a compound according to formula IIIa or IIIB as described herein, wherein W is —SO₂N(R⁴)R⁵.

Exemplary compounds disclosed herein include, without limitation, those selected from the group consisting of:

1: 5-Chloro-N4-[4-[2-[N-(cyclopropylsulfonyl)amino]ethyl]phenyl]-N2-[(3aR,8aS)-2-oxo-3,3a,8,8a-tetrahydro-2H-indeno[1,2-d]oxazol-5-yl]-2,4-pyrimidinediamine;

2: 5-Methyl-N2-[(3aR,8aS)-2-oxo-3,3a,8,8a-tetrahydro-2H-indeno[1,2-d]oxazol-5-yl]-N4-(2,2,4-trimethyl-3-oxo-benz[1,4]oxazin-6-yl)-2,4-pyrimidinediamine;

3: N4-(2,2-Dimethyl-3-oxo-4H-benz[1,4]oxazin-6-yl)-5-methyl-N2-[(3aR,8aS)-2-oxo-3,3a,8,8a-tetrahydro-2H-indeno[1,2-d]oxazol-5-yl]-2,4-pyrimidinediamine;

4: 5-Methyl-N4-(4-methyl-3-oxo-2H-benz[1,4]thiazin-6-yl)-N2-[(3aR,8aS)-2-oxo-3,3a,8,8a-tetrahydro-2H-indeno[1,2-d]oxazol-5-yl]-2,4-pyrimidinediamine;

5: 5-Methyl-N2-[(3aR,8aS)-2-oxo-3,3a,8,8a-tetrahydro-2H-indeno[1,2-d]oxazol-5-yl]-N4-(2,2,4-trimethyl-3-oxo-5-pyrido[1,4]oxazin-6-yl)-2,4-pyrimidinediamine;

6: 5-Methyl-N4-(4-propyl-3-oxo-2H-benz[1,4]oxazin-6-yl)-N2-[(3aR,8aS)-2-oxo-3,3a,8,8a-tetrahydro-2H-indeno[1,2-d]oxazol-5-yl]-2,4-pyrimidinediamine;

7: 5-Methyl-N2-[(3aR,8aS)-2-oxo-3,3a,8,8a-tetrahydro-2H-indeno[1,2-d]oxazol-5-yl]-N4-(2,2,4-trimethyl-3-oxo-benz[1,4]thiazin-6-yl)-2,4-pyrimidinediamine;

8: 5-Chloro-N4-[4-[[N-(cyclopropylsulfonyl)amino]methyl]phenyl]-N2-[(3aR,8aS)-2-oxo-3,3a,8,8a-tetrahydro-2H-indeno[1,2-d]oxazol-5-yl]-2,4-pyrimidinediamine;

9: 5-Methyl-N2-[(3aS,8aR)-2-oxo-3,3a,8,8a-tetrahydro-2H-indeno[1,2-d]oxazol-5-yl]-N4-(2,2,4-trimethyl-3-oxo-benz[1,4]oxazin-6-yl)-2,4-pyrimidinediamine;

10: 5-Chloro-N2-[(3aS,8aR)-2-oxo-3,3a,8,8a-tetrahydro-2H-indeno[1,2-d]oxazol-5-yl]-N4-(2,2,4-trimethyl-3-oxo-benz[1,4]oxazin-6-yl)-2,4-pyrimidinediamine;

11: N4-(2,2-Dimethyl-4-ethyl-3-oxo-benz[1,4]oxazin-6-yl)-5-methyl-N2-[(3aS,8aR)-2-oxo-3,3a,8,8a-tetrahydro-2H-indeno[1,2-d]oxazol-5-yl]-2,4-pyrimidinediamine;

12: 5-Chloro-N4-(2,2-dimethyl-4-ethyl-3-oxo-benz[1,4]oxazin-6-yl)-N2-[(3aS,8aR)-2-oxo-3,3a,8,8a-tetrahydro-2H-indeno[1,2-d]oxazol-5-yl]-2,4-pyrimidinediamine;

13: N4-(2,2-Dimethyl-3-oxo-4H-benz[1,4]oxazin-6-yl)-5-methyl-N2-[(3aS,8aR)-2-oxo-3,3a,8,8a-tetrahydro-2H-indeno[1,2-d]oxazol-5-yl]-2,4-pyrimidinediamine;

14: 5-Chloro-N4-[3-[[(1,1-dimethylethyl)amino]sulfonyl]phenyl]-N2-[(3aS,8aR)-2-oxo-3,3a,8,8a-tetrahydro-2H-indeno[1,2-d]oxazol-5-yl]-2,4-pyrimidinediamine;

15: N4-[4-[[N-(Cyclopropylsulfonyl)amino]methyl]phenyl]-5-methyl-N2-[(3aS,8aR)-2-oxo-3,3a,8,8a-tetrahydro-2H-indeno[1,2-d]oxazol-5-yl]-2,4-pyrimidinediamine;

16: 5-Chloro-N4-[4-[[N-(cyclopropylsulfonyl)amino]methyl]phenyl]-N2-[(3aS,8aR)-2-oxo-3,3a,8,8a-tetrahydro-2H-indeno[1,2-d]oxazol-5-yl]-2,4-pyrimidinediamine;

17: 5-Chloro-N4-[4-[[N-(cyclopropylsulfonyl)amino]methyl]-2-methylphenyl]-N2-[(3aS,8aR)-2-oxo-3,3a,8,8a-tetrahydro-2H-indeno[1,2-d]oxazol-5-yl]-2,4-pyrimidinediamine;

18: N4-[4-[[N-(Cyclopropylsulfonyl)amino]methyl]-5-methyl-N2-[(3aS,8aR)-2-oxo-3,3a,8,8a-tetrahydro-2H-indeno[1,2-d]oxazol-5-yl]-2,4-pyrimidinediamine;

19: 5-Chloro-N4-(indan-4-yl)-5-methyl-N2-[(3aS,8aR)-2-oxo-3,3a,8,8a-tetrahydro-2H-indeno[1,2-d]oxazol-5-yl]-2,4-pyrimidinediamine;

20: N4-(Indan-4-yl)-5-methyl-N2-[(3aS,8aR)-2-oxo-3,3a,8,8a-tetrahydro-2H-indeno[1,2-d]oxazol-5-yl]-2,4-pyrimidinediamine;

21: 5-Chloro-N2-[(3aS,8aR)-2-oxo-3,3a,8,8a-tetrahydro-2H-indeno[1,2-d]oxazol-5-yl]-N4-(5,6,7,8-tetrahydronaphthalen-1-yl)2,4-pyrimidinediamine;

22: 5-Methyl-N2-[(3aS,8aR)-2-oxo-3,3a,8,8a-tetrahydro-2H-indeno[1,2-d]oxazol-5-yl]-N4-(5,6,7,8-tetrahydronaphthalen-1-yl)-2,4-pyrimidinediamine;

23: N4-(1,4-Benzodioxan-5-yl)-5-chloro-N2-[(3aS,8aR)-2-oxo-3,3a,8,8a-tetrahydro-2H-indeno[1,2-d]oxazol-5-yl]-2,4-pyrimidinediamine;

24: N4-(1,4-Benzodioxan-5-yl)-5-methyl-N2-[(3aS,8aR)-2-oxo-3,3a,8,8a-tetrahydro-2H-indeno[1,2-d]oxazol-5-yl]-2,4-pyrimidinediamine;

25: 5-Chloro-N4-(2,2-difluoro-1,3-benzodioxol-4-yl)-N2-[(3aS,8aR)-2-oxo-3,3a,8,8a-tetrahydro-2H-indeno[1,2-d]oxazol-5-yl]-2,4-pyrimidinediamine;

26: 5-Fluoro-N2-[(3aR,8aS)-2-oxo-3,3a,8,8a-tetrahydro-2H-indeno[1,2-d]oxazol-5-yl]-N4-[4-(pyridin-2-ylmethoxy)phenyl]-2,4-pyrimidinediamine;

27: 5-Methyl-N2-[(3aR,8aS)-2-oxo-3,3a,8,8a-tetrahydro-2H-indeno[1,2-d]oxazol-5-yl]-N4-[4-(pyridin-2-ylmethoxy)phenyl]-2,4-pyrimidinediamine;

28: 5-Methyl-N2-[(3aS,8aR)-2-oxo-3,3a,8,8a-tetrahydro-2H-indeno[1,2-d]oxazol-5-yl]-N4-[4-(pyridin-2-ylmethoxy)phenyl]-2,4-pyrimidinediamine;

29: 5-Fluoro-N2-[(3aR,8aS)-2-oxo-3,3a,8,8a-tetrahydro-2H-indeno[1,2-d]oxazol-5-yl]-N4-[4-[2-(pyridin-4-yl)ethyl]phenyl]-2,4-pyrimidinediamine;

30: 5-Fluoro-N2-[(3aS,8aR)-2-oxo-3,3a,8,8a-tetrahydro-2H-indeno[1,2-d]oxazol-5-yl]-N4-[4-(pyridin-2-ylmethoxy)phenyl]-2,4-pyrimidinediamine;

31: 5-Methyl-N2-[(3aR,8aS)-2-oxo-3,3a,8,8a-tetrahydro-2H-indeno[1,2-d]oxazol-5-yl]-N4-[4-(pyridin-3-ylmethoxy)phenyl]-2,4-pyrimidinediamine;

32: 5-Methyl-N2-[(3aS,8aR)-2-oxo-3,3a,8,8a-tetrahydro-2H-indeno[1,2-d]oxazol-5-yl]-N4-[4-(pyridin-3-ylmethoxy)phenyl]-2,4-pyrimidinediamine;

33: 5-Fluoro-N2-[(3aS,8aR)-2-oxo-3,3a,8,8a-tetrahydro-2H-indeno[1,2-d]oxazol-5-yl]-N4-[4-[2-(pyridin-4-yl)ethyl]phenyl]-2,4-pyrimidinediamine;

34: 5-Chloro-N4-(indan-4-yl)-5-methyl-N2-[(3aR,8aS)-2-oxo-3,3a,8,8a-tetrahydro-2H-indeno[1,2-d]oxazol-5-yl]-2,4-pyrimidinediamine;

35: N4-(Indan-4-yl)-5-methyl-N2-[(3aR,8aS)-2-oxo-3,3a,8,8a-tetrahydro-2H-indeno[1,2-d]oxazol-5-yl]-2,4-pyrimidinediamine;

36: 5-Chloro-N2-[(3aR,8aS)-2-oxo-3,3a,8,8a-tetrahydro-2H-indeno[1,2-d]oxazol-5-yl]-N4-(5,6,7,8-tetrahydronaphthalen-1-yl)2,4-pyrimidinediamine;

37: 5-Methyl-N2-[(3aR,8aS)-2-oxo-3,3a,8,8a-tetrahydro-2H-indeno[1,2-d]oxazol-5-yl]-N4-(5,6,7,8-tetrahydronaphthalen-1-yl)-2,4-pyrimidinediamine;

38: 5-Methyl-N2-[(4aR,9aS)-3-oxo-2,3,4,4a,9a-hexahydroindeno[2,1-b][1,4]oxazin-6-yl]-N4-(2,2,4-trimethyl-3-oxo-benz[1,4]oxazin-6-yl)-2,4-pyrimidinediamine;

39: N4-[4-[[N-(Cyclopropylsulfonyl)amino]methyl]phenyl]-5-methyl-N2-[(4aR,9aS)-3-oxo-2,3,4,4a,9a-hexahydroindeno[2,1-b][1,4]oxazin-6-yl]-2,4-pyrimidinediamine; and 40: 5-Chloro-N4-[4-[[N-(cyclopropylsulfonyl)amino]methyl]phenyl]-N2-[(4aR,9aS)-3-oxo-2,3,4,4a,9a-hexahydroindeno[2,1-b][1,4]oxazin-6-yl]-2,4-pyrimidinediamine.

In one embodiment, this invention provides salts of the compounds of this invention. In one embodiment, the salt is a pharmaceutically acceptable salt. Generally, pharmaceutically acceptable salts are those salts that retain substantially one or more of the desired pharmacological activities of the parent compound and which are suitable for administration to humans. Pharmaceutically acceptable salts include acid addition salts formed with inorganic acids or organic acids. Inorganic acids suitable for forming pharmaceutically acceptable acid addition salts include, by way of example and not limitation, hydrohalide acids (e.g., hydrochloric acid, hydrobromic acid, hydroiodic acid, etc.), sulfuric acid, nitric acid, phosphoric acid, and the like. Organic acids suitable for forming pharmaceutically acceptable acid addition salts include, by way of example and not limitation, acetic acid, trifluoroacetic acid, propionic acid, hexanoic acid, cyclopentanepropionic acid, glycolic acid, oxalic acid, pyruvic acid, lactic acid, malonic acid, succinic acid, malic acid, maleic acid, fumaric acid, tartaric acid, citric acid, palmitic acid, benzoic acid, 3-(4-hydroxybenzoyl)benzoic acid, cinnamic acid, mandelic acid, alkylsulfonic acids (e.g., methanesulfonic acid, ethanesulfonic acid, 1,2-ethane-disulfonic acid, 2-hydroxyethanesulfonic acid, etc.), arylsulfonic acids (e.g., benzenesulfonic acid, 4-chlorobenzenesulfonic acid, 2-naphthalenesulfonic acid, 4-toluenesulfonic acid, camphorsulfonic acid, etc.), 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like.

Pharmaceutically acceptable salts also include salts formed when an acidic proton present in the parent compound is either replaced by a metal ion (e.g., an alkali metal ion, an alkaline earth metal ion, or an aluminum ion) or coordinates with an organic base (e.g., ethanolamine, diethanolamine, triethanolamine, N-methylglucamine, morpholine, piperidine, dimethylamine, diethylamine, triethylamine, and ammonia).

The 2,4-pyrimidinediamines and the salts thereof, may also be in the form of hydrates, solvates, and N-oxides, as is well-known in the art.

In another embodiment, this invention provides compounds 1-40 listed in Table 1 below.

TABLE 1

| Compound # | Structure |
|---|---|
| 1 | 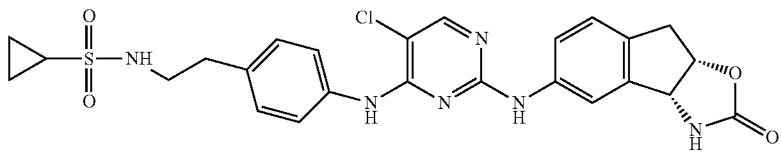 [SMILES: O=C1N[C@@H]2c3cc(Nc4ncc(Cl)c(Nc5ccc(CCNS(=O)(=O)C6CC6)cc5)n4)ccc3C[C@@H]2O1] |
| 2 | 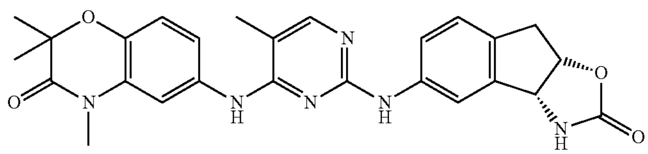 |
| 3 | 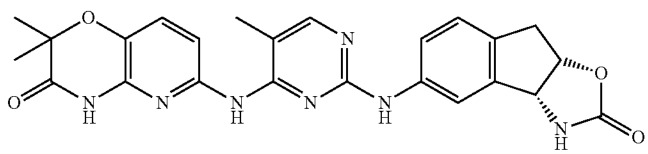 |
| 4 | 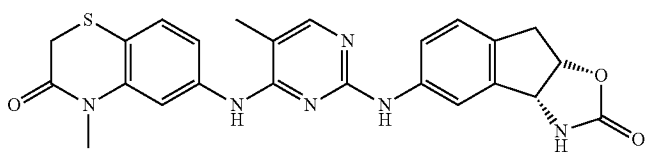 |
| 5 | 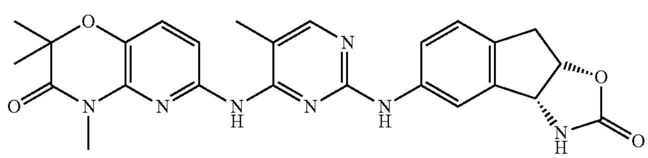 |
| 6 | 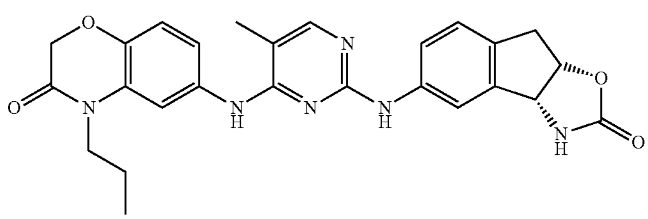 |
| 7 | 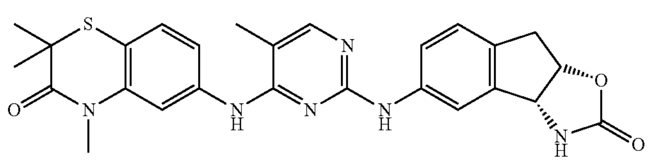 |
| 8 | 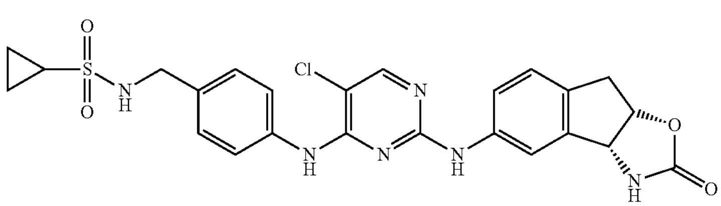 |
| 9 | 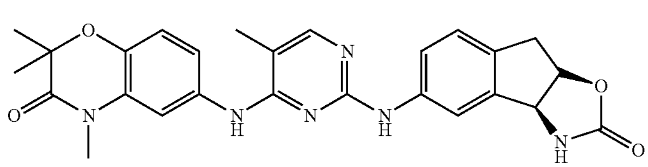 |

TABLE 1-continued

| Compound # | Structure |
| --- | --- |
| 10 | 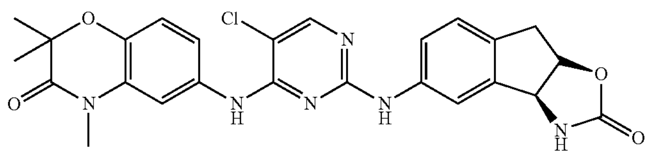 |
| 11 | 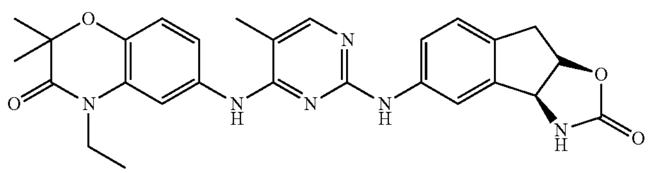 |
| 12 | 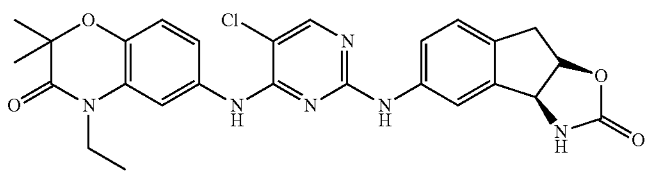 |
| 13 | 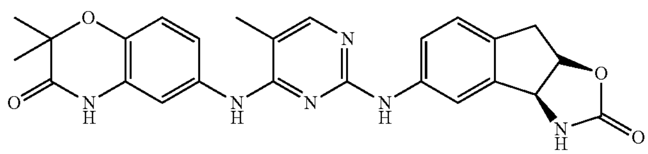 |
| 14 | 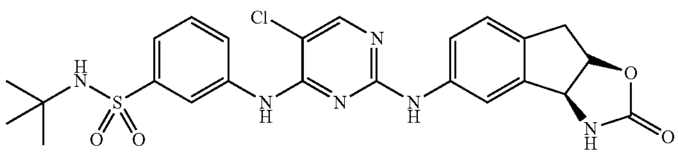 |
| 15 | 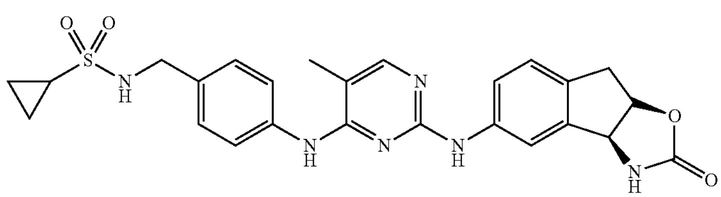 |
| 16 | 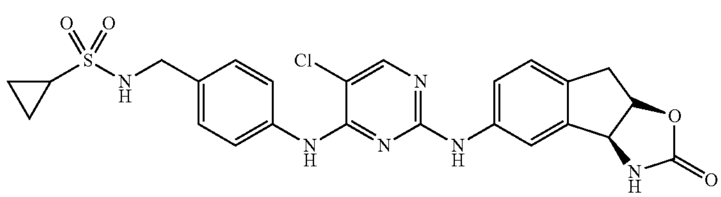 |
| 17 | 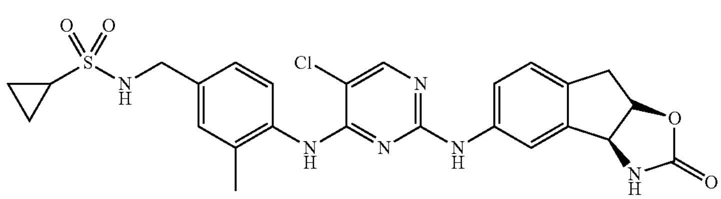 |

TABLE 1-continued

| Compound # | Structure |
|---|---|
| 18 | 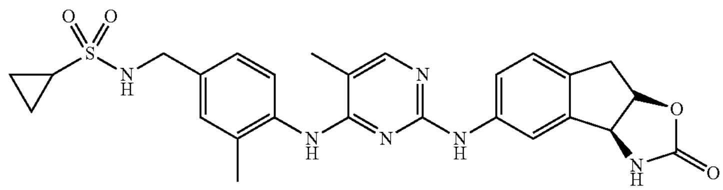 |
| 19 | 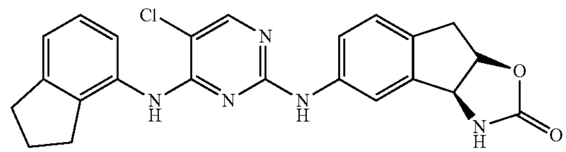 |
| 20 | 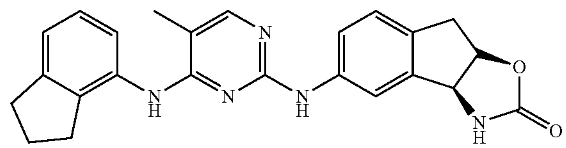 |
| 21 | 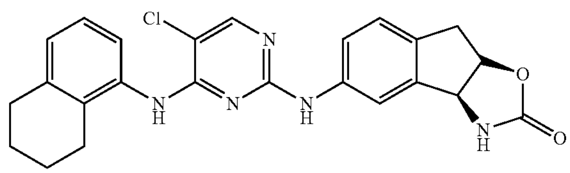 |
| 22 | 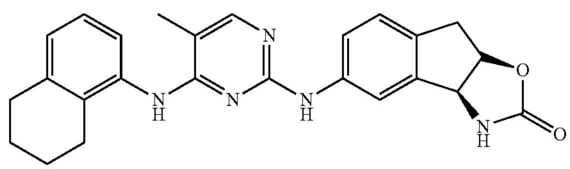 |
| 23 | 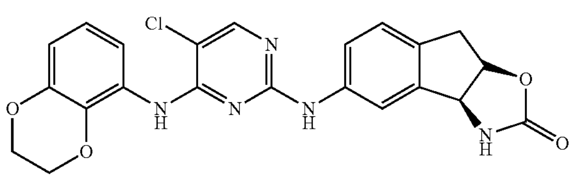 |
| 24 | 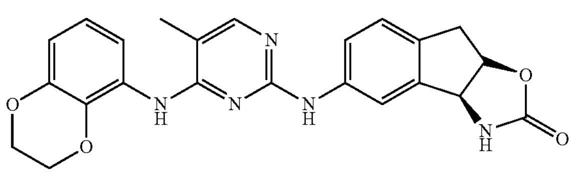 |
| 25 | 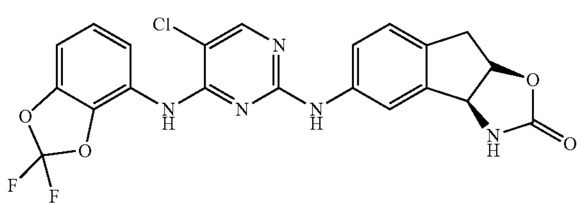 |
| 26 | 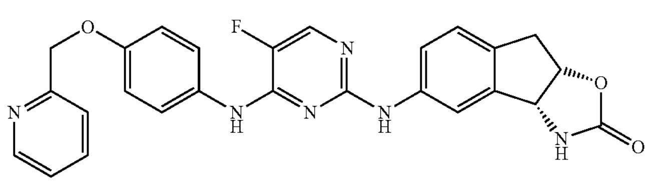 |

TABLE 1-continued
| Compound # | Structure |
|---|---|
| 27 | 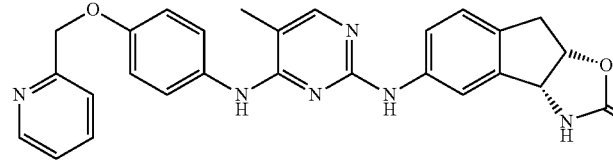 |
| 28 | 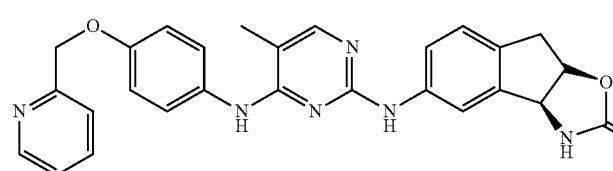 |
| 29 | 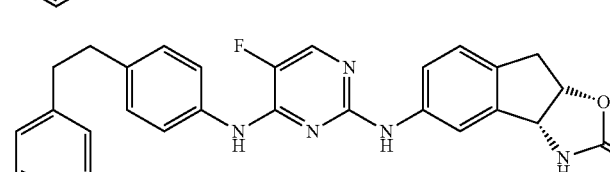 |
| 30 | 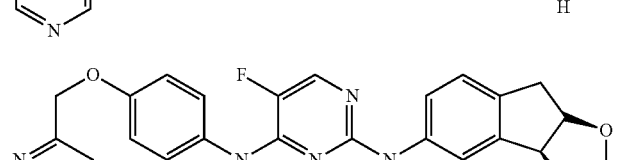 |
| 31 | 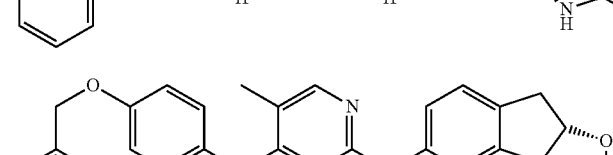 |
| 32 | 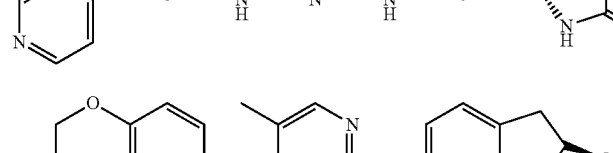 |
| 33 | 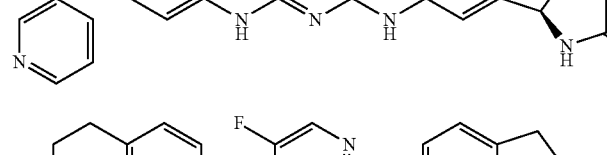 |
| 34 | 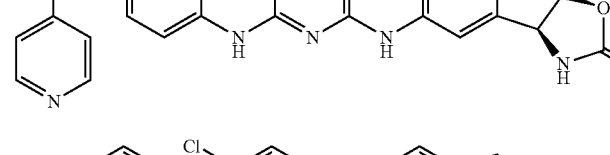 |
| 35 | 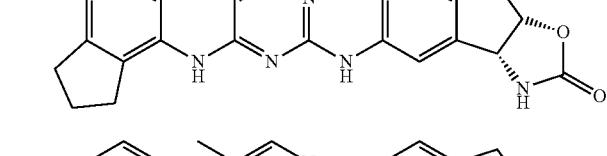 |

TABLE 1-continued

| Compound # | Structure |
|---|---|
| 36 | 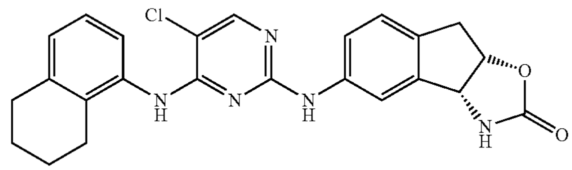 |
| 37 | 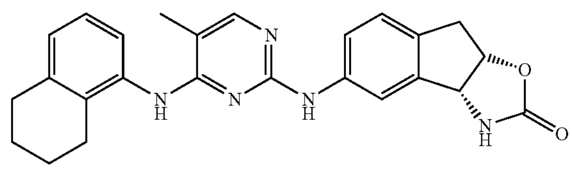 |
| 38 | 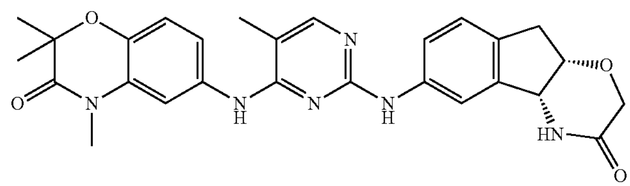 [SMILES: Cc1cnc(Nc2ccc3c(c2)[C@H]2NC(=O)CO[C@H]2C3)nc1Nc1ccc2c(c1)N(C)C(=O)C(C)(C)O2] |
| 39 | 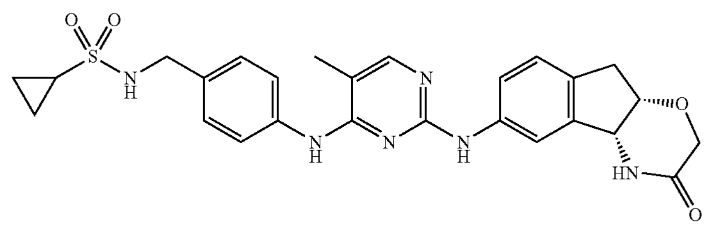 [SMILES: Cc1cnc(Nc2ccc3c(c2)[C@H]2NC(=O)CO[C@H]2C3)nc1Nc1ccc(CNS(=O)(=O)C2CC2)cc1] |
| 40 | 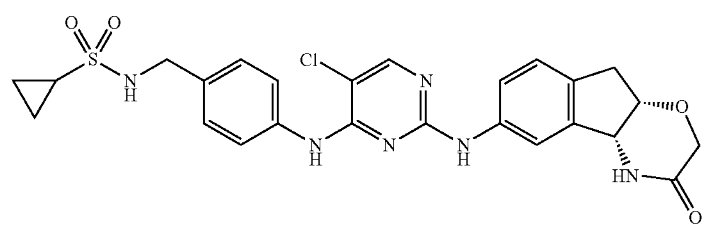 [SMILES: O=C1CO[C@H]2Cc3ccc(Nc4ncc(Cl)c(Nc5ccc(CNS(=O)(=O)C6CC6)cc5)n4)cc3[C@H]2N1] |

General Synthesis of the Compounds

The 2,4-pyrimidinediamine compounds disclosed herein may be synthesized via a variety of different synthetic routes using commercially available starting materials and/or starting materials prepared by conventional synthetic methods. Suitable exemplary methods that may be routinely adapted to synthesize the 2,4-pyrimidinediamine compounds of the invention are found in U.S. Pat. No. 5,958,935, the disclosure of which is incorporated herein by reference. Specific examples describing the synthesis of numerous 2,4-pyrimidinediamine compounds, as well as intermediates therefor, are described in copending U.S. application Ser. No. 10/355,543, filed Jan. 31, 2003 (US2004/0029902A1), the contents of which are incorporated herein by reference. Suitable exemplary methods that may be routinely used and/or adapted to synthesize active 2,4-substituted pyrimidinediamine compounds can also be found in international application Serial No. PCT/US03/03022 filed Jan. 31, 2003 (WO 03/063794), U.S. application Ser. No. 10/631,029 filed Jul. 29, 2003, international application Serial No. PCT/US03/24087 (WO2004/014382), U.S. application Ser. No. 10/903,263 filed Jul. 30, 2004 (US2005/0234049), and international application Serial No. PCT/US2004/24716 (WO005/016893), the disclosures of which are incorporated herein by reference. All of the compounds described herein may be prepared by routine adaptation of these methods.

Specific exemplary synthetic methods for the 2,4-substituted pyrimidinediamines described herein are also described in Example 1, below. Those of skill in the art will also be able to readily adapt these examples for the synthesis of additional 2,4-substituted pyrimidinediamines as described herein.

A variety of exemplary synthetic routes that can be used to synthesize the 2,4-substituted pyrimidinediamines compounds of the invention are described in Schemes (I)-(VII), below. These methods may be routinely adapted to synthesize the 2,4-substituted pyrimidinediamine compounds described herein.

Please note that in schemes (I)-(VII):

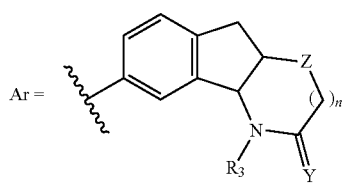

wherein n, Y, and Z are as defined herein.

In one exemplary embodiment, the compounds can be synthesized from substituted or unsubstituted uracils as illustrated in Scheme (I), below:

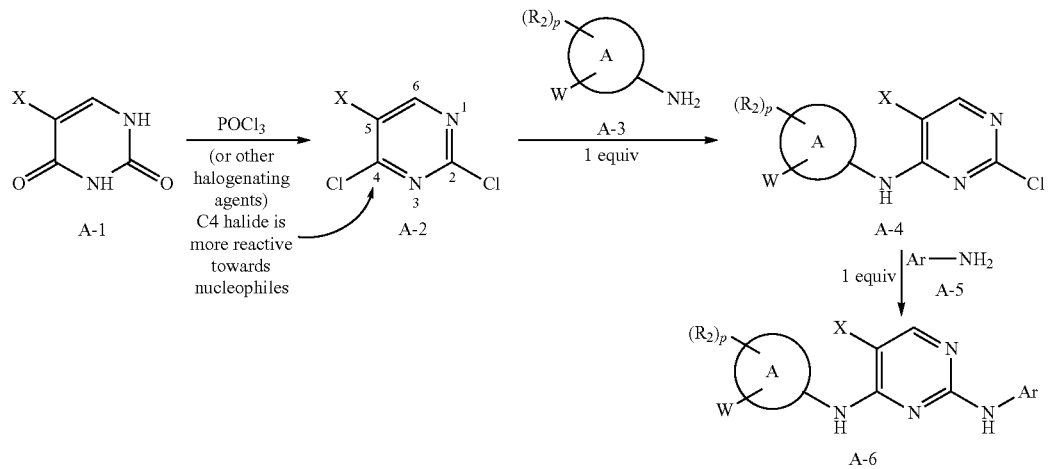

Scheme (I)

In Scheme (I), ring A, $(R^2)_p$, X, and W are as defined herein. According to Scheme (I), uracil A-1 is dihalogenated at the 2- and 4-positions using a standard halogenating agent such as $POCl_3$ (or other standard halogenating agent) under standard conditions to yield 2,4-dichloropyrimidine A-2. Depending upon the X substituent, in pyrimidinediamine A-2, the chloride at the C4 position is more reactive towards nucleophiles than the chloride at the C2 position. This differential reactivity can be exploited to synthesize 2,4-pyrimidinediamines A-7 by first reacting 2,4-dichloropyrimidine A-2 with one equivalent of amine A-3, yielding 4N-substituted-2-chloro-4-pyrimidineamine A-4, followed by amine A-5 to yield a 2,4-pyrimidinediamine derivative A-6, a compound of formula I.

Typically, the C4 halide is more reactive towards nucleophiles, as illustrated in the Scheme. However, as will be recognized by skilled artisans, the identity of the X substituent may alter this reactivity. For example, when X is trifluoromethyl, a 50:50 mixture of 4N-substituted-4-pyrimidineamine A-4 and the corresponding 2N-substituted-2-pyrimidineamine is obtained. The regioselectivity of the reaction can also be controlled by adjusting the solvent and other synthetic conditions (such as temperature), as is well-known in the art.

The reactions depicted in Scheme (I) may proceed more quickly when the reaction mixtures are heated via microwave. When heating in this fashion, the following conditions can be used: heat to 175° C. in ethanol for 5-20 min. in a Smith Reactor (Personal Chemistry, Uppsala, Sweden) in a sealed tube (at 20 bar pressure).

The uracil A-1 starting materials can be purchased from commercial sources or prepared using standard techniques of organic chemistry. Commercially available uracils that can be used as starting materials in Scheme (I) include, by way of example and not limitation, uracil (Aldrich #13,078-8; CAS Registry 66-22-8); 5-bromouracil (Aldrich #85,247-3; CAS Registry 51-20-7; 5-fluorouracil (Aldrich #85,847-1; CAS Registry 51-21-8); 5-iodouracil (Aldrich #85,785-8; CAS Registry 696-07-1); 5-nitrouracil (Aldrich #85,276-7; CAS Registry 611-08-5); 5-(trifluoromethyl)-uracil (Aldrich #22, 327-1; CAS Registry 54-20-6). Additional 5-substituted uracils are available from General Intermediates of Canada, Inc., Edmonton, CA and/or Interchim, Cedex, France, or can be prepared using standard techniques. Myriad textbook references teaching suitable synthetic methods are provided infra.

Amines A-3 and A-5 can be purchased from commercial sources or, alternatively, can be synthesized utilizing standard techniques. For example, suitable amines can be synthesized from nitro precursors using standard chemistry. Specific exemplary reactions are provided in the Examples section. See also Vogel, 1989, *Practical Organic Chemistry*, Addison Wesley Longman, Ltd. and John Wiley & Sons, Inc.

Skilled artisans will recognize that in some instances, amines A-3 and A-5 and/or substituent X on uracil A-1 may include functional groups that require protection during synthesis. The exact identity of any protecting group(s) used will depend upon the identity of the functional group being protected, and will be apparent to those of skill in the art. Guidance for selecting appropriate protecting groups, as well as synthetic strategies for their attachment and removal, can be found, for example, in Greene & Wuts, *Protective Groups in Organic Synthesis*, 3d Edition, John Wiley & Sons, Inc., New York (1999) and the references cited therein (hereinafter "Greene & Wuts").

Thus, protecting group refers to a group of atoms that, when attached to a reactive functional group in a molecule, mask, reduce or prevent the reactivity of the functional group. Typically, a protecting group can be selectively removed as desired during the course of a synthesis. Examples of protecting groups can be found in Greene and Wuts, as mentioned above, and additionally, in Harrison et al., *Compendium of Synthetic Organic Methods*, Vols. 1-8, 1971-1996, John Wiley & Sons, NY. Representative amino protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("TES"), trityl and substituted trityl groups, allyloxycarbonyl, 9-fluorenylmethyloxycarbonyl ("FMOC"), nitro-veratryloxycarbonyl ("NVOC") and the like. Representative hydroxyl protecting groups include, but are not limited to, those where the hydroxyl group is either acylated to form acetate and benzoate esters or alkylated to form benzyl and trityl ethers, as well as alkyl ethers, tetrahydropyranyl ethers, trialkylsilyl ethers (e.g., TMS or TIPPS groups) and allyl ethers.

A specific embodiment of Scheme (I) utilizing 5-fluorouracil (Aldrich #32,937-1) as a starting material is illustrated in Scheme (Ia), below. Ring A, $(R^2)_p$, and W are as previously defined for Scheme (I). Asymmetric 2N,4N-disubstituted-5-fluoro-2,4-pyrimidinediamine A-10 can be obtained by reacting 2,4-dichloro-5-fluoropyrimidine A-8 with one equivalent of amine A-3 (to yield 2-chloro-N4-substituted-5-fluoro-4-pyrimidineamine A-10 followed by one or more equivalents of amine A-5.

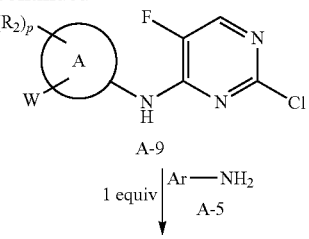

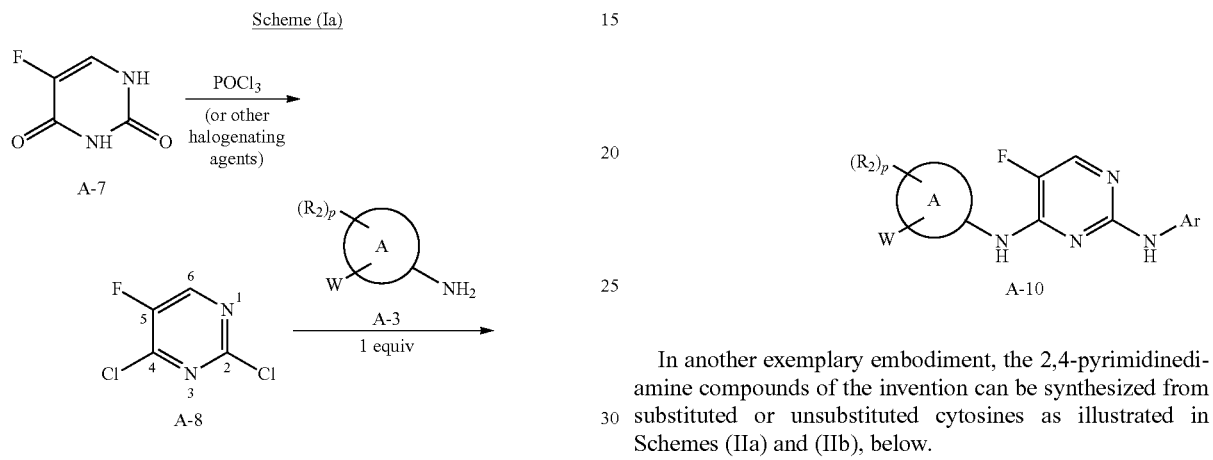

In another exemplary embodiment, the 2,4-pyrimidinediamine compounds of the invention can be synthesized from substituted or unsubstituted cytosines as illustrated in Schemes (IIa) and (IIb), below.

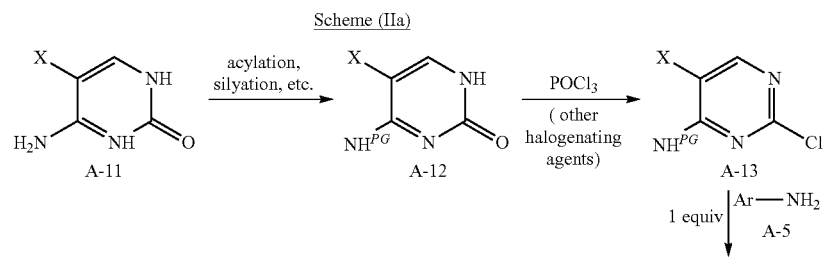

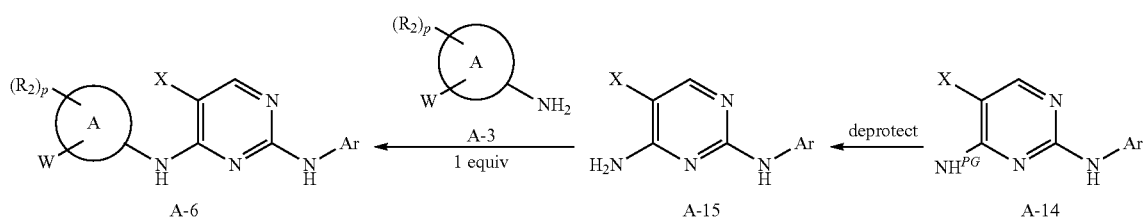

In Schemes (IIa) and (IIb), ring A, $(R^2)_p$, X, and W are as previously defined for Scheme (I). and PG represents a protecting group. Referring to Scheme (IIa), the C4 exocyclic amine of cytosine A-11 is first protected with a suitable protecting group PG to yield N4-protected cytosine A-12. For specific guidance regarding protecting groups useful in this context, see Vorbrüggen and Ruh-Pohlenz, 2001, *Handbook of Nucleoside Synthesis*, John Wiley & Sons, NY, pp. 1-631 ("Vorbrüggen"). Protected cytosine A-12 is halogenated at the C2 position using a standard halogenation reagent under standard conditions to yield 2-chloro-4N-protected-4-pyrimidineamine A-13. Reaction with amine A-5 gives A-14, which on deprotection of the C4 exocyclic amine, gives A-15. Reaction of A-15 with amine A-3 yields 2,4-pyrimidinediamine derivative A-6.

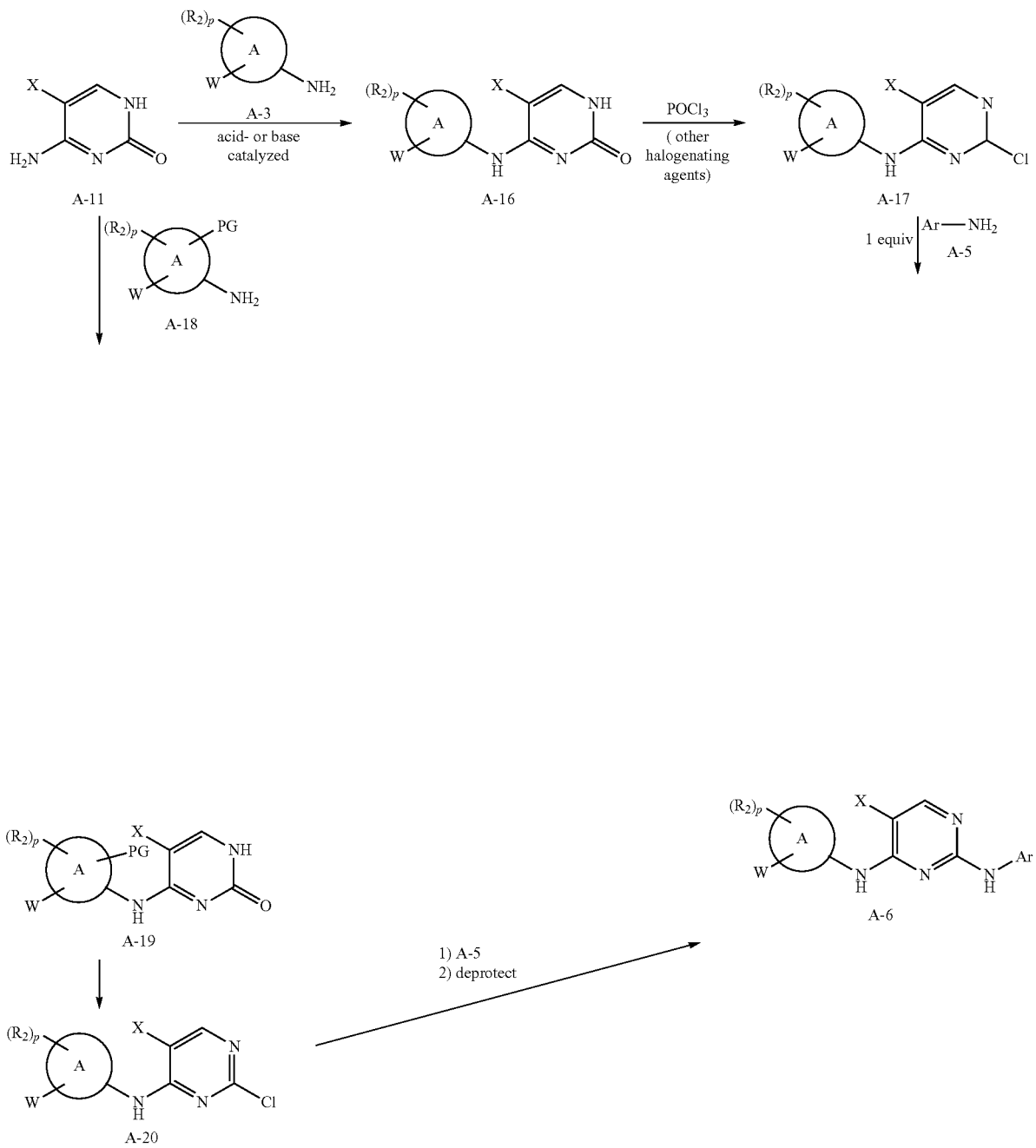

Alternatively, referring to Scheme (IIb), cytosine A-11 can be reacted with amine A-3 or protected amine A-18 to yield N4-substituted cytosine A-16 or A-19, respectively. These substituted cytosines may then be halogenated as previously described, reacted with amine A-5, and deprotected (in the case of N4-substituted cytosine A-19) to yield a 2,4-pyrimidinediamine A-6.

Commercially-available cytosines that can be used as starting materials in Schemes (IIa) and (IIb) include, but are not limited to, cytosine (Aldrich #14,201-8; CAS Registry 71-30-7); N⁴-acetylcytosine (Aldrich #37,791-0; CAS Registry 14631-20-0); 5-fluorocytosine (Aldrich #27,159-4; CAS Registry 2022-85-7); and 5-(trifluoromethyl)-cytosine. Other suitable cytosines useful as starting materials in Schemes (IIa) are available from General Intermediates of Canada, Inc., Edmonton, CA and/or Interchim, Cedex, France, or can be prepared using standard techniques. Myriad textbook references teaching suitable synthetic methods are provided infra.

In still another exemplary embodiment, the 2,4-pyrimidinediamine compounds of the invention can be synthesized from substituted or unsubstituted 2-amino-4-pyrimidinols as illustrated in Scheme (III), below:

available from General Intermediates of Canada, Inc., Edmonton, CA and/or Interchim, Cedex, France, or can be prepared using standard techniques. Myriad textbook references teaching suitable synthetic methods are provided infra.

Alternatively, the 2,4-pyrimidinediamine compounds of the invention can be prepared from substituted or unsubstituted 4-amino-2-pyrimidinols as illustrated in Scheme (IV), below. Ring A, $(R^2)_p$, X, and W are as previously defined for Scheme (I). Referring to Scheme (IV), the C2-hydroxyl of 4-amino-2-pyrimidinol A-25 is more reactive towards nucleophiles than the C4-amino such that reaction with amine A-5 yields N2-substituted-2,4-pyrimidinediamine A-26. Subsequent reaction with compound A-27, which includes a suitable leaving group, or amine A-3 yields a 2,4-pyrimidinediamine derivative A-6. Compound A-27 may include virtually any leaving group that can be displaced by the C4-amino of N2-substituted-2,4-pyrimidinediamine A-26. Suitable leaving groups include, but are not limited to, halogens, methanesulfonyloxy (mesyloxy; "OMs"), trifluoromethanesulfonyloxy ("OTf") and p-toluenesulfonyloxy (tosyloxy; "OTs"), benzene sulfonyloxy ("besylate") and

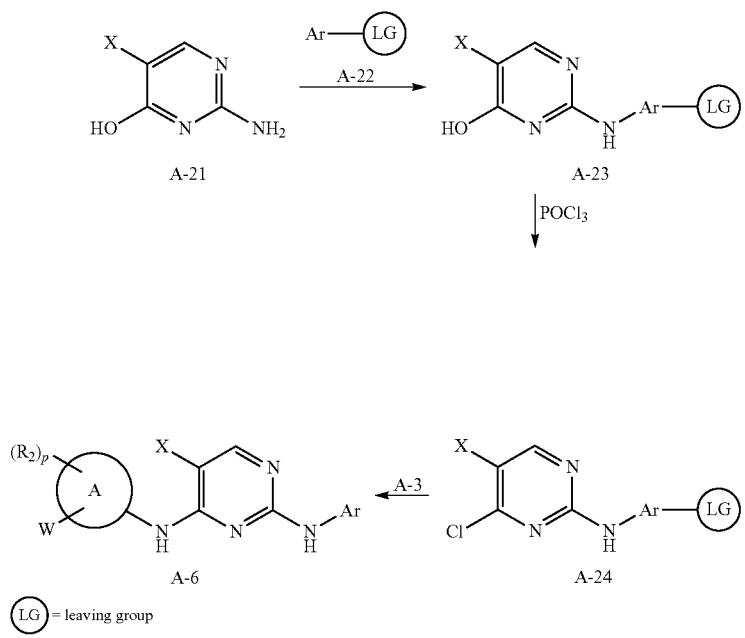

Scheme (III)

In Scheme (III), ring A, $(R^2)_p$, X, and W are as previously defined for Scheme (I) and LG is a leaving group as discussed in more detail in connection with Scheme IV, infra. Referring to Scheme (III), 2-amino-4-pyrimidinol A-21 is reacted with arylating agent A-22 to yield N2-substituted-4-pyrimidinol A-23, which is then halogenated as previously described to yield N2-substituted-4-halo-2-pyrimidineamine A-24. Further reaction with amine A-3 affords a 2,4-pyrimidinediamine derivative A-6.

Suitable commercially-available 2-amino-4-pyrimidinols A-21 that can be used as starting materials in Scheme (III) are m-nitro benzene sulfonyloxy ("nosylate"). Other suitable leaving groups will be apparent to those of skill in the art.

Scheme (IV)

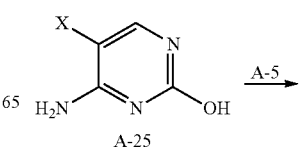

A-25

-continued

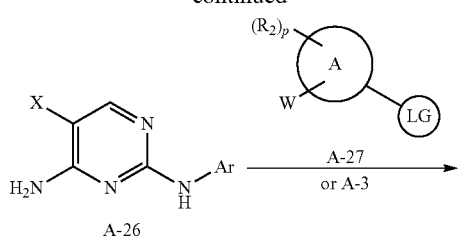

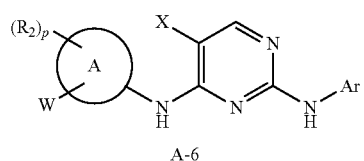

LG = leaving group

Substituted 4-amino-2-pyrimidinol starting materials can be obtained commercially or synthesized using standard techniques. Myriad textbook references teaching suitable synthetic methods are provided infra.

In still another exemplary embodiment, the 2,4-pyrimidinediamine compounds of the invention can be prepared from 2-chloro-4-aminopyrimidines or 2-amino-4-chloropyrimidines as illustrated in Scheme (V). Ring A, $(R^2)_p$, X, and W are as previously defined for Scheme (I) and leaving group is as defined for Scheme (IV). Referring to Scheme (V), 2-amino-4-chloro-pyrimidine A-28 is reacted with amine A-3 to yield 4N-substituted-2,4-pyrimidinediamine A-29 which, following reaction with compound A-22 or amine A-5, yields a N2,N4-2,4-pyrimidine-diamine derivative A-6. Alternatively, 2-chloro-4-amino-pyrimidine A-30 can be reacted with compound A-27 to give compound A-31 which on reaction with amine A-5 yields A-6.

A variety of pyrimidines A-28 and A-30 suitable for use as starting materials in Scheme (V) are commercially available from General Intermediates of Canada, Inc., Edmonton, CA and/or Interchim, Cedex, France, or can be prepared using standard techniques. Myriad textbook references teaching suitable synthetic methods are provided infra.

Scheme (V)

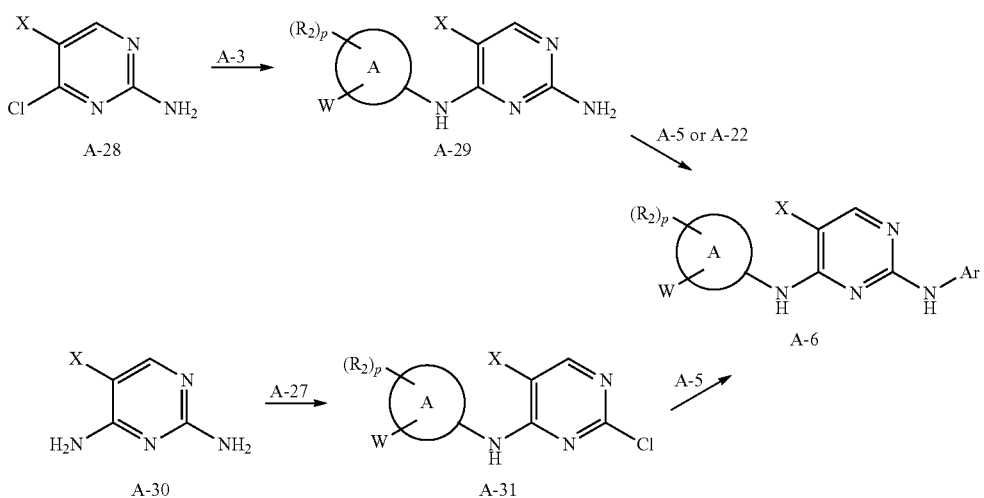

Alternatively, 4-chloro-2-pyrimidineamines A-28 can be prepared as illustrated in Scheme (Va):

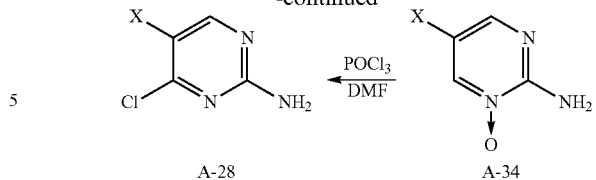

In Scheme (Va), X is as previously defined for Scheme I. In Scheme (Va), dialdehyde A-32 is reacted with guanidine to yield 2-pyrimidineamine A-33. Reaction with a peracid such as m-chloroperbenzoic acid, trifluoroperacetic acid or urea hydrogen peroxide complex yields N-oxide A-34, which is then halogenated to give 4-chloro-2-pyrimidineamine A-28. The corresponding 4-halo-2-pyrimidineamines can be obtained by using suitable halogenation reagents.

In yet another exemplary embodiment, the 2,4-pyrimidinediamine compounds of the invention can be prepared from substituted or unsubstituted uridines as illustrated in Scheme (VI), below:

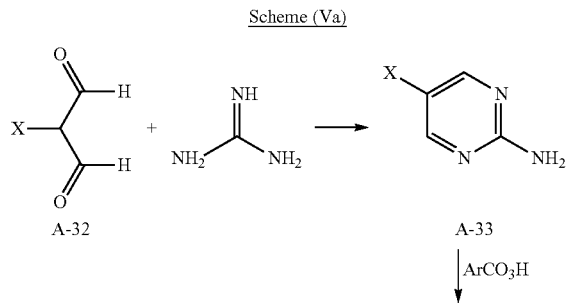

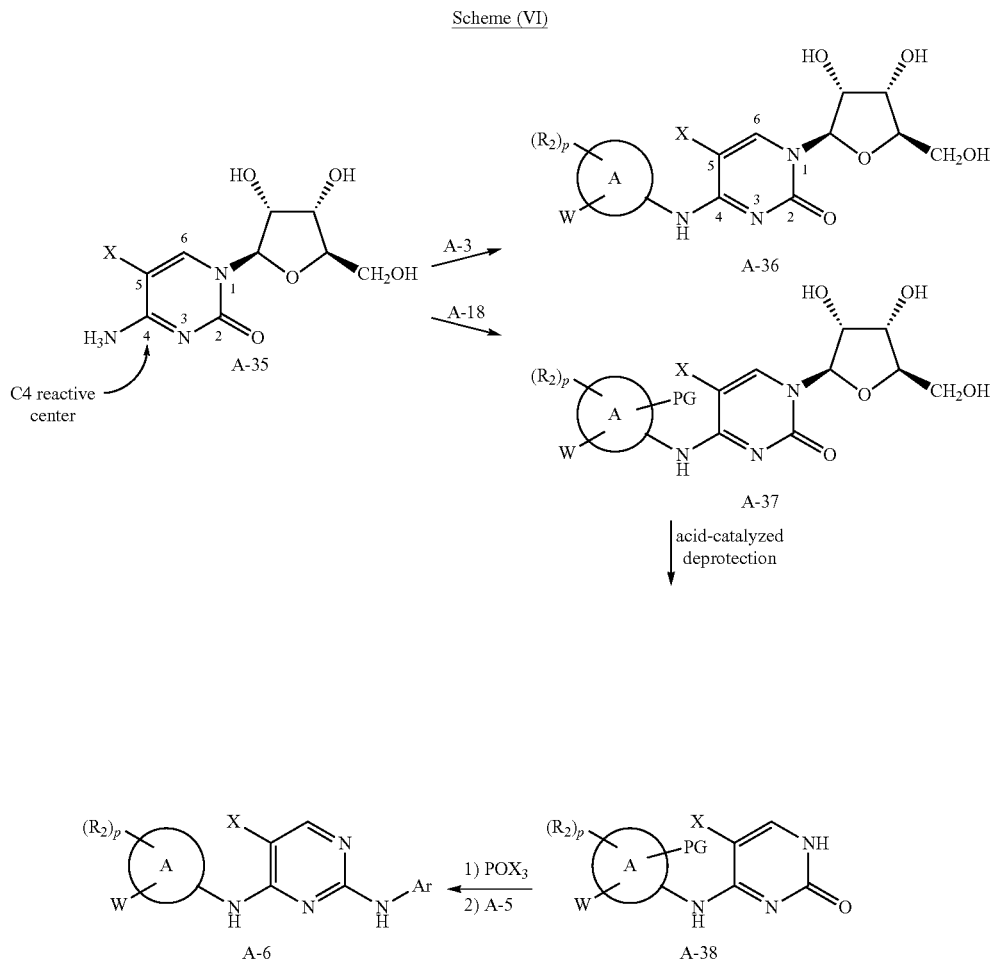

In Scheme (VI), ring A, $(R^2)_p$, X, and W are as previously defined for Scheme I and PG represents a protecting group, as discussed in connection with Scheme (IIb). According to Scheme (VI), uridine A-35 has a C4 reactive center such that reaction with amine A-3 or protected amine A-18 yields N4-substituted cytidine A-36 or A-37, respectively. Acid-catalyzed deprotection of N4-substituted A-36 or A-37 (when "PG" represents an acid-labile protecting group) yields N4-substituted cytosine A-38, which can be subsequently halogenated at the C2-position and reacted with amine A-5 to yield a 2,4-pyrimidinediamine derivative A-6.

Cytidines may also be used as starting materials in an analogous manner, as illustrated in Scheme (VII), below. Ring A, $(R^2)_p$, X, and W are as previously defined in Scheme (I) and PG represents a protecting group as discussed above. Referring to Scheme (VII), like uridine A-35, cytidine A-39 has a C4 reactive center such that reaction with amine A-3 or protected amine A-18 yields N4-substituted cytidine A-36 or A-37, respectively. These cytidines A-36 and A-37 are then treated as previously described for Scheme (VI) to yield a 2,4-pyrimidinediamine derivative A-6.

5-(trifluoromethyl)uridine (Chem. Sources Int'l 2000; CAS Registry 70-00-8); 5-trifluoromethyl-2'-deoxyuridine (Chem. Sources Int'l 2000; CAS Registry 70-00-8). Additional uridines and cytidines that can be used as starting materials in Schemes (VI) and (VII) are available from General Intermediates of Canada, Inc., Edmonton, CA and/or Interchim, Cedex, France, or can be prepared using standard techniques. Myriad textbook references teaching suitable synthetic methods are provided infra.

Although many of the synthetic schemes discussed above do not illustrate the use of protecting groups, skilled artisans will recognize that in some instances certain substituents, such as, for example, $R^2$ and/or $R^4$, may include functional groups requiring protection. The exact identity of the protecting group used will depend upon, among other things, the identity of the functional group being protected and the reaction conditions used in the particular synthetic scheme, and will be apparent to those of skill in the art. Guidance for selecting protecting groups, their attachment and removal suitable for a particular application can be found, for example, in Greene & Wuts, supra.

Scheme (VII)

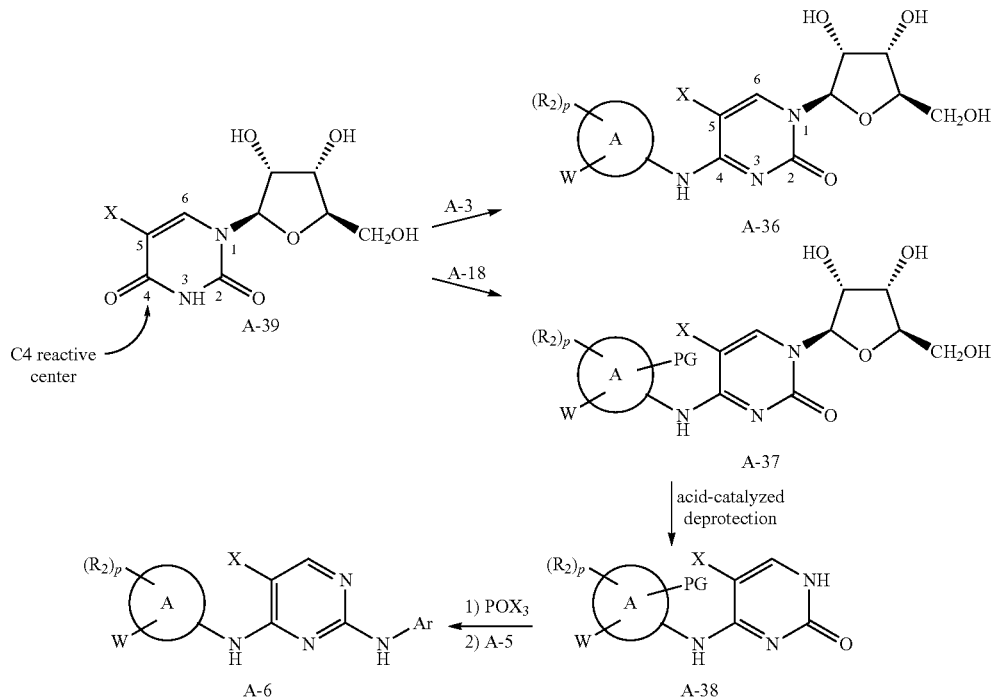

Although Schemes (VI) and (VII) are exemplified with ribosylnucleosides, skilled artisans will appreciate that the corresponding 2'-deoxyribo and 2',3'-dideoxyribo nucleosides, as well as nucleosides including sugars or sugar analogs other than ribose, would also work.

Numerous uridines and cytidines useful as starting materials in Schemes (VI) and (VII) are known in the art, and include, by way of example and not limitation, 5-trifluoromethyl-2'-deoxycytidine (Chem. Sources #ABCR F07669; CAS Registry 66,384-66-5); 5-bromouridine (Chem. Sources Int'l 2000; CAS Registry 957-75-5); 5-iodo-2'-deoxyuridine (Aldrich #1-775-6; CAS Registry 54-42-2); 5-fluorouridine (Aldrich #32,937-1; CAS Registry 316-46-1); 5-iodouridine (Aldrich #85,259-7; CAS Registry 1024-99-3);

Myriad references teaching methods useful for synthesizing pyrimidines generally, as well as starting materials described in Schemes (I)-(VII), are known in the art. For specific guidance, the reader is referred to Brown, D. J., "The Pyrimidines", in *The Chemistry of Heterocyclic Compounds, Volume* 16 (Weissberger, A., Ed.), 1962, Interscience Publishers, (A Division of John Wiley & Sons), New York ("Brown I"); Brown, D. J., "The Pyrimidines", in *The Chemistry of Heterocyclic Compounds, Volume* 16, *Supplement I* (Weissberger, A. and Taylor, E. C., Ed.), 1970, Wiley-Interscience, (A Division of John Wiley & Sons), New York (Brown II"); Brown, D. J., "The Pyrimidines", in *The Chemistry of Heterocyclic Compounds, Volume* 16, *Supplement II* (Weissberger, A. and Taylor, E. C., Ed.), 1985, An Interscience Publication (John Wiley & Sons), New York ("Brown III"); Brown, D. J., "The Pyrimidines" in *The Chemistry of Heterocyclic Compounds, Volume* 52 (Weissberger, A. and Taylor, E. C., Ed.), 1994, John Wiley & Sons, Inc., New York, pp. 1-1509 (Brown IV"); Kenner, G. W. and Todd, A., in *Heterocyclic Compounds*, Volume 6, (Elderfield, R. C., Ed.), 1957, John Wiley, New York, Chapter 7 (pyrimidines); Paquette, L. A., *Principles of Modern Heterocyclic Chemistry*, 1968, W. A. Benjamin, Inc., New York, pp. 1-401 (uracil synthesis pp. 313, 315; pyrimidinediamine synthesis pp. 313-316; amino pyrimidinediamine synthesis pp. 315); Joule, J. A., Mills, K. and Smith, G. F., *Heterocyclic Chemistry*, $3^{rd}$ Edition, 1995, Chapman and Hall, London, UK, pp. 1-516; Vorbrüggen, H. and Ruh-Pohlenz, C., *Handbook of Nucleoside Synthesis*, John Wiley & Sons, New York, 2001, pp. 1-631 (protection of pyrimidines by acylation pp. 90-91; silylation of pyrimidines pp. 91-93); Joule, J. A., Mills, K. and Smith, G. F., *Heterocyclic Chemistry*, $4^{th}$ Edition, 2000, Blackwell Science, Ltd, Oxford, UK, pp. 1-589; and Comprehensive Organic Synthesis, Volumes 1-9 (Trost, B. M. and Fleming, I., Ed.), 1991, Pergamon Press, Oxford, UK.

Methods of the Invention

The present invention provides 2,4-pyrimidinediamines substituted at N2 with tricyclic carbamates, tautomers, N-oxides, salts thereof, as described herein, for use in therapy for the conditions described herein. The present invention further provides use of the compounds of the present invention in the manufacture of a medicament for the treatment of conditions in which targeting of the JAK pathway or inhibition of JAK kinases, particularly JAK2, are therapeutically useful. The methods include conditions where the function of lymphocytes, macrophages, or mast cells is involved. Conditions in which targeting of the JAK pathway or inhibition of the JAK kinases, particularly JAK2, are therapeutically useful include but are not limited to, leukemia, lymphoma, multiple myeloma, transplant rejection (e.g. pancreas islet transplant rejection), bone marrow transplant conditions (e.g., graft-versus-host disease)), autoimmune diseases (e.g., rheumatoid arthritis), inflammation (e.g., asthma, etc.) myeloproliferative disorders (MPD) (e.g., polycythemia vera (PV), essential thrombocythemia (ET) and primary myelofibrosis (PMF)), and other diseases or conditions as described in greater detail herein or which are known to one skilled in the art as being associated with JAK2 activity.

As noted previously, numerous conditions can be treated using the 2,4-substituted pyrimidinediamine compounds and methods of treatment as described herein. As used herein, "Treating" or "treatment" of a disease in a patient refers to (1) preventing the disease from occurring in a patient that is predisposed or does not yet display symptoms of the disease; (2) inhibiting the disease or arresting its development; or (3) ameliorating or causing regression of the disease. As well understood in the art, "treatment" is an approach for obtaining beneficial or desired results, including clinical results. For the purposes of this invention, beneficial or desired results can include one or more, but are not limited to, alleviation or amelioration of one or more symptoms, diminishment of extent of a condition, including a disease, stabilized (i.e., not worsening) state of a condition, including diseases, preventing spread of disease, delay or slowing of condition, including disease, progression, amelioration or palliation of the condition, including disease, state, and remission (whether partial or total), whether detectable or undetectable. Preferred are compounds that are potent and can be administered locally at very low doses, thus minimizing systemic adverse effects.

The compounds of the invention, or pharmaceutically acceptable salts thereof, described herein are potent and selective inhibitors of JAK kinases, and particularly selective for cytokine signaling pathways containing JAK2. As a consequence of this activity, the compounds can be used in a variety of in vitro, in vivo and ex vivo contexts to regulate or inhibit JAK kinase activity, signaling cascades in which JAK kinases play a role, and the biological responses effected by such signaling cascades. For example, in one embodiment, the compounds can be used to inhibit JAK kinase, either in vitro or in vivo, in virtually any cell type expressing the JAK kinase.

In hematopoietic cells in which a JAK kinase is expressed, the compounds of the invention may be used to regulate signal transduction cascades in which the JAK kinase, particularly JAK2, plays a role. Such JAK-dependent signal transduction cascades include, but are not limited to, the signaling cascades of cytokine receptors that involve wide range of cytokine receptors, including those activated by growth hormone, erythropoietin, prolactin, granulocyte colony stimulating factor (G-CSF), macrophage colony-stimulating factor, ciliary neurotrophic factor, leukemia inhibitory factor, oncostatin M, interferon-γ, thrombopoietin, leptin, IL-3, IL-5, IL-6, IL-11, IL-12 and some G-protein-coupled (GPCR) receptor signalling cascades (angiotensin II, bradykinin, endothelin, platelet activating factor, α-melanocyte stimulating hormone, isoproterenol, and phenylephrine). The compounds may also be used in vitro or in vivo to regulate, and in particular inhibit, cellular or biological responses affected by such JAK-dependent signal transduction cascades. Such cellular or biological responses include, but are not limited to, MAPK and AKT pathway activation, IL-3 mediated cell proliferation, etc.

Importantly, the compounds can be used to inhibit JAK kinases in vivo as a therapeutic approach towards the treatment or prevention of diseases or conditions mediated, either wholly or in part, by a JAK kinase activity (referred to herein as "JAK kinase mediated diseases or conditions"). Non-limiting examples of JAK kinase mediated diseases or conditions that can be treated or prevented with the compounds of the invention, or pharmaceutically acceptable salts thereof, include, but are not limited to allergies, asthma, autoimmune diseases such as transplant rejection (e.g., kidney, heart, lung, liver, pancreas, skin; host versus graft reaction (HVGR), graft versus host reaction (GVHR) etc.), rheumatoid arthritis, and amyotrophic lateral sclerosis, T-cell mediated autoimmune diseases such as multiple sclerosis, psoriasis and Sjogren's syndrome, Type II inflammatory diseases such as vascular inflammation (including vasculitis, arteritis, atherosclerosis and coronary artery disease), diseases of the central nervous system such as stroke, pulmonary diseases such as bronchitis obliteraus and primary pulmonary hypertension, and solid, delayed Type IV hypersensitivity reactions, and hematologic malignancies such as leukemia and lymphomas.

In one embodiment, this invention provides a method of inhibiting an activity of a JAK kinase comprising contacting the JAK kinase with an amount of a compound according to formula I as described herein, to inhibit an activity of the JAK kinase. In certain embodiments of the methods described herein, the JAK kinase is a JAK2 kinase.

In another embodiment, this invention provides a method of inhibiting an activity of a JAK kinase, comprising contacting in vitro a JAK kinase with an amount of a compound according to formula I as described herein, to inhibit an activity of the JAK kinase. In certain embodiments of the methods described herein, the JAK kinase is a JAK2 kinase.

In another embodiment, this invention provides a method of treating a disease or condition associated with JAK2 activity in a subject, wherein the method comprises administering to the subject a therapeutically effective amount of a compound of formula (I) as described herein.

In certain embodiments, the presently disclosed compounds are useful for the treatment or management of hyperproliferative disorders. By way of example disorders that can be treated using the presently disclosed compounds include, without limitation, leukemia, lymphoma, multiple myeloma, transplant rejection, bone marrow transplant applications, autoimmune diseases, inflammation, myeloproliferative disorders, polycythemia vera disorder, essential thrombocythemia disorder and primary myelofibrosis.

In one embodiment of treating or managing a proliferative disorder in a subject includes administering to the patient in need thereof a therapeutically or prophylactically effective amount of a JAK inhibitor disclosed herein, in combination with the administration of a therapeutically or prophylactically effective amount of a different chemotherapeutic agent. Examples of compounds suitable for use in combination with the presently disclosed compounds include antimetabolites, alkylating agents, coordination compounds, platinum complexes, DNA cross-linking compounds, inhibitors of transcription enzymes, tyrosine kinase inhibitors, protein kinase inhibitors, topoisomerase inhibitors, DNA minor-groove binding compounds, vinca alkyloids, taxanes, antitumor antibiotics, hormones, aromatase inhibitors, enzymes, growth factor receptors antibodies, cytokines, cell surface markers antibodies, HDAC inhibitors, HSP 90 inhibitors, BCL-2 inhibitors, mTOR inhibitors, proteasome inhibitors and monoclonal antibodies.

In another embodiment of methods of treating or managing a proliferative disorder in a patient includes administering to the patient in need thereof a therapeutically or prophylactically effective amount of a JAK2 inhibitor in combination with the administration of a therapeutically or prophylactically effective amount of one or more chemotherapeutic agents, selected from mechlorethamine, cyclophosphamide, ifosfamide, melphalan, chlorambucil, ethyleneimines, methylmelamines, procarbazine, dacarbazine, temozolomide, busulfan, carmustine, lomustine, methotrexate, fluorouracil, capecitabine, cytarabine, gemcitabine, cytosine arabinoside, mecaptopurine, fludarabine, cladribine, thioguanine, azathioprine, vinblastine, vincristine, paclitaxel, docetaxel, colchicine, actinomycin D, daunorubicin, bleomycin, L-asparaginase, cisplatin, carboplatin, oxaliplatin, prednisone, dexamethasone, amino glutethimide, formestane, anastrozole, hydroxyprogesterone caproate, medroxyprogesterone, tamoxifen, amsacrine, mitoxantrone, topotecan, irinotecan, camptothecin, axtinib, bosutinib, cediranib, dasatinib, erlotinib, gefitinib, imatinib, lapatinib, lestaurtinib, nilotinib, semaxanib, sunitinib, vandetanib, vatalanib, anti-Her2 antibodies, interleukin-2, GM-CSF, anti-CTLA-4 antibodies, rituximab, anti-CD33 antibodies, MGCD0103, vorinostat, 17-AAG, thalidomide, lenalidomide, rapamycin, CCI-779, sorafenib, doxorubicine, gemcitabine, melphalan, bortezomib, NPI052, gemtuzumab, alemtuzumab, ibritumomab tiuxaetan, tositumomab, iodine-131 tositumomab, trastuzumab, bevacizumab, rituximab, and anti-TRAIL death receptor antibodies.

In another embodiment of a method for treating or managing a proliferative disorder in a subject, a subject in need thereof is administered a therapeutically or prophylactically effective amount of a JAK inhibitor in combination with the administration of a therapeutically or prophylactically effective amount of one or more chemotherapeutic agents selected from paclitaxel, cyclophosphamide, 5-fluorouracil, cisplatin, carboplatin, methotrexate and imatinib.

In another embodiment, this invention also provides a method of treating or preventing a JAK kinase-mediated disease, in which the JAK-mediated disease is essential thrombocythemia (ET), polycythemia vera (PV) or primary myelofibrosis (PMF), comprising administering to a subject an amount of compound effective to treat or prevent the JAK kinase-mediated disease wherein the compound is selected from the compounds of the invention, or pharmaceutically acceptable salts thereof, as described herein. For example, a PV patient could take one or more of the JAK selective compounds described herein to alleviate certain symptoms associated with the disease such as splenomegaly and hepatomegaly as well as decrease his dependence on phlebotomy as a treatment option.

In another embodiment, this invention also provides a method of treating or preventing a JAK kinase-mediated disease, in which the JAK-mediated disease is essential thrombocythemia (ET), polycythemia vera (PV) or primary myelofibrosis (PMF), comprising administering to a subject an amount of compound effective to treat or prevent the JAK kinase-mediated disease wherein the compound is selected from the compounds of the invention, or pharmaceutically acceptable salts thereof, as described herein.

In another embodiment, this invention also provides a method of treating or preventing a JAK kinase-mediated non-classic myeloproliferative neoplasms (MPNs), such as atypical chronic myelogenous leukemia (aCML), chronic myelomonocytic leukemia (CMML), juvenile myelomonocytic leukemia (JMML), myelodysplastic syndrome (MDS), systemic mastocytosis and refractory anemia with ringed sideroblasts and associated with marked thrombocytosis (RARS-T), comprising administering to a subject an amount of compound effective to treat or prevent the JAK kinase-mediated disease wherein the compound is selected from the compounds of the invention, or pharmaceutically acceptable salts thereof, as described herein.

This invention also provides a method of treating or preventing a JAK kinase-mediated neoplasms (MPNs), such as acute myeloid leukemia (AML) and acute lymphoid leukemia (ALL) comprising administering to a subject an amount of compound effective to treat or prevent the JAK kinase-mediated disease wherein the compound is selected from the compounds of the invention, or pharmaceutically acceptable salts thereof, as described herein.

In a specific embodiment, the compounds can be used to treat and/or prevent rejection in organ and/or tissue transplant recipients (i.e., treat and/or prevent allograft rejection). Allografts can be rejected through either a cell-mediated or humoral immune reaction of the recipient against transplant (histocompatibility) antigens present on the membranes of the donor's cells. The strongest antigens are governed by a complex of genetic loci termed human leukocyte group A (HLA) antigens. Together with the ABO blood groups antigens, they are the chief transplantation antigens detectable in humans.

Rejection following transplantation can generally be broken into three categories: hyperacute, occurring hours to days following transplantation; acute, occurring days to months following transplantation; and chronic, occurring months to years following transplantation.

Hyperacute rejection is caused mainly by the production of host antibodies that attack the graft tissue. In a hyperacute rejection reaction, antibodies are observed in the transplant vascular very soon after transplantation. Shortly thereafter, vascular clotting occurs, leading to ischemia, eventual necrosis and death. The graft infarction is unresponsive to known immunosuppressive therapies. Because HLA antigens can be identified in vitro, pre-transplant screening is used to significantly reduce hyperacute rejection. As a consequence of this screening, hyperacute rejection is relatively uncommon today.

Acute rejection is thought to be mediated by the accumulation of antigen specific cells in the graft tissue. The T-cell-mediated immune reaction against these antigens (i.e., HVGR or GVHR) is the principle mechanism of acute rejection. Accumulation of these cells leads to damage of the graft tissue. It is believed that both CD4+ helper T-cells and CD8+ cytotoxic T-cells are involved in the process and that the antigen is presented by donor and host dendritic cells. The CD4+ helper T-cells help recruit other effector cells, such as macrophages and eosinophils, to the graft. Accessing T-cell activation signal transduction cascades (for example, CD28, CD40L, and CD2 cascades) are also involved.

The cell-mediated acute rejection can be reversed in many cases by intensifying immunotherapy. After successful reversal, severely damaged elements of the graft heal by fibrosis and the remainder of the graft appears normal. After resolution of acute rejection, dosages of immunosuppressive drugs can be reduced to very low levels.

Chronic rejection, which is a particular problem in renal transplants, often progresses insidiously despite increased immunosuppressive therapy. It is thought to be due, in large part, to cell-mediated Type IV hypersensitivity. The pathologic profile differs from that of acute rejection. The arterial endothelium is primarily involved with extensive proliferation that may gradually occlude the vessel lumen, leading to ischemia, fibrosis, a thickened intima, and atherosclerotic changes. Chronic rejection is mainly due to a progressive obliteration of graft vasculature and resembles a slow, vasculitis process.

In Type IV hypersensitivity, CD8 cytotoxic T-cells and CD4 helper T cells recognize either intracellular or extracellular synthesized antigen when it is complexed, respectively, with either Class I or Class II MHC molecules. Macrophages function as antigen-presenting cells and release IL-1, which promotes proliferation of helper T-cells. Helper T-cells release interferon gamma and IL-2, which together regulate delayed hyperactivity reactions mediated by macrophage activation and immunity mediated by T cells. In the case of organ transplant, the cytotoxic T-cells destroy the graft cells on contact.

Since JAK kinases play a critical role in the activation of T-cells, the 2,4-pyrimidinediamines described herein can be used to treat and/or prevent many aspects of transplant rejection, and are particularly useful in the treatment and/or prevention of rejection reactions that are mediated, at least in part, by T-cells, such as HVGR or GVHR. The 2,4-pyrimidinediamines can also be used to treat and/or prevent chronic rejection in transplant recipients and, in particular, in renal transplant recipients. The compound can also be administered to a tissue or an organ prior to transplanting the tissue or organ in the transplant recipient.

In another embodiment, this invention provides a method of treating a T-cell mediated autoimmune disease, comprising administering to a patient suffering from such an autoimmune disease an amount of a compound effective to treat the autoimmune disease wherein the compound is selected from the compounds of the invention. In certain embodiments of the methods the autoimmune disease is multiple sclerosis (MS), psoriasis, or Sjogran's syndrome.

Therapy using the 2,4-pyrimidinediamines described herein can be applied alone, or it can be applied in combination with or adjunctive to other common immunosuppressive therapies, such as, for example, the following: mercaptopurine; corticosteroids such as prednisone; methylprednisolone and prednisolone; alkylating agents such as cyclophosphamide; calcineurin inhibitors such as cyclosporine, sirolimus, and tacrolimus; inhibitors of inosine monophosphate dehydrogenase (IMPDH) such as mycophenolate, mycophenolate mofetil, and azathioprine; and agents designed to suppress cellular immunity while leaving the recipient's humoral immunologic response intact, including various antibodies (for example, antilymphocyte globulin (ALG), antithymocyte globulin (ATG), monoclonal anti-T-cell antibodies (OKT3)) and irradiation. These various agents can be used in accordance with their standard or common dosages, as specified in the prescribing information accompanying commercially available forms of the drugs (see also: the prescribing information in the 2006 Edition of *The Physician's Desk Reference*), the disclosures of which are incorporated herein by reference. Azathioprine is currently available from Salix Pharmaceuticals, Inc., under the brand name AZASAN; mercaptopurine is currently available from Gate Pharmaceuticals, Inc., under the brand name PURINETHOL; prednisone and prednisolone are currently available from Roxane Laboratories, Inc.; Methyl prednisolone is currently available from Pfizer; sirolimus (rapamycin) is currently available from Wyeth-Ayerst under the brand name RAPAMUNE; tacrolimus is currently available from Fujisawa under the brand name PROGRAF; cyclosporine is current available from Novartis under the brand name SANDIMMUNE and from Abbott under the brand name GENGRAF; IMPDH inhibitors such as mycophenolate mofetil and mycophenolic acid are currently available from Roche under the brand name CELLCEPT and from Novartis under the brand name MYFORTIC; azathioprine is currently available from Glaxo Smith Kline under the brand name IMURAN; and antibodies are currently available from Ortho Biotech under the brand name ORTHOCLONE, from Novartis under the brand name SIMULECT (basiliximab), and from Roche under the brand name ZENAPAX (daclizumab).

In another embodiment, this invention provides a method of treating or preventing allograft transplant rejection in a transplant recipient, comprising administering to the transplant recipient an amount of a compound effective to treat or prevent the allograft transplant rejection wherein the compound is selected from the compounds of the invention, as described herein. In a further embodiment, the compound is administered to a tissue or an organ prior to transplanting the tissue or organ in the transplant recipient.

In another embodiment, this invention provides a method of treating or preventing allograft transplant rejection in a transplant recipient, in which the rejection is acute rejection, comprising administering to the transplant recipient an amount of a compound effective to treat or prevent the rejection, wherein the compound is selected from the compounds of the invention.

In another embodiment, this invention provides a method of treating or preventing allograft transplant rejection in a transplant recipient, in which the rejection is chronic rejection, comprising administering to the transplant recipient an amount of a compound effective to treat or prevent the rejection, wherein the compound is selected from the compounds of the invention.

In another embodiment, this invention provides a method of treating or preventing allograft transplant rejection in a transplant recipient, in which the rejection is mediated by HVGR or GVHR, comprising administering to the transplant recipient an amount of a compound effective to treat or prevent the rejection, wherein the compound is selected from the compounds of this invention, as described herein.

In another embodiment, this invention provides a method of treating or preventing allograft transplant rejection in a transplant recipient, in which the allograft transplant is selected from a kidney, a heart, a liver, and a lung, comprising administering to the transplant recipient an amount of a compound effective to treat or prevent the rejection, wherein the compound is selected from the compounds of this invention, as described herein.

In another embodiment, this invention provides a method of treating or preventing allograft transplant rejection in a transplant recipient, in which the allograft transplant is selected from a kidney, a heart, a liver, and a lung, comprising administering to the transplant recipient an amount of a compound effective to treat or prevent the rejection wherein the compound is selected from the compounds of the invention, as described herein, in which the compound is administered in combination with or adjunctively to another immunosuppressant.

In another embodiment, this invention provides a method of treating or preventing allograft transplant rejection in a transplant recipient, in which the allograft transplant is selected from a kidney, a heart, a liver, and a lung, comprising administering to the transplant recipient an amount of a compound effective to treat or prevent the rejection, wherein the compound is selected from the compounds of the invention, as described herein, in which the compound is administered in combination with or adjunctively to another immunosuppressant, in which the immunosuppressant is selected from cyclosporine, tacrolimus, sirolimus, an inhibitor of IMPDH, mycophenolate, mycophanolate mofetil, an anti-T-Cell antibody, and OKT3.

The 2,4-pyrimidinediamines described herein are cytokine moderators of IL-4 signaling. As a consequence, the 2,4-pyrimidinediamines could slow the response of Type I hypersensitivity reactions. Thus, in a specific embodiment, the 2,4-pyrimidinediamines could be used to treat such reactions and, therefore, the diseases associated with, mediated by, or caused by such hypersensitivity reactions (for example, allergies), prophylactically. For example, an allergy sufferer could take one or more of the JAK selective compounds described herein prior to expected exposure to allergens to delay the onset or progress of, or eliminate altogether, an allergic response.

When used to treat or prevent such diseases, the 2,4-pyrimidinediamines can be administered singly, as mixtures of one or more 4-heteroaryl-pyrimidine-2-amines, or in mixture or combination with other agents useful for treating such diseases and/or the symptoms associated with such diseases. The 2,4-pyrimidinediamines may also be administered in mixture or in combination with agents useful to treat other disorders or maladies, such as steroids, membrane stabilizers, 5-lipoxygenase (5LO) inhibitors, leukotriene synthesis and receptor inhibitors, inhibitors of IgE isotype switching or IgE synthesis, IgG isotype switching or IgG synthesis, β-agonists, tryptase inhibitors, aspirin, cyclooxygenase (COX) inhibitors, methotrexate, anti-TNF drugs, retuxin, PD4 inhibitors, p38 inhibitors, PDE4 inhibitors, and antihistamines, to name a few. The 2,4-pyrimidinediamines can be administered per se or as pharmaceutical compositions, comprising an active compound.

In another embodiment, this invention provides a method of treating or preventing a Type IV hypersensitivity reaction, comprising administering to a subject an amount of a compound effective to treat or prevent the hypersensitivity reaction, wherein the compound is selected from the compounds of this invention, as described herein.

In another embodiment, this invention provides a method of treating or preventing a Type IV hypersensitivity reaction, which is practical prophylactically, comprising administering to a subject an amount of a compound effective to treat or prevent the hypersensitivity reaction, wherein the compound is selected from the compounds of this invention, as described herein, and is administered prior to exposure to an allergen.

In one embodiment, this invention provides a method of inhibiting a signal transduction cascade in which JAK2 kinase plays a role, comprising contacting a cell expressing a receptor involved in such a signaling cascade with a compound, wherein the compound is selected from the compounds of this invention, as described herein.

In one embodiment, this invention provides a method of treating or preventing a JAK kinase-mediated disease, comprising administering to a subject an amount of compound effective to treat or prevent the JAK kinase-mediated disease, wherein the compound is selected from the compounds of this invention, as described herein.

In another embodiment, this invention provides a method of treating or preventing a JAK kinase-mediated disease, in which the JAK-mediated disease is HVGR or GVHR, comprising administering to a subject an amount of compound effective to treat or prevent the JAK kinase-mediated disease, wherein the compound is selected from the compounds of the invention, as described herein.

In another embodiment, this invention provides a method of treating or preventing a JAK kinase-mediated disease, in which the JAK-mediated disease is acute allograft rejection, comprising administering to a subject an amount of compound effective to treat or prevent the JAK kinase-mediated disease, wherein the compound is selected from the compounds of the invention, as described herein.

In another embodiment, this invention provides a method of treating or preventing a JAK kinase-mediated disease, in which the JAK-mediated disease is chronic allograft rejection, comprising administering to a subject an amount of compound effective to treat or prevent the JAK kinase-mediated disease, wherein the compound is selected from the compounds of the invention, as described herein.

Active compounds of the invention typically inhibit the JAK/Stat pathway. The activity of a specified compound as an inhibitor of a JAK kinase can be assessed in vitro or in vivo. In some embodiments, the activity of a specified compound can be tested in a cellular assay. Suitable assays include assays that determine inhibition of either the phosphorylation activity or ATPase activity of a JAK kinase. Thus, a compound is said to inhibit an activity of a JAK kinase if it inhibits the phosphorylation or ATPase activity of a JAK kinase with an $IC_{50}$ of about 20 μM or less.

"Cell proliferative disorder" refers to a disorder characterized by abnormal proliferation of cells. A proliferative disorder does not imply any limitation with respect to the rate of cell growth, but merely indicates loss of normal controls that affect growth and cell division. Thus, in some embodiments, cells of a proliferative disorder can have the same cell division rates as normal cells but do not respond to signals that limit such growth. Within the ambit of "cell proliferative disorder" is neoplasm or tumor, which is an abnormal growth of tissue. Cancer refers to any of various malignant neoplasms characterized by the proliferation of cells that have the capability to invade surrounding tissue and/or metastasize to new colonization sites.

"Hematopoietic neoplasm" refers to a cell proliferative disorder arising from cells of the hematopoietic lineage. Generally, hematopoiesis is the physiological process whereby undifferentiated cells or stem cells develop into various cells found in the peripheral blood. In the initial phase of development, hematopoietic stem cells, typically found in the bone marrow, undergo a series of cell divisions to form multipotent progenitor cells that commit to two main developmental pathways: the lymphoid lineage and the myeloid lineage. The committed progenitor cells of the myeloid lineage differentiate into three major sub-branches comprised of the erythroid, megakaryocyte, and granulocyte/monocyte developmental pathways. An additional pathway leads to formation of dendritic cells, which are involved in antigen presentation. The erythroid lineage gives rise to red blood cells while the megakaryocytic lineage gives rise to blood platelets. Committed cells of the granulocyte/monocyte lineage split into granulocyte or monocyte developmental pathways, the former pathway leading to formation of neutrophils, eosinophils, and basophils and the latter pathway giving rise to blood monocytes and macrophages.

Committed progenitor cells of the lymphoid lineage develop into the B cell pathway, T cell pathway, or the non-T/B cell pathway. Similar to the myeloid lineage, an additional lymphoid pathway appears to give rise to dendritic cells involved in antigen presentation. The B cell progenitor cell develops into a precursor B cell (pre-B), which differentiates into B cells responsible for producing immunoglobulins. Progenitor cells of the T cell lineage differentiate into precursor T cells (pre-T) that, based on the influence of certain cytokines, develop into cytotoxic or helper/suppressor T cells involved in cell mediated immunity. Non-T/B cell pathway leads to generation of natural killer (NK) cells. Neoplasms of hematopoietic cells can involve cells of any phase of hematopoiesis, including hematopoietic stem cells, multipotent progenitor cells, oligopotent committed progenitor cells, precursor cells, and mature differentiated cells. The categories of hematopoietic neoplasms can generally follow the descriptions and diagnostic criteria employed by those of skill in the art (see, e.g., International Classification of Disease and Related Health Problems (ICD 10), World Health Organization (2003)). Hematopoietic neoplasms can also be characterized based on the molecular features, such as cell surface markers and gene expression profiles, cell phenotype exhibited by the aberrant cells, and/or chromosomal aberrations (e.g., deletions, translocations, insertions, etc.) characteristic of certain hematopoietic neoplasms, such as the Philadelphia chromosome found in chronic myelogenous leukemia. Other classifications include National Cancer Institute Working Formulation (Cancer, 1982, 49:2112-2135) and Revised European-American Lymphoma Classification (REAL).

"Lymphoid neoplasm" refers a proliferative disorder involving cells of the lymphoid lineage of hematopoiesis. Lymphoid neoplasms can arise from hematopoietic stem cells as well as lymphoid committed progenitor cells, precursor cells, and terminally differentiated cells. These neoplasms can be subdivided based on the phenotypic attributes of the aberrant cells or the differentiated state from which the abnormal cells arise. Subdivisions include, among others, B cell neoplasms, T cell neoplasms, NK cell neoplasms, and Hodgkin's lymphoma.

"Myeloid neoplasm" refers to proliferative disorder of cells of the myeloid lineage of hematopoiesis. Neoplasms can arise from hematopoietic stem cells, myeloid committed progenitor cells, precursor cells, and terminally differentiated cells. Myeloid neoplasms can be subdivided based on the phenotypic attributes of the aberrant cells or the differentiated state from which the abnormal cells arise. Subdivisions include, among others, myeloproliferative diseases, myelodysplastic/myeloproliferative diseases, myelodysplastic syndromes, acute myeloid leukemia, and acute biphenotypic leukemia.

Generally, cell proliferative disorders treatable with the compounds disclosed herein relate to any disorder characterized by aberrant cell proliferation. These include various tumors and cancers, benign or malignant, metastatic or non-metastatic. Specific properties of cancers, such as tissue invasiveness or metastasis, can be targeted using the methods described herein. Cell proliferative disorders include a variety of cancers, including, among others, breast cancer, ovarian cancer, renal cancer, gastrointestinal cancer, kidney cancer, bladder cancer, pancreatic cancer, lung squamous carcinoma, and adenocarcinoma.

Tumors that may be affected by certain drugs include tongue, mouth, pharynx, esophagus, stomach, small intestine, colon, rectum, anus, liver, gallbladder, pancreas, larynx, lung and bronchus, bones and joints including synovial sarcoma and osteosarcoma, melanomas including basal cell carcinoma, squamous carcinoma, breast, cervix, endometrium, ovary, vulva, vagina, prostate, testis, penis, urinary bladder, kidney and renal pelvis, ureter, eye, brain including glioma, glioblastoma, astrocytoma, neuroblastoma, medulloblastoma, and thyroid.

In some embodiments, the cell proliferative disorder treated is a hematopoietic neoplasm, which is aberrant growth of cells of the hematopoietic system. Hematopoietic malignancies can have its origins in pluripotent stem cells, multipotent progenitor cells, oligopotent committed progenitor cells, precursor cells, and terminally differentiated cells involved in hematopoiesis. Some hematological malignancies are believed to arise from hematopoietic stem cells, which have the ability for self renewal. For instance, cells capable of developing specific subtypes of acute myeloid leukemia (AML) upon transplantation display the cell surface markers of hematopoietic stem cells, implicating hematopoietic stem cells as the source of leukemic cells. Blast cells that do not have a cell marker characteristic of hematopoietic stem cells appear to be incapable of establishing tumors upon transplantation (Blaire et al., 1997, *Blood* 89:3104-3112). The stem cell origin of certain hematological malignancies also finds support in the observation that specific chromosomal abnormalities associated with particular types of leukemia can be found in normal cells of hematopoietic lineage as well as leukemic blast cells. For instance, the reciprocal translocation t(9q34; 22q11) associated with approximately 95% of chronic myelogenous leukemia appears to be present in cells of the myeloid, erythroid, and lymphoid lineage, suggesting that the chromosomal aberration originates in hematopoietic stem cells. A subgroup of cells in certain types of CML displays the cell marker phenotype of hematopoietic stem cells.

Although hematopoietic neoplasms often originate from stem cells, committed progenitor cells or more terminally differentiated cells of a developmental lineage can also be the source of some leukemias. For example, forced expression of the fusion protein Bcr/Abl (associated with chronic myelogenous leukemia) in common myeloid progenitor or granulocyte/macrophage progenitor cells produces a leukemic-like condition. Moreover, some chromosomal aberrations associated with subtypes of leukemia are not found in the cell population with a marker phenotype of hematopoietic stem cells, but are found in a cell population displaying markers of a more differentiated state of the hematopoietic pathway (Turhan et al., 1995, *Blood* 85:2154-2161). Thus, while committed progenitor cells and other differentiated cells may have only a limited potential for cell division, leukemic cells may have acquired the ability to grow unregulated, in some instances mimicking the self-renewal characteristics of hematopoietic stem cells (Passegue et al., *Proc. Natl. Acad. Sci. USA*, 2003, 100:11842-9).

In some embodiments, the hematopoietic neoplasm treated is a lymphoid neoplasm, where the abnormal cells are derived from and/or display the characteristic phenotype of cells of the lymphoid lineage. Lymphoid neoplasms can be subdivided into B-cell neoplasms, T and NK-cell neoplasms, and Hodgkin's lymphoma. B-cell neoplasms can be further subdivided into precursor B-cell neoplasm and mature/peripheral B-cell neoplasm. Exemplary B-cell neoplasms are precursor B-lymphoblastic leukemia/lymphoma (precursor B-cell acute lymphoblastic leukemia) while exemplary mature/peripheral B-cell neoplasms are B-cell chronic lymphocytic leukemia/small lymphocytic lymphoma, B-cell prolymphocytic leukemia, lymphoplasmacytic lymphoma, splenic marginal zone B-cell lymphoma, hairy cell leukemia, plasma cell myeloma/plasmacytoma, extranodal marginal zone B-cell lymphoma of MALT type, nodal marginal zone B-cell lymphoma, follicular lymphoma, mantle-cell lymphoma, diffuse large B-cell lymphoma, mediastinal large B-cell lymphoma, primary effusion lymphoma, and Burkitt's lymphoma/Burkitt cell leukemia. T-cell and Nk-cell neoplasms are further subdivided into precursor T-cell neoplasm and mature (peripheral) T-cell neoplasms. Exemplary precursor T-cell neoplasm is precursor T-lymphoblastic lymphoma/leukemia (precursor T-cell acute lymphoblastic leukemia) while exemplary mature (peripheral) T-cell neoplasms are T-cell prolymphocytic leukemia T-cell granular lymphocytic leukemia, aggressive NK-cell leukemia, adult T-cell lymphoma/leukemia (HTLV-1), extranodal NK/T-cell lymphoma, nasal type, enteropathy-type T-cell lymphoma, hepatosplenic gamma-delta T-cell lymphoma, subcutaneous panniculitis-like T-cell lymphoma, Mycosis fungoides/Sezary syndrome, Anaplastic large-cell lymphoma, T/null cell, primary cutaneous type, Peripheral T-cell lymphoma, not otherwise characterized, Angioimmunoblastic T-cell lymphoma, Anaplastic large-cell lymphoma, T/null cell, primary systemic type. The third member of lymphoid neoplasms is Hodgkin's lymphoma, also referred to as Hodgkin's disease. Exemplary diagnosis of this class that can be treated with the compounds include, among others, nodular lymphocyte-predominant Hodgkin's lymphoma, and various classical forms of Hodgkin's disease, exemplary members of which are Nodular sclerosis Hodgkin's lymphoma (grades 1 and 2), Lymphocyte-rich classical Hodgkin's lymphoma, Mixed cellularity Hodgkin's lymphoma, and Lymphocyte depletion Hodgkin's lymphoma. In various embodiments, any of the lymphoid neoplasms that are associated with aberrant JAK activity can be treated with the JAK inhibitory compounds.

In some embodiments, the hematopoietic neoplasm treated is a myeloid neoplasm. This group comprises a large class of cell proliferative disorders involving or displaying the characteristic phenotype of the cells of the myeloid lineage. Myeloid neoplasms can be subdivided into myeloproliferative diseases, myelodysplastic/myeloproliferative diseases, myelodysplastic syndromes, and acute myeloid leukemias. Exemplary myeloproliferative diseases are chronic myelogenous leukemia (e.g., Philadelphia chromosome positive (t(9; 22)(qq34; q11)), chronic neutrophilic leukemia, chronic eosinophilic leukemia/hypereosinophilic syndrome, chronic idiopathic myelofibrosis, polycythemia vera, and essential thrombocythemia. Exemplary myelodysplastic/myeloproliferative diseases are chronic myelomonocytic leukemia, atypical chronic myelogenous leukemia, and juvenile myelomonocytic leukemia. Exemplary myelodysplastic syndromes are refractory anemia, with ringed sideroblasts and without ringed sideroblasts, refractory cytopenia (myelodysplastic syndrome) with multilineage dysplasia, refractory anemia (myelodysplastic syndrome) with excess blasts, 5q-syndrome, and myelodysplastic syndrome. In various embodiments, any of the myeloid neoplasms that are associated with aberrant JAK activity can be treated with the JAK inhibitory compounds.

In some embodiments, the JAK inhibitory compounds can be used to treat Acute myeloid leukemias (AML), which represent a large class of myeloid neoplasms having its own subdivision of disorders. These subdivisions include, among others, AMLs with recurrent cytogenetic translocations, AML with multilineage dysplasia, and other AML not otherwise categorized. Exemplary AMLs with recurrent cytogenetic translocations include, among others, AML with t(8; 21)(q22; q22), AML1(CBF-alpha)/ETO, Acute promyelocytic leukemia (AML with t(15; 17)(q22; q11-12) and variants, PML/RAR-alpha), AML with abnormal bone marrow eosinophils (inv(16)(p13q22) or t(16; 16)(p13; q11), CBFb/MYH11X), and AML with 11q23 (MLL) abnormalities. Exemplary AML with multilineage dysplasia are those that are associated with or without prior myelodysplastic syndrome. Other acute myeloid leukemias not classified within any definable group include, AML minimally differentiated, AML without maturation, AML with maturation, Acute myelomonocytic leukemia, Acute monocytic leukemia, Acute erythroid leukemia, Acute megakaryocytic leukemia, Acute basophilic leukemia, and Acute panmyelosis with myelofibrosis.

Animal models useful for testing the efficacy of compounds to treat or prevent the various diseases or conditions described above are well known in the art. Suitable animal models of polycythemia vera, essential thrombocythemia and primary myelofibrosis are described in Shimoda, (2008) *Leukemia* 22(1):87-95, Lacout, (2006) *Blood* 108(5):1652-60, Wernig, (2006) *Blood* 107(11):4274-81

In one embodiment, this invention provides a method of treating or preventing a JAK kinase-mediated disease, comprising administering to a subject an amount of a compound wherein the compound is selected from the compounds of this invention, effective to treat or prevent the JAK kinase-mediated disease, wherein the JAK kinase-mediated disease is a cell proliferative disorder. In another embodiment, the cell proliferative disorder is selected from the group consisting of hematopoietic neoplasm, lymphoid neoplasm, and myeloid neoplasm. In another embodiment, the cell proliferative disorder is selected from the group consisting of breast cancer, ovarian cancer, renal cancer, gastrointestinal cancer, kidney cancer, bladder cancer, pancreatic cancer, lung squamous carcinoma, and adenocarcinoma.

Pharmaceutical Compositions

Pharmaceutical compositions comprising the 2,4-pyrimidinediamines described herein (or tautomers, N-oxides, salts thereof) can be manufactured by means of conventional mixing, dissolving, granulating, dragee-making levigating, emulsifying, encapsulating, entrapping, or lyophilization processes. The compositions can be formulated in conventional manner using one or more physiologically acceptable carriers, diluents, excipients, or auxiliaries which facilitate processing of the active compounds into preparations which can be used pharmaceutically.

The 2,4-pyrimidinediamine compound can be formulated in the pharmaceutical compositions per se, or in the form of a hydrate, solvate, N-oxide, or pharmaceutically acceptable salt, as described herein. Typically, such salts are more soluble in aqueous solutions than the corresponding free acids and bases, but salts having lower solubility than the corresponding free acids and bases may also be formed.

In one embodiment, this invention provides a pharmaceutical formulation comprising a compound selected from the compounds of the invention, as described herein, and at least one pharmaceutically acceptable excipient, diluent, preservative, stabilizer, or mixture thereof.

In another embodiment, the methods can be practiced as a therapeutic approach towards the treatment of the conditions described herein. Thus, in a specific embodiment, the 2,4-pyrimidinediamines (and the various forms described herein, including pharmaceutical formulations comprising the compounds (in the various forms)) can be used to treat the conditions described herein in animal subjects, including humans. The methods generally comprise administering to the subject an amount of a compound of the invention, or a salt, hydrate, or N-oxide thereof, effective to treat the condition. In one embodiment, the subject is a non-human mammal, including, but not limited to, bovine, horse, feline, canine, rodent, or primate. In another embodiment, the subject is a human.

The compounds can be provided in a variety of formulations and dosages. The compounds can be provided in a pharmaceutically acceptable form, including where the compound can be formulated in the pharmaceutical compositions per se, or in the form of a hydrate, solvate, N-oxide, or pharmaceutically acceptable salt, as described herein. Typically, such salts are more soluble in aqueous solutions than the corresponding free acids and bases, but salts having lower solubility than the corresponding free acids and bases may also be formed.

In one embodiment, the compounds are provided as non-toxic pharmaceutically acceptable salts, as noted previously. Suitable pharmaceutically acceptable salts of the compounds of this invention include acid addition salts such as those formed with hydrochloric acid, fumaric acid, p-toluenesulphonic acid, maleic acid, succinic acid, acetic acid, citric acid, tartaric acid, carbonic acid, or phosphoric acid. Salts of amine groups may also comprise quaternary ammonium salts in which the amino nitrogen atom carries a suitable organic group such as an alkyl, alkenyl, alkynyl, or substituted alkyl moiety. Furthermore, where the compounds of the invention carry an acidic moiety, suitable pharmaceutically acceptable salts thereof may include metal salts such as alkali metal salts, e.g., sodium or potassium salts; and alkaline earth metal salts, e.g., calcium or magnesium salts.

The pharmaceutically acceptable salts of the present invention can be formed by conventional means, such as by reacting the free base form of the product with one or more equivalents of the appropriate acid in a solvent or medium in which the salt is insoluble or in a solvent such as water which is removed in vacuo, by freeze drying, or by exchanging the anions of an existing salt for another anion on a suitable ion exchange resin.

The present invention includes within its scope solvates of the 2,4-pyrimidinediamines and salts thereof, for example, hydrates.

The 2,4-pyrimidinediamines may have one or more asymmetric centers and may accordingly exist both as enantiomers and as diastereoisomers. It is to be understood that all such isomers and mixtures thereof are encompassed within the scope of the present invention.

The 2,4-pyrimidinediamines can be administered by oral, parenteral (e.g., intramuscular, intraperitoneal, intravenous, ICV, intracisternal injection or infusion, subcutaneous injection, or implant), by inhalation spray nasal, vaginal, rectal, sublingual, urethral (e.g., urethral suppository) or topical routes of administration (e.g., gel, ointment, cream, aerosol, etc.) and can be formulated, alone or together, in suitable dosage unit formulations containing conventional non-toxic pharmaceutically acceptable carriers, adjuvants, excipients, and vehicles appropriate for each route of administration. In addition to the treatment of warm-blooded animals such as mice, rats, horses, cattle, sheep, dogs, cats, and monkeys, the compounds of the invention can be effective in humans.

The pharmaceutical compositions for the administration of the 2,4-pyrimidinediamines can be conveniently presented in dosage unit form and can be prepared by any of the methods well known in the art of pharmacy. The pharmaceutical compositions can be, for example, prepared by uniformly and intimately bringing the active ingredient into association with a liquid carrier, a finely divided solid carrier or both, and then, if necessary, shaping the product into the desired formulation. In the pharmaceutical composition the active object compound is included in an amount sufficient to produce the desired therapeutic effect. For example, pharmaceutical compositions of the invention may take a form suitable for virtually any mode of administration, including, for example, topical, ocular, oral, buccal, systemic, nasal, injection, transdermal, rectal, and vaginal, or a form suitable for administration by inhalation or insufflation.

For topical administration, the JAK-selective compound(s) can be formulated as solutions, gels, ointments, creams, suspensions, etc., as is well-known in the art.

Systemic formulations include those designed for administration by injection (e.g., subcutaneous, intravenous, intramuscular, intrathecal, or intraperitoneal injection) as well as those designed for transdermal, transmucosal, oral, or pulmonary administration.

Useful injectable preparations include sterile suspensions, solutions, or emulsions of the active compound(s) in aqueous or oily vehicles. The compositions may also contain formulating agents, such as suspending, stabilizing, and/or dispersing agents. The formulations for injection can be presented in unit dosage form, e.g., in ampules or in multidose containers, and may contain added preservatives.

Alternatively, the injectable formulation can be provided in powder form for reconstitution with a suitable vehicle, including but not limited to sterile pyrogen free water, buffer, and dextrose solution, before use. To this end, the active compound(s) can be dried by any art-known technique, such as lyophilization, and reconstituted prior to use.

For transmucosal administration, penetrants appropriate to the barrier to be permeated are used in the formulation. Such penetrants are known in the art.

For oral administration, the pharmaceutical compositions may take the form of, for example, lozenges, tablets, or capsules prepared by conventional means with pharmaceutically acceptable excipients such as binding agents (e.g., pregelatinised maize starch, polyvinylpyrrolidone, or hydroxypropyl methylcellulose); fillers (e.g., lactose, microcrystalline cellulose, or calcium hydrogen phosphate); lubricants (e.g., magnesium stearate, talc, or silica); disintegrants (e.g., potato starch or sodium starch glycolate); or wetting agents (e.g., sodium lauryl sulfate). The tablets can be coated by methods well known in the art with, for example, sugars, films, or enteric coatings. Additionally, the pharmaceutical compositions containing the 2,4-substituted pyrmidinediamine as active ingredient in a form suitable for oral use may also include, for example, troches, lozenges, aqueous, or oily suspensions, dispersible powders or granules, emulsions, hard or soft capsules, or syrups or elixirs. Compositions intended for oral use can be prepared according to any method known to the art for the manufacture of pharmaceutical compositions, and such compositions may contain one or more agents selected from the group consisting of sweetening agents, flavoring agents, coloring agents, and preserving agents in order to provide pharmaceutically elegant and palatable preparations. Tablets contain the active ingredient (including drug) in admixture with non-toxic pharmaceutically acceptable excipients which are suitable for the manufacture of tablets. These excipients can be for example, inert diluents, such as calcium carbonate, sodium carbonate, lactose, calcium phosphate or sodium phosphate; granulating and disintegrating agents (e.g., corn starch or alginic acid); binding agents (e.g. starch, gelatin, or acacia); and lubricating agents (e.g., magnesium stearate, stearic acid, or talc). The tablets can be left uncoated or they can be coated by known techniques to delay disintegration and absorption in the gastrointestinal tract and thereby provide a sustained action over a longer period. For example, a time delay material such as glyceryl monostearate or glyceryl distearate can be employed. They may also be coated by the techniques described in the U.S. Pat. Nos. 4,256,108; 4,166,452; and 4,265,874 to form osmotic therapeutic tablets for control release. The pharmaceutical compositions of the invention may also be in the form of oil-in-water emulsions.

Liquid preparations for oral administration may take the form of, for example, elixirs, solutions, syrups, or suspensions, or they can be presented as a dry product for constitution with water or other suitable vehicle before use. Such liquid preparations can be prepared by conventional means with pharmaceutically acceptable additives such as suspending agents (e.g., sorbitol syrup, cellulose derivatives, or hydrogenated edible fats); emulsifying agents (e.g., lecithin, or acacia); non-aqueous vehicles (e.g., almond oil, oily esters, ethyl alcohol, Cremophore™, or fractionated vegetable oils); and preservatives (e.g., methyl or propyl-p-hydroxybenzoates or sorbic acid). The preparations may also contain buffer salts, preservatives, flavoring, coloring, and sweetening agents as appropriate.

Preparations for oral administration can be suitably formulated to give controlled release of the active compound, as is well known.

For buccal administration, the compositions may take the form of tablets or lozenges formulated in the conventional manner.

For rectal and vaginal routes of administration, the active compound(s) can be formulated as solutions (for retention enemas), suppositories, or ointments containing conventional suppository bases such as cocoa butter or other glycerides.

For nasal administration or administration by inhalation or insufflation, the active compound(s) can be conveniently delivered in the form of an aerosol spray from pressurized packs or a nebulizer with the use of a suitable propellant (e.g., dichlorodifluoromethane, trichlorofluoromethane, dichlorotetrafluoroethane, fluorocarbons, carbon dioxide, or other suitable gas). In the case of a pressurized aerosol, the dosage unit can be determined by providing a valve to deliver a metered amount. Capsules and cartridges for use in an inhaler or insufflator (for example, capsules and cartridges comprised of gelatin) can be formulated containing a powder mix of the compound and a suitable powder base such as lactose or starch.

The pharmaceutical compositions can be in the form of a sterile injectable aqueous or oleaginous suspension. This suspension can be formulated according to the known art using those suitable dispersing or wetting agents and suspending agents which have been mentioned above. The sterile injectable preparation may also be a sterile injectable solution or suspension in a non-toxic parenterally-acceptable diluent or solvent. Among the acceptable vehicles and solvents that can be employed are water, Ringer's solution, and isotonic sodium chloride solution. The 2,4-pyrimidinediamines may also be administered in the form of suppositories for rectal or urethral administration of the drug. In particular embodiments, the compounds can be formulated as urethral suppositories, for example, for use in the treatment of fertility conditions, particularly in males (e.g., for the treatment of testicular dysfunction).

According to the invention, 2,4-pyrimidinediamines can be used for manufacturing a composition or medicament, including medicaments suitable for rectal or urethral administration. The invention also relates to methods for manufacturing compositions including 2,4-pyrimidinediamines in a form that is suitable for urethral or rectal administration, including suppositories.

For topical use, creams, ointments, jellies, gels, solutions, suspensions, etc., containing the 2,4-pyrimidinediamines can be employed. In certain embodiments, the 2,4-pyrimidinediamines can be formulated for topical administration with polyethylene glycol (PEG). These formulations may optionally comprise additional pharmaceutically acceptable ingredients such as diluents, stabilizers, and/or adjuvants. In particular embodiments, the topical formulations are formulated for the treatment of allergic conditions and/or skin conditions including psoriasis, contact dermatitis, and atopic dermatitis, among others described herein.

According to the invention, 2,4-pyrimidinediamines can be used for manufacturing a composition or medicament, including medicaments suitable for topical administration. The invention also relates to methods for manufacturing compositions including 2,4-pyrimidinediamines in a form that is suitable for topical administration.

According to the present invention, 2,4-pyrimidinediamines can also be delivered by any of a variety of inhalation devices and methods known in the art, including, for example: U.S. Pat. No. 6,241,969; U.S. Pat. No. 6,060,069; U.S. Pat. No. 6,238,647; U.S. Pat. No 6,335,316; U.S. Pat. No. 5,364,838; U.S. Pat. No. 5,672,581; WO96/32149; WO95/24183; U.S. Pat. No. 5,654,007; U.S. Pat. No. 5,404,871; U.S. Pat. No. 5,672,581; U.S. Pat. No. 5,743,250; U.S. Pat. No. 5,419,315; U.S. Pat. No. 5,558,085; WO98/33480; U.S. Pat. No. 5,364,833; U.S. Pat. No. 5,320,094; U.S. Pat. No. 5,780,014; U.S. Pat. Nos. 5,658,878; 5,518,998; 5,506,203; U.S. Pat. No. 5,661,130; U.S. Pat. No. 5,655,523; U.S. Pat. No. 5,645,051; U.S. Pat. No. 5,622,166; U.S. Pat. No. 5,577,497; U.S. Pat. No. 5,492,112; U.S. Pat. No. 5,327,883; U.S. Pat. No. 5,277,195; U.S. Pat. App. No. 20010041190; U.S. Pat. App. No. 20020006901; and U.S. Pat. App. No. 20020034477.

Included among the devices which can be used to administer particular examples of the 2,4-pyrimidinediamines are those well-known in the art, such as metered dose inhalers, liquid nebulizers, dry powder inhalers, sprayers, thermal vaporizers, and the like. Other suitable technology for administration of particular 2,4-pyrimidinediamines includes electrohydrodynamic aerosolizers.

In addition, the inhalation device is preferably practical, in the sense of being easy to use, small enough to carry conveniently, capable of providing multiple doses, and durable. Some specific examples of commercially available inhalation devices are Turbohaler (Astra, Wilmington, Del.), Rotahaler (Glaxo, Research Triangle Park, N.C.), Diskus (Glaxo, Research Triangle Park, N.C.), the Ultravent nebulizer (Mallinckrodt), the Acorn II nebulizer (Marquest Medical Products, Totowa, N.J.) the Ventolin metered dose inhaler (Glaxo, Research Triangle Park, N.C.), and the like. In one embodiment, 2,4-pyrimidinediamines can be delivered by a dry powder inhaler or a sprayer.

As those skilled in the art will recognize, the formulation of 4-heteroaryl-pyrimidine-2-amines, the quantity of the formulation delivered, and the duration of administration of a single dose depend on the type of inhalation device employed as well as other factors. For some aerosol delivery systems, such as nebulizers, the frequency of administration and length of time for which the system is activated will depend mainly on the concentration of 2,4-pyrimidinediamines in the aerosol. For example, shorter periods of administration can be used at higher concentrations of 2,4-pyrimidinediamines in the nebulizer solution. Devices such as metered dose inhalers can produce higher aerosol concentrations and can be operated for shorter periods to deliver the desired amount of 2,4-pyrimidinediamines in some embodiments. Devices such as dry powder inhalers deliver active agent until a given charge of agent is expelled from the device. In this type of inhaler, the amount of 2,4-pyrimidinediamines in a given quantity of the powder determines the dose delivered in a single administration. The formulation of 2,4-pyrimidinediamine is selected to yield the desired particle size in the chosen inhalation device.

Formulations of 2,4-pyrimidinediamines for administration from a dry powder inhaler may typically include a finely divided dry powder containing 4-heteroaryl-pyrimidine-2-amines, but the powder can also include a bulking agent, buffer, carrier, excipient, another additive, or the like. Additives can be included in a dry powder formulation of 2,4-pyrimidinediamines, for example, to dilute the powder as required for delivery from the particular powder inhaler, to facilitate processing of the formulation, to provide advantageous powder properties to the formulation, to facilitate dispersion of the powder from the inhalation device, to stabilize to the formulation (e.g., antioxidants or buffers), to provide taste to the formulation, or the like. Typical additives include mono-, di-, and polysaccharides; sugar alcohols and other polyols, such as, for example, lactose, glucose, raffinose, melezitose, lactitol, maltitol, trehalose, sucrose, mannitol, starch, or combinations thereof; surfactants, such as sorbitols, diphosphatidyl choline, or lecithin; and the like.

The present invention also relates to a pharmaceutical composition including 2,4-pyrimidinediamines suitable for administration by inhalation. According to the invention, 2,4-pyrimidinediamines can be used for manufacturing a composition or medicament, including medicaments suitable for administration by inhalation. The invention also relates to methods for manufacturing compositions including 2,4-pyrimidinediamines in a form that is suitable for administration, including administration by inhalation. For example, a dry powder formulation can be manufactured in several ways, using conventional techniques, such as described in any of the publications mentioned above and incorporated expressly herein by reference, and, for example, Baker, et al., U.S. Pat. No. 5,700,904, the entire disclosure of which is incorporated expressly herein by reference. Particles in the size range appropriate for maximal deposition in the lower respiratory tract can be made by micronizing, milling, or the like. And a liquid formulation can be manufactured by dissolving the 2,4-pyrimidinediamines in a suitable solvent, such as water, at an appropriate pH, including buffers or other excipients.

Pharmaceutical compositions comprising the 2,4-pyrimidinediamines described herein can be manufactured by means of conventional mixing, dissolving, granulating, dragee-making levigating, emulsifying, encapsulating, entrapping, or lyophilization processes. The compositions can be formulated in conventional manner using one or more physiologically acceptable carriers, diluents, excipients, or auxiliaries which facilitate processing of the active compounds into preparations which can be used pharmaceutically.

For ocular administration, the 2,4-pyrimidinediamine compound(s) can be formulated as a solution, emulsion, suspension, etc., suitable for administration to the eye. A variety of vehicles suitable for administering compounds to the eye are known in the art. Specific non-limiting examples are described in U.S. Pat. No. 6,261,547; U.S. Pat. No. 6,197,934; U.S. Pat. No. 6,056,950; U.S. Pat. No. 5,800,807; U.S. Pat. No. 5,776,445; U.S. Pat. No. 5,698,219; U.S. Pat. No. 5,521,222; U.S. Pat. No. 5,403,841; U.S. Pat. No. 5,077,033; U.S. Pat. No. 4,882,150; and U.S. Pat. No. 4,738,851.

For prolonged delivery, the 2,4-pyrimidinediamine compound(s) can be formulated as a depot preparation for administration by implantation or intramuscular injection. The active ingredient can be formulated with suitable polymeric or hydrophobic materials (e.g., as an emulsion in an acceptable oil) or ion exchange resins, or as sparingly soluble derivatives (e.g., as a sparingly soluble salt). Alternatively, transdermal delivery systems manufactured as an adhesive disc or patch which slowly releases the active compound(s) for percutaneous absorption can be used. To this end, permeation enhancers can be used to facilitate transdermal penetration of the active compound(s). Suitable transdermal patches are described in, for example, U.S. Pat. No. 5,407,713; U.S. Pat. No. 5,352,456; U.S. Pat. No. 5,332,213; U.S. Pat. No. 5,336,168; U.S. Pat. No. 5,290,561; U.S. Pat. No. 5,254,346; U.S. Pat. No. 5,164,189; U.S. Pat. No. 5,163,899; U.S. Pat. No. 5,088,977; U.S. Pat. No. 5,087,240; U.S. Pat. No. 5,008,110; and U.S. Pat. No. 4,921,475.

Alternatively, other pharmaceutical delivery systems can be employed. Liposomes and emulsions are well-known examples of delivery vehicles that can be used to deliver active compound(s). Certain organic solvents such as dimethylsulfoxide (DMSO) may also be employed, although usually at the cost of greater toxicity.

The pharmaceutical compositions may, if desired, be presented in a pack or dispenser device which may contain one or more unit dosage forms containing the active compound(s). The pack may, for example, comprise metal or plastic foil, such as a blister pack. The pack or dispenser device can be accompanied by instructions for administration.

The 2,4-pyrimidinediamine compound(s) described herein, or compositions thereof, will generally be used in an amount effective to achieve the intended result, for example, in an amount effective to treat or prevent the particular condition being treated. The compound(s) can be administered therapeutically to achieve therapeutic benefit or prophylactically to achieve prophylactic benefit. By therapeutic benefit is meant eradication or amelioration of the underlying disorder being treated and/or eradication or amelioration of one or more of the symptoms associated with the underlying disorder such that the patient reports an improvement in feeling or condition, notwithstanding that the patient may still be afflicted with the underlying disorder. For example, administration of a compound to a patient suffering from an allergy provides therapeutic benefit not only when the underlying allergic response is eradicated or ameliorated, but also when the patient reports a decrease in the severity or duration of the symptoms associated with the allergy following exposure to the allergen. As another example, therapeutic benefit in the context of asthma includes an improvement in respiration following the onset of an asthmatic attack or a reduction in the frequency or severity of asthmatic episodes. As another specific example, therapeutic benefit in the context of transplantation rejection includes the ability to alleviate an acute rejection episode, such as, for example, HVGR or GVHR, or the ability to prolong the time period between onset of acute rejection episodes and/or onset of chronic rejection. Therapeutic benefit also includes halting or slowing the progression of the disease, regardless of whether improvement is realized.

The amount of compound administered will depend upon a variety of factors, including, for example, the particular condition being treated, the mode of administration, the severity of the condition being treated, the age and weight of the patient, the bioavailability of the particular active compound. Determination of an effective dosage is well within the capabilities of those skilled in the art.

As known by those of skill in the art, the preferred dosage of 2,4-pyrimidinediamines will also depend on the age, weight, general health, and severity of the condition of the individual being treated. Dosage may also need to be tailored to the sex of the individual and/or the lung capacity of the individual, where administered by inhalation. Dosage may also be tailored to individuals suffering from more than one condition or those individuals who have additional conditions which affect lung capacity and the ability to breathe normally, for example, emphysema, bronchitis, pneumonia, and respiratory infections. Dosage, and frequency of administration of the compounds, will also depend on whether the compounds are formulated for treatment of acute episodes of a condition or for the prophylactic treatment of a disorder. For example, acute episodes of allergic conditions, including allergy-related asthma, transplant rejection, etc. A skilled practitioner will be able to determine the optimal dose for a particular individual.

For prophylactic administration, the compound can be administered to a patient at risk of developing one of the previously described conditions. For example, if it is unknown whether a patient is allergic to a particular drug, the compound can be administered prior to administration of the drug to avoid or ameliorate an allergic response to the drug. Alternatively, prophylactic administration can be applied to avoid the onset of symptoms in a patient diagnosed with the underlying disorder. For example, a compound can be administered to an allergy sufferer prior to expected exposure to the allergen. Compounds may also be administered prophylactically to healthy individuals who are repeatedly exposed to agents known to one of the above-described maladies to prevent the onset of the disorder. For example, a compound can be administered to a healthy individual who is repeatedly exposed to an allergen known to induce allergies, such as latex, in an effort to prevent the individual from developing an allergy. Alternatively, a compound can be administered to a patient suffering from asthma prior to partaking in activities which trigger asthma attacks to lessen the severity of, or avoid altogether, an asthmatic episode.

In the context of transplant rejection, the compound can be administered while the patient is not having an acute rejection reaction to avoid the onset of rejection and/or prior to the appearance of clinical indications of chronic rejection. The compound can be administered systemically to the patient as well as administered to the tissue or organ prior to transplanting the tissue or organ in the patient.

The amount of compound administered will depend upon a variety of factors, including, for example, the particular indication being treated, the mode of administration, whether the desired benefit is prophylactic or therapeutic, the severity of the indication being treated and the age and weight of the patient, and the bioavailability of the particular active compound. Determination of an effective dosage is well within the capabilities of those skilled in the art.

Effective dosages can be estimated initially from in vitro assays. For example, an initial dosage for use in animals can be formulated to achieve a circulating blood or serum concentration of active compound that is at or above an $IC_{50}$ of the particular compound as measured in as in vitro assay. Calculating dosages to achieve such circulating blood or serum concentrations taking into account the bioavailability of the particular compound is well within the capabilities of skilled artisans. For guidance, the reader is referred to Fingl & Woodbury, "General Principles," *In: Goodman and Gilman's The Pharmaceutical Basis of Therapeutics*, Chapter 1, pp. 1-46, latest edition, Pergamon Press, and the references cited therein.

Initial dosages can also be estimated from in vivo data, such as animal models. Animal models useful for testing the efficacy of compounds to treat or prevent the various diseases described above are well-known in the art. Suitable animal models of hypersensitivity or allergic reactions are described in Foster, (1995) *Allergy* 50(21Suppl):6-9, discussion 34-38 and Tumas et al., (2001), *J. Allergy Clin. Immunol.* 107(6): 1025-1033. Suitable animal models of allergic rhinitis are described in Szelenyi et al., (2000), *Arzneimittelforschung* 50(11):1037-42; Kawaguchi et al., (1994), *Clin. Exp. Allergy* 24(3):238-244 and Sugimoto et al., (2000), *Immunopharmacology* 48(1):1-7. Suitable animal models of allergic conjunctivitis are described in Carreras et al., (1993), *Br. J. Ophthalmol.* 77(8):509-514; Saiga et al., (1992), *Ophthalmic Res.* 24(1):45-50; and Kunert et al., (2001), *Invest. Ophthalmol. Vis. Sci.* 42(11):2483-2489. Suitable animal models of systemic mastocytosis are described in O'Keefe et al., (1987), *J. Vet. Intern. Med.* 1(2):75-80 and Bean-Knudsen et al., (1989), *Vet. Pathol.* 26(1):90-92. Suitable animal models of hyper IgE syndrome are described in Claman et al., (1990), *Clin. Immunol. Immunopathol.* 56(1):46-53. Suitable animal models of B-cell lymphoma are described in Hough et al., (1998), *Proc. Natl. Acad. Sci. USA* 95:13853-13858 and Hakim et al., (1996), *J. Immunol.* 157(12):5503-5511. Suitable animal models of atopic disorders such as atopic dermatitis, atopic eczema, and atopic asthma are described in Chan et al., (2001), *J. Invest. Dermatol.* 117(4):977-983 and Suto et al., (1999), *Int. Arch. Allergy Immunol.* 120(Suppl 1):70-75. Suitable animal models of transplant rejection, such as models of HVGR, are described in O'Shea et al., (2004), *Nature Reviews Drug Discovery* 3:555-564; Cetkovic-Curlje & Tibbles, (2004), *Current Pharmaceutical Design* 10:1767-1784; and Chengelian et al., (2003), *Science* 302:875-878. Ordinarily skilled artisans can routinely adapt such information to determine dosages suitable for human administration.

Dosage amounts will typically be in the range of from about 0.0001 or 0.001 or 0.01 mg/kg/day to about 100 mg/kg/day, but can be higher or lower, depending upon, among other factors, the activity of the compound, its bioavailability, the mode of administration, and various factors discussed above. Dosage amount and interval can be adjusted individually to provide plasma levels of the compound(s) which are sufficient to maintain therapeutic or prophylactic effect. For example, the compounds can be administered once per week, several times per week (e.g., every other day), once per day, or multiple times per day, depending upon, among other things, the mode of administration, the specific indication being treated, and the judgment of the prescribing physician. In cases of local administration or selective uptake, such as local topical administration, the effective local concentration of active compound(s) may not be related to plasma concentration. Skilled artisans will be able to optimize effective local dosages without undue experimentation.

Preferably, the compound(s) will provide therapeutic or prophylactic benefit without causing substantial toxicity. Toxicity of the compound(s) can be determined using standard pharmaceutical procedures. The dose ratio between toxic and therapeutic (or prophylactic) effect is the therapeutic index. Compounds(s) that exhibit high therapeutic indices are preferred.

Effective dosages can be estimated initially from in vitro activity and metabolism assays. For example, an initial dosage of a drug for use in animals can be formulated to achieve a circulating blood or serum concentration of the metabolite active compound that is at or above an $IC_{50}$ of the particular compound as measured in as in vitro assay, such as the in vitro CHMC or BMMC and other in vitro assays described in U.S. Patent Application Publication No. 2004/0029902, international application Serial No. PCT/US03/03022 filed Jan. 31, 2003 (WO 03/063794), U.S. application Ser. No. 10/631,029 filed Jul. 29, 2003, international application Serial No. PCT/US03/24087 (WO2004/014382), U.S. Patent Application Publication No. 2005/0234049, and international application Serial No. PCT/US2004/24716 (WO005/016893). Calculating dosages to achieve such circulating blood or serum concentrations, taking into account the bioavailability of the particular drug via the desired route of administration, is well within the capabilities of skilled artisans. For guidance, the reader is referred to Fingl & Woodbury, "General Principles," *In: Goodman and Gilman's The Pharmaceutical Basis of Therapeutics*, Chapter 1, pp. 1-46, latest edition, Pergamon Press, and the references cited therein.

Also provided are kits for administration of the 2,4-pyrimidinediamine, or pharmaceutical formulations comprising the compound that may include a dosage amount of at least one 2,4-pyrimidinediamine or a composition comprising at least one 2,4-pyrimidinediamine, as disclosed herein. Kits may further comprise suitable packaging and/or instructions for use of the compound. Kits may also comprise a means for the delivery of the at least one 2,4-pyrimidinediamine or compositions comprising at least one 2,4-pyrimidinediamine, such as an inhaler, spray dispenser (e.g., nasal spray), syringe for injection, or pressure pack for capsules, tables, suppositories, or other device as described herein.

Additionally, the compounds of the present invention can be assembled in the form of kits. The kit provides the compound and reagents to prepare a composition for administration. The composition can be in a dry or lyophilized form or in a solution, particularly a sterile solution. When the composition is in a dry form, the reagent may comprise a pharmaceutically acceptable diluent for preparing a liquid formulation. The kit may contain a device for administration or for dispensing the compositions, including, but not limited to, syringe, pipette, transdermal patch, or inhalant.

The kits may include other therapeutic compounds for use in conjunction with the compounds described herein. In one embodiment, the therapeutic agents are immunosuppressant or anti-allergan compounds. These compounds can be provided in a separate form or mixed with the compounds of the present invention.

The kits will include appropriate instructions for preparation and administration of the composition, side effects of the compositions, and any other relevant information. The instructions can be in any suitable format, including, but not limited to, printed matter, videotape, computer readable disk, or optical disc.

In one embodiment, this invention provides a kit comprising a compound selected from the compounds of the invention, packaging, and instructions for use.

In another embodiment, this invention provides a kit comprising the pharmaceutical formulation comprising a compound selected from the compounds of the invention and at least one pharmaceutically acceptable excipient, diluent, preservative, stabilizer, or mixture thereof, packaging, and instructions for use.

In another aspect of the invention, kits for treating an individual who suffers from or is susceptible to the conditions described herein are provided, comprising a container comprising a dosage amount of an 2,4-pyrimidinediamine or composition, as disclosed herein, and instructions for use. The container can be any of those known in the art and appropriate for storage and delivery of oral, intravenous, topical, rectal, urethral, or inhaled formulations.

Kits may also be provided that contain sufficient dosages of the 2,4-pyrimidinediamine or composition to provide effective treatment for an individual for an extended period, such as a week, 2 weeks, 3, weeks, 4 weeks, 6 weeks, or 8 weeks or more.

EXAMPLES

The invention is further understood by reference to the following examples, which are intended to be purely exemplary of the invention. The present invention is not limited in scope by the exemplified embodiments, which are intended as illustrations of single aspects of the invention only. Any methods that are functionally equivalent are within the scope of the invention. Various modifications of the invention in addition to those described herein will become apparent to those skilled in the art from the foregoing description and accompanying figures. Such modifications fall within the scope of the appended claims.

In the examples below as well as throughout the application, the following abbreviations have the following meanings. If not defined, the terms have their generally accepted meanings.

aq.=aqueous

TFA=trifluoroacetic acid

HPLC=high pressure liquid chromatography

DMSO=dimethylsulfoxide g=gram h=hour

HCl=hydrochloric acid

L=Liter

LC=liquid chromatography

MS=mass spectrum mL=milliliter m/e=mass to charge ratio rt=room temperature s=singlet d=doublet t=triplet dd=doublet of doublets $IC_{50}$=The concentration of an inhibitor that is required for 50% inhibition of an enzyme in vitro

Example 1

General Procedure for the SNAr Reaction of 2-chloropyrimidine and aminotricyclics

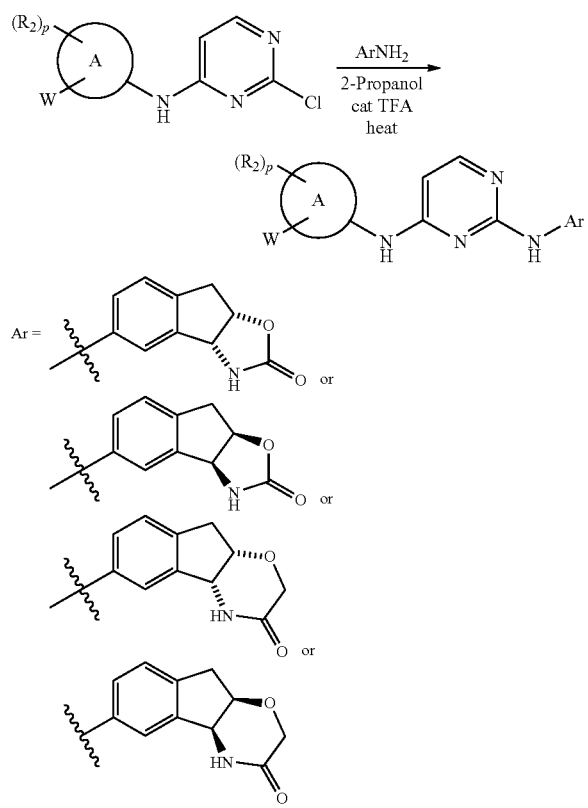

(4-Aminosubstituted)-2-chloropyrimidine (1 eq) and 5-amino-3,3a,8,8a-tetrahydroindeno[1,2-d]oxazol-2-one or 6-amino-2,3,4,4a,9a-tetrahydroindeno[2,1-b][1,4]oxazin-3(2H)-one (1.3-1.5 eq) in 2-propanol (2 mL per 40 mg) with cat. TFA (7% of 2-propanol) were heated either in a sealed tube (100° C.) or for in a microwave reactor (130° C.). After complete conversion of the 2-chloropyrimidine to the desired product, the reaction mixture was concentrated and purified by preparative HPLC. Neutralization of the product in the salt form with aq. $K_2CO_3$ was resulted a suspension. The aqueous suspension was filtered and the collected solid was dried to provide the desired product. (4-Aminosubstituted)-2-chloropyrimidine were obtained by using the general synthetic methods described in Schemes I-VII.

(3aR,8aS)-5-Amino-3,3a,8,8a-tetrahydroindeno[1,2-d]oxazol-2-one

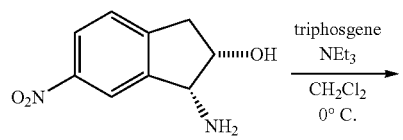

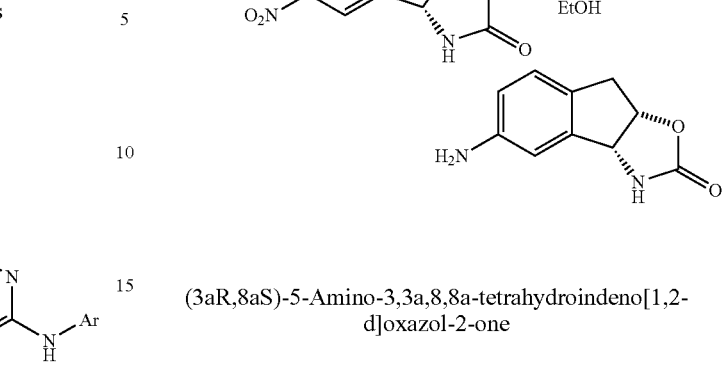

(3aR,8aS)-5-Amino-3,3a,8,8a-tetrahydroindeno[1,2-d]oxazol-2-one (3aR,8aS)-5-Nitro-3,3a,8,8a-tetrahydroindeno[1,2-d]oxazol-2-one (1.3 g, 5.45 mmol) was dissolved in EtOH (50 mL), transferred to par hydrogenation flask. Pd/C (450 mg) transferred to above flask and subjected to hydrogenation at 30 PSI for 2 h. Reaction mixture filtered through Celite and washed the filter cake with EtOH. Filtrate was concentrated and purified by silica gel column chromatography (50-100% EtOAc:hexanes) to provide (3aR,8aS)-5-amino-3,3a,8,8a-tetrahydroindeno[1,2-d]oxazol-2-one (720 mg, 69%) as a white solid. $^1$H NMR (DMSO-d6): δ 8.23 (s, 1H), 6.90 (d, 1H, J=8.2 Hz), 6.52-4.49 (m, 2H), 5.20 (app t, 1H, J=6.1 and 7.0 Hz), 5.04 (br s, 2H), 4.91 (d, 1H, J=7.0 Hz), 3.13 (dd, 1H, J=6.7 and 17.0 Hz), 2.89 (d, 1H, J=17.0 Hz). LCMS: purity: 99%; MS (m/e): 191 (MH$^+$).

(3aR,8aS)-5-Nitro-3,3a,8,8a-tetrahydroindeno[1,2-d]oxazol-2-one

Triethylamine (1.87 mL, 1.36 g. 13.44 mmol) was added to a stirring solution of (1R,2S)-cis-1-amino-6-nitroindan-2-ol (1.3 g, 6.70 mmol) and triphosgene (0.8 g, 2.69 mmol) in dry $CH_2Cl_2$ (20 mL) at 0° C. for 5 min. The reaction mixture was allowed to stir at 0° C. was for 1 h. After complete consumption of (1R,2S)-cis-1-amino-6-introindan-2-ol as monitored by LC/MS, reaction mixture was concentrated under reduced pressure. The crude residue was diluted with water (25 mL) and treated with aq. 2N HCl (10 mL) to provide a suspension. The suspension was then filtered, neutralized the collected solid with aq. NaHCO$_3$ and filtered again. The white solid obtained after filtration was dried under vacuum over $P_2O_5$ to provide (3aR,8aS)-5-nitro-3,3a,8,8a-tetrahydroindeno[1,2-d]oxazol-2-one (1.3 g, 88%). $^1$H NMR (DMSO-d6): δ 8.33 (s, 1H), 8.22 (s, 1H), 8.19 (dd, 1H, J=2.0 and 8.2 Hz), 7.58 (d, 1H, J=8.20 Hz), 5.37 (app t, 1H, J=6.1 and 7.0 Hz), 5.21 (d, 1H, J=7.0 Hz), 3.46 (dd, 1H, J=6.1 and 18.0 Hz), 3.24 (d, 1H, J=18.0 Hz). LCMS: purity: 98%; MS (m/e): 221 (MH$^+$).

(4aR,9aS)-6-Amino-2,3,4,4a,9a-tetrahydroindeno[2,1-b][1,4]oxazin-3(2H)-one

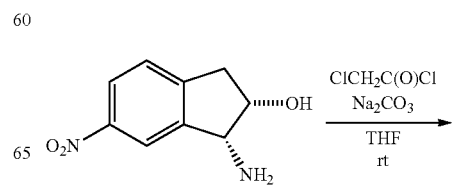

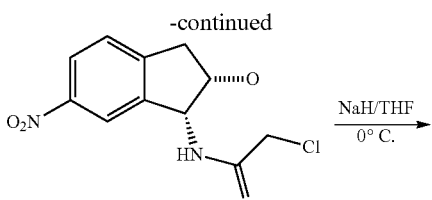

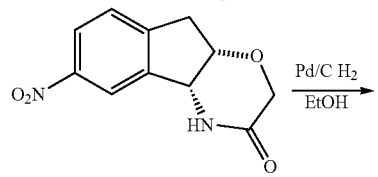

(4aR,9aS)-6-Nitro-2,3,4,4a,9a-tetrahydroindenoindeno[2,1-b][1,4]oxazin-3(2H)-one (350 mg, 1.49 mmol) was suspended in EtOH (50 mL), transferred to par hydrogenation flask. Pd/C (100 mg) transferred to above flask and subjected to hydrogenation at 40 PSI for 1 h. Reaction mixture filtered through Celite and washed the filter cake with EtOH. Upon concentration of the filtrate provided an off-white solid (274 mg, 90%). $^1$H NMR (DMSO-d6): δ 8.77 (s, 1H), 6.85 (d, 1H, J=8.2 Hz), 6.59 (s, 1H), 6.42 (d, 1H, J=8.2 Hz), 5.05 (br s, 2H), 4.49 (app t, 1H, H=4.4 Hz), 4.36 (t, 1H, J=4.4 Hz), 3.87 (AB qt, 2H, J=16.0 Hz), 2.95 (dd, 1, J=4.4 and 16.1 Hz), 2.66 (d, 1H, J=16.1 Hz). LCMS: purity: 98%; MS (m/e): 205 (MH$^+$).

(4aR,9aS)-6-Nitro-2,3,4,4a,9a-tetrahydroindeno[2,1-b][1,4]oxazin-3(2H)-one: 2-Chloro-N-[(1R,2S)-2-hydroxy-6-nitro-2,3-dihydro-1H-indeno-1-yl]acetamide (0.567 g, 2.1 mmol) in dry THF (10 mL) was added dropwise with a syringe to the pre-cooled stirring solution of NaH (60% dispersion in mineral oil, 0.16 g, 4.0 mmol) in THF (10 mL) at 0° C. Progress of the reaction was monitored by LC/MS and silica gel TLC (40% EtOAc/hexanes). Reaction mixture was quenched with water (5 mL) and aq. 2N HCl (5 mL) successively after 1.3 h. The quenched mixture was concentrated to provide a suspension, and filtered the suspension to provide the solid after drying. Purification of the crude solid by silica gel column chromatography furnished (4aR,9aS)-6-nitro-2,3,4,4a,9a-tetrahydroindeno[2,1-b][1,4]oxazin-3(2H)-one (390 mg, 79%). $^1$H NMR (DMSO-d6): δ 8.92 (s, 1H), 8.35 (s, 1H), 8.12 (d, 1H, J=8.5 Hz), 7.52 (d, 1H, J=8.5 Hz), 4.78 (app t, 1H, J=4.1 Hz), 4.55 (t, 1H, J=4.1 Hz), 3.94 (AB qt, 2H, J=13.8 Hz), 3.28 (dd, 1H, J=4.4 and 17.5 Hz), 2.98 (d, 1H, J=17.4 Hz). LCMS: purity: 98%; MS (m/e): 235 (MH$^+$).

2-Chloro-N-[(1R,2S)-2-hydroxy-6-nitro-2,3-dihydro-1H-indeno-1-yl]acetamide: Chloracetyl chloride (0.24 mL, 0.34 g. 3.01 mmol) was added to a stirring solution of (1R,2S)-cis-1-Amino-6-nitroindan-2-ol (0.5 g, 2.57 mmol) and Na$_2$CO$_3$ (0.8 g, 5.66 mmol) in dry THF (20 mL) at room temperature under N$_2$. The reaction mixture was stirred at room temperature after the addition of chloroacetyl chloride until the consumption of (1R,2S)-cis-1-Amino-6-nitroindan-2-ol. The reaction mixture was concentrated, diluted with water (30 mL) and extracted with EtOAc (2×75 mL). Combined organic layers were washed with water and brine successively. Usual workup and purification by silica gel chromatography furnished 2-chloro-N-[(1R,2S)-2-hydroxy-6-nitro-2,3-dihydro-1H-indeno-1-yl]acetamide as a viscous liquid (0.62 g, 89%). $^1$H NMR (DMSO-d6): δ 8.40 (d, 1H, J=8.5 Hz), 8.10 (dd, 1H, J=2.0 and 8.5 Hz), 7.91 (s, 1H), 7.54-7.50 (m, 1H), 5.37 (d, 1H, J=4.5 Hz), 5.26 (app qt, 1H, J=4.5 Hz), 4.50 (qt, 1H, J=4.4 Hz), 4.27 (AB qt, 2H, J=13.8 Hz), 3.17 (dd, 1H, J=4.4 and 17.4 Hz), 2.90 (d, 1H, J=17.4 Hz). LCMS: purity: 98%; MS (m/e): 271 (MH$^+$).

(1R,2S)-cis-1-amino-6-nitroindan-2-ol and (1S,2R)-cis-1-amino-6-nitroindan-2-ol are prepared by adopting the similar synthetic protocol that was used for the preparation of (1R,2R)-trans-1-Amino-6-nitroindan-2-ol (Kozhushkov, S. I., Yufit, D. S and Meijere, A. D. *Adv. Synth. Catal.* 2005, 347, 255-265).

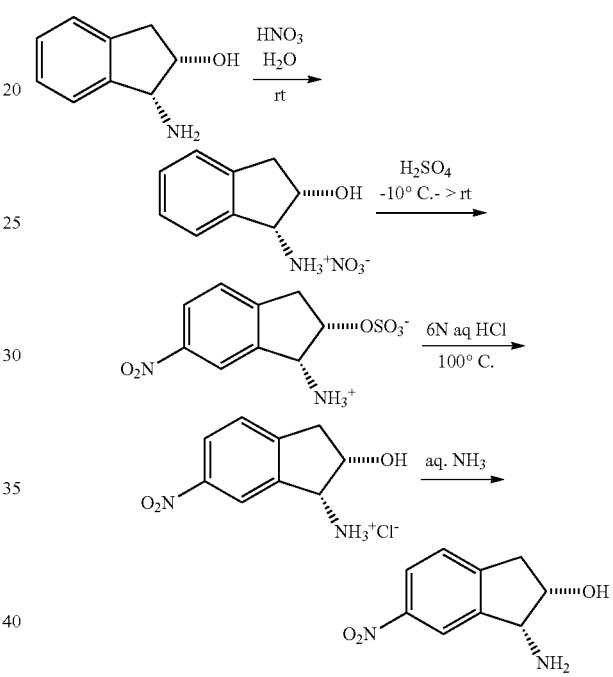

(1R,2S)-cis-1-Aminoindan-2-ol nitrate salt

Aq. Nitric acid (69%, 3.38 mL, 1 eq)), was added dropwise to a stirred suspension of (1R,2S)-cis-1-Aminoindan-2-ol (6.65 g, 44.57 mmol) in water (25 mL) for 20 min. Heterogeneous reaction mixture slowly turned to a clear solution. The reaction mixture was concentrated under reduce pressure without heating the contents above 35° C. The crude viscous residue was treated with Et$_2$O (100 mL) followed by the addition of water (0.5 mL) and stirred the contents to form a nice white crystalline solid. The solid formed collected by filtration and dried under vacuum over P$_2$O$_5$ to provide (1R,2S)-cis-1-Aminoindan-2-ol nitrate salt (9.2 g, 97%).

Sulfuric acid mono-[(1R,2S)-cis-1-amino-6-nitroindan-2-yl) ester

To vigorously stirring solution of conc. H$_2$SO$_4$ (40 mL) maintained at −15° C. with ice/salt mixture externally, (1R,2S)-cis-1-Aminoindan-2-ol nitrate salt (9.2 g, 43.35 mmol) was charged in portions over a period of 20 min. External temperature maintained all the time below −10 C during the process of addition of the salt and continued to stir the contents vigorously at −10° C. for 1 h after the addition of the salt and at 0° C. for 1 h. The clear viscous solution was the poured onto cracked ice. The resulting fine precipitate filtered, washed with ice-cold water and dried under vacuum over $P_2O_5$ for 24 h to give sulfuric acid mono-[(1R,2S)-cis-1-amino-6-nitroindan-2-yl) ester as colorless white powder (8.62 g, 72%).

(1R,2S)-cis-1-Amino-6-nitroindan-2-ol

Sulfuric acid mono-[(1R,2S)-cis-1-amino-6-nitroindan-2-yl) ester (8.68 g) and 6N aq. HCl (100 mL) were stirred and heated (external temperature 125° C.) in a single necked round-bottomed flask equipped with a reflux condenser. The heterogeneous mixture turned to homogeneous mixture after 1 h of heating. The reaction mixture was cooled in ice and the crystalline solid formed was filtered and dried over $P_2O_5$ under vacuum to provide the crystalline solid of (1R,2S)-cis-1-amino-6-introindan-2-ol.HCl. $^1$H NMR ($D_2O$): δ 8.17 (s, 1H), 8.13 (d, 1H, J=8.2 Hz), 7.44 (d, 1H, J=8.2 Hz), 4.75-4.71 (m, 2H), 3.26 (dd, 1H, J=4.5 and 17.8 Hz), 2.95 (dd, 1H, J=3.2 and 17.8 Hz). LCMS: purity: 99%; MS (m/e):195 (MH$^+$—HCl). Aqueous solution of (1R,2S)-cis-1-amino-6-nitroindan-2-ol.HCl was neutralized with aq. $NH_4OH$ and filtered the resultant solid precipitated. The solid collected was vacuum dried (4.28 g, 70%). $^1$H NMR (DMSO-d6): δ 8.13 (s, 1H), 8.03 (d, 1H, J=8.2 Hz), 7.44 (d, 1H, J=8.2 Hz), 4.90 (br s, 1H), 2.29 (d, 1H, J=4.7 Hz), 4.11 (d, 1H, J=4.7 Hz), 3.03 (dd, 1H, J=4.7 and 17.0 Hz), 2.83 (d, 1H, J=17.0 Hz), 1.98 (br s, 2H). LCMS: purity: 99%; MS (m/e): 195 (MH$^+$).

The following examples were prepared in analogous manner to the above example or by using methods described herein or by using methods known to one of skill in the art.

1: 5-Chloro-N4-[4-[2-[N-(cyclopropylsulfonyl)amino]ethyl]phenyl]-N2-[(3aR,8aS)-2-oxo-3,3a,8,8a-tetrahydro-2H-indeno[1,2-d]oxazol-5-yl]-2,4-pyrimidinediamine LCMS: purity: 100%; MS (m/e): 542 (MH$^+$); $^1$H NMR (DMSO-d6): δ 9.32 (s, 1H), 8.78 (s, 1H), 8.26 (s, 1H), 8.08 (s, 1H), 7.55-7.53 (m, 3H), 7.46 (d, 1H, J=8.2 Hz), 7.19-7.13 (m, 3H), 7.01 (d, 1H, J=7.7 Hz), 5.27 (app t, 1H, J=6.8 Hz), 4.98 (d, 1H, J=7.3 Hz), 3.20-3.16 (m, 3H), 3.00 (d, 1H, J=17.6 Hz), 2.77 (t, 2H, J=6.2 Hz), 2.52-2.51 (m, 1H), 0.91-0.88 (m, 4H).

2: 5-Methyl-N2-[(3aR,8aS)-2-oxo-3,3a,8,8a-tetrahydro-2H-indeno[1,2-d]oxazol-5-yl]-N4-(2,2,4-trimethyl-3-oxo-benz[1,4]oxazin-6-yl)-2,4-pyrimidinediamine LCMS: purity: 99%; MS (m/e): 487 (MH$^+$); $^1$H NMR (DMSO-d6): δ 9.01 (s, 1H), 8.30 (s, 1H), 8.26 (s, 1H), 7.85 (s, 1H), 7.58 (m, 2H), 7.40-7.38 (m, 2H), 7.01 (d, 1H, J=8.0 Hz), 6.92 (d, 1H, J=8.5 Hz), 5.27 (app t, 1H, J=6.0 and 7.3 Hz), 4.98 (d, 1H, J=7.3 Hz), 3.26 (dd, 1H, J=6.0 and 7.3 Hz), 3.19 (s, 3H), 3.00 (d, 1H, J=7.3 Hz), 2.13 (s, 3H), 1.40 (s, 6H).

3: N4-(2,2-Dimethyl-3-oxo-4H-benz[1,4]oxazin-6-yl)-5-methyl-N2-[(3aR,8aS)-2-oxo-3,3a,8,8a-tetrahydro-2H-indeno[1,2-d]oxazol-5-yl]-2,4-pyrimidinediamine LCMS: purity: 97%; MS (m/e): 474 (MH$^+$); $^1$H NMR (DMSO-d6): δ 11.24 (s, 1H), 10.37 (s, 1H), 9.81 (s, 1H), 8.30 (s, 1H), 7.93 (s, 1H), 7.43 (d, 1H, J=8.2 Hz), 7.32 (app d, 2H, J=7.9 Hz), 7.17 (d, 1H, J=7.9 Hz), 5.30 (app t, 1H, J=6.0 and 7.3 Hz), 5.00 (d, 1H, J=7.3 Hz), 3.28 (dd, 1H, J=6.4 and 17.3 Hz), 3.00 (d, 1H, J=17.3 Hz), 2.13 (s, 3H), 1.40 (s, 6H).

4: 5-Methyl-N4-(4-methyl-3-oxo-2H-benz[1,4]thiazin-6-yl)-N2-[(3aR,8aS)-2-oxo-3,3a,8,8a-tetrahydro-2H-indeno[1,2-d]oxazol-5-yl]-2,4-pyrimidinediamine LCMS: purity: 97%; MS (m/e): 475 (MH$^+$); $^1$H NMR (DMSO-d6): δ 10.35 (s, 1H), 9.70 (s, 1H), 8.28 (s, 1H), 7.91 (s, 1H), 7.46 (s, 1H), 7.44 (d, 1H, J=8.2 Hz), 7.32-7.26 (m, 2H), 7.15 (d, 1H, J=8.5 Hz), 5.29 (app t, 1H, J=6.0 and 7.3 Hz), 4.98 (d, 1H, J=7.3 Hz), 3.53 (s, 2H), 3.28 (dd, 1H, J=6.4 and 17.3 Hz), 3.08 (s, 3H), 3.00 (d, 1H, J=17.3 Hz), 2.16 (s, 3H).

5: 5-Methyl-N2-[(3aR,8aS)-2-oxo-3,3a,8,8a-tetrahydro-2H-indeno[1,2-d]oxazol-5-yl]-N4-(2,2,4-trimethyl-3-oxo-5-pyrido[1,4]oxazin-6-yl)-2,4-pyrimidinediamine LCMS: purity: 97%; MS (m/e): 488 (MH$^+$); $^1$H NMR (DMSO-d6): δ 9.15 (s, 1H), 9.30 (s, 2H), 7.94 (s, 1H), 7.83 (d, 1H, J=8.5 Hz), 7.69 (s, 1H), 7.53 (d, 1H, J=8.5 Hz), 7.38 (d, 1H, J=8.5 Hz), 7.11 (d, 1H, J=8.5 Hz), 5.28 (app t, 1H, J=6.2), 5.01 (d, 1H, J=7.3 Hz), 3.35 (s, 3H), 3.23 (dd, 1H, J=6.4 and 17.3 Hz), 2.99 (d, 1H, J=17.3 Hz), 2.13 (s, 3H), 1.43 (s, 6H).

6: 5-Methyl-N4-(4-propyl-3-oxo-2H-benz[1,4]oxazin-6-yl)-N2-[(3aR,8aS)-2-oxo-3,3a,8,8a-tetrahydro-2H-indeno[1,2-d]oxazol-5-yl]-2,4-pyrimidinediamine LCMS: purity: 99%; MS (m/e): 487 (MH$^+$); $^1$H NMR (DMSO-d6): δ 9.04 (s, 1H), 8.36 (s, 1H), 8.29 (s, 1H), 7.85 (s, 1H), 7.57 (s, 1H), 7.51 (d, 1H, J=8.8 Hz), 7.41 (d, 1H, J=8.8 Hz), 7.36 (d, 1H, J=8.8 Hz), 7.35 (s, 1H), 7.05 (d, 1H, J=8.8 Hz), 6.96 (d, 1H, J=8.8 Hz), 5.26 (app t, 1H, J=6.4 Hz), 4.97 (d, 1H, J=7.3 Hz), 4.60 (s, 2H), 3.75-3.62 (m, 2H), 3.24 (dd, 1H, J=6.4 and 17.3 Hz), 3.29 (d, 1H, J=17.3 Hz), 2.10 (s, 3H), 1.51 (hex, 2H, J=7.3 Hz), 0.80 (t, 3H, J=7.3 Hz).

7: 5-Methyl-N2-[(3aR,8aS)-2-oxo-3,3a,8,8a-tetrahydro-2H-indeno[1,2-d]oxazol-5-yl]-N4-(2,2,4-trimethyl-3-oxo-benz[1,4]thiazin-6-yl)-2,4-pyrimidinediamine LCMS: purity: 97%; MS (m/e): 503 (MH$^+$); $^1$H NMR (DMSO-d6): δ 9.11 (s, 1H), 8.41 (s, 1H), 8.30 (s, 1H), 7.90 (s, 1H), 7.64-7.53 (m, 4H), 7.28 (d, 1H, J=8.5 Hz), 7.04 (d, 1H, J=8.5 Hz), 5.27 (app t, 1H, J=7.3 Hz and 6.4H), 4.97 (d, 1H, J=7.3 Hz), 3.26-3.22 (m, 4H), 3.02 (d, 1H, J=17.3 Hz), 2.11 (s, 3H), 1.33 (s, 6H).

8: 5-Chloro-N4-[4-[[N-(cyclopropylsulfonyl)amino]methyl]phenyl]-N2-[(3aR,8aS)-2-oxo-3,3a,8,8a-tetrahydro-2H-indeno[1,2-d]oxazol-5-yl]-2,4-pyrimidinediamine LCMS: purity: 94%; MS (m/e): 528 (MH$^+$); $^1$H NMR (DMSO-d6): δ 9.58 (s, 1H), 9.08 (s, 1H), 8.30 (s, 1H), 8.15 (s, 1H), 7.65-7.58 (m, 3H), 7.51 (s, 1H), 7.45 (d, 1H, J=8.2 Hz). 7.32 (d, 2H, J=8.5 Hz), 7.13 (d, 1H, J=8.2 Hz), 5.31 (app t, 1H, J=6.0 and 7.3 Hz), 5.02 (d, 1H, J=7.3 Hz), 4.17 (d, 2H, J=6.2 Hz), 3.26 (dd, 1H, J=6.0 and 17.3 Hz), 3.02 (d, 1H, J=17.3 Hz), 2.45 (m, 1H), 0.90-0.86 (m, 4H).

9: 5-Methyl-N2-[(3aS,8aR)-2-oxo-3,3a,8,8a-tetrahydro-2H-indeno[1,2-d]oxazol-5-yl]-N4-(2,2,4-trimethyl-3-oxo-benz[1,4]oxazin-6-yl)-2,4-pyrimidinediamine LCMS: purity: 98%; MS (m/e): 487 (MH$^+$); $^1$H NMR (DMSO-d6): 810.42 (s, 1H), 9.75 (s, 1H), 8.28 (s, 1H), 7.87 (s, 1H), 7.41 (d, 1H, J=8.2 Hz), 7.25 (s, 1H), 7.19-7.17 (m, 2H), 7.07 (d, 1H, J=8.2 Hz), 6.99 (d, 1H, J=8.5 Hz), 5.28 (app t, 1H, J=6.4 and 7.0 Hz), 4.98 (d, 1H, J=7.3 Hz), 3.24 (dd, 1H, J=6.4 and 17.0 Hz), 3.06 (s, 3H), 2.99 (d, 1H, J=17.0 Hz), 2.14 (s, 3H), 1.40 (s, 6H).

10: 5-Chloro-N2-[(3aS,8aR)-2-oxo-3,3a,8,8a-tetrahydro-2H-indeno[1,2-d]oxazol-5-yl]-N4-(2,2,4-trimethyl-3-oxo-benz[1,4]oxazin-6-yl)-2,4-pyrimidinediamine LCMS: purity: 98%; MS (m/e): 507 (MH$^+$); $^1$H NMR (DMSO-d6): δ 9.49 (s, 1H), 9.01 (s, 1H), 8.28 (s, 1H), 8.13 (s, 1H), 7.50 (d, 1H, J=8.2 Hz), 7.45 (s, 1H), 7.33 (s, 1H), 7.32 (d, 1H, J=8.2 Hz), 7.02 (d, 1H, J=8.5 Hz), 6.95 (d, 1H, J=8.2 Hz), 5.26 (app t, 1H, J=6.7), 4.96 (d, 1H, J=6.7 Hz), 3.24 (dd, 1H, J=6.4 and 17.5 Hz), 3.12 (s, 3H), 3.00 (d, 1H, J=17.5 Hz), 1.40 (s, 6H).

11: N4-(2,2-Dimethyl-4-ethyl-3-oxo-benz[1,4]oxazin-6-yl)-5-methyl-N2-[(3aS,8aR)-2-oxo-3,3a,8,8a-tetrahydro-2H-indeno[1,2-d]oxazol-5-yl]-2,4-pyrimidinediamine LCMS: purity: 99%; MS (m/e): 501 (MH$^+$); $^1$H NMR (DMSO-d6): 810.30 (s, 1H), 9.65 (s, 1H), 8.28 (s, 1H), 7.86 (s, 1H), 7.41 (d, 1H, J=8.5 Hz), 7.22 (app d, 3H, J=8.8), 7.08 (d, 1H, J=8.8 Hz), 6.99 (d, 1H, J=8.5 Hz), 5.28 (app t, 1H, J=7.3 Hz), 4.98 (d, 1H, J=7.3 Hz), 3.80-3.64 (m, 2H), 3.25 (dd, 1H, J=6.4 and 17.8 Hz), 3.03 (d, 1H, J=17.8 Hz), 2.15 (s, 3H), 1.39 (s, 6H), 1.01 (t, 3H, J=7.3 Hz).

12: 5-Chloro-N4-(2,2-dimethyl-4-ethyl-3-oxo-benz[1,4]oxazin-6-yl)-N2-[(3aS,8aR)-2-oxo-3,3a,8,8a-tetrahydro-2H-indeno[1,2-d]oxazol-5-yl]-2,4-pyrimidinediamine LCMS: purity: 99%; MS (m/e): 521 (MH$^+$); $^1$H NMR (DMSO-d6): δ 9.72 (s, 1H), 9.25 (s, 1H), 8.29 (s, 1H), 8.18 (s, 1H), 7.47 (d, 1H, J=8.5 Hz), 7.41 (s, 1H), 7.35 (d, 1H, J=8.2 Hz), 7.29 (s, 1H), 7.04 (d, 1H, J=8.2 Hz), 6.96 (d, 1H, J=8.5 Hz), 5.27 (app t, 1H, J=6.7 Hz), 4.96 (d, 1H, J=6.7 Hz), 3.84-3.67 (m, 2H), 3.24 (dd, 1H, J=6.4 and 17.8 Hz), 3.02 (d, 1H, J=17.8 Hz), 1.39 (s, 6H), 1.05 (t, 3H, J=7.3 Hz).

13: N4-(2,2-Dimethyl-3-oxo-4H-benz[1,4]oxazin-6-yl)-5-methyl-N2-[(3aS,8aR)-2-oxo-3,3a,8,8a-tetrahydro-2H-indeno[1,2-d]oxazol-5-yl]-2,4-pyrimidinediamine LCMS: purity: 98%; MS (m/e): 473 (MH$^+$); $^1$H NMR (DMSO-d6): δ 10.73 (s, 1H), 10.24 (s, 1H), 9.67 (s, 1H), 8.28 (s, 1H), 7.83 (s, 1H), 6.44 (d, 1H, J=8.2 Hz), 7.20 (s, 1H), 7.13 (d, 1H, J=8.2 Hz), 7.07 (d, 1H, J=8.2 Hz), 6.95-6.92 (m, 2H), 5.28 (app t, 1H, J=6.7 and 7.3 Hz), 4.99 (d, 1H, J=7.3 Hz), 3.27 (dd, 1H, J=6.7 and 17.3 Hz), 3.04 (d, 1H, J=17.3 Hz), 2.11 (s, 3H), 1.39 (s, 6H).

14: 5-Chloro-N4-[3-[[(1,1-dimethylethyl)amino]sulfonyl]phenyl]-N2-[(3aS,8aR)-2-oxo-3,3a,8,8a-tetrahydro-2H-indeno[1,2-d]oxazol-5-yl]-2,4-pyrimidinediamine LCMS: purity: 99%; MS (m/e): 530 (MH$^+$); $^1$H NMR (DMSO-d6): δ 9.38 (s, 1H), 9.14 (s, 1H), 8.29 (s, 1H), 8.16 (s, 1H), 8.07-8.05 (m, 2H), 7.54-7.48 (m, 5H), 7.10 (d, 1H, J=7.9 Hz), 5.27 (app t, 1H, J=6.7 Hz), 4.99 (d, 1H, J=7.0 Hz), 3.25 (dd, 1H, J=6.7 and 17.8 Hz), 3.02 (d, 1H, J=17.8 Hz), 1.09 (s, 9H).

15: N4-[4-[[N-(Cyclopropylsulfonyl)amino]methyl]phenyl]-5-methyl-N2-[(3aS,8aR)-2-oxo-3,3a,8,8a-tetrahydro-2H-indeno[1,2-d]oxazol-5-yl]-2,4-pyrimidinediamine LCMS: purity: 96%; MS (m/e): 507 (MH$^+$); $^1$H NMR (DMSO-d6): 810.43 (s, 1H), 9.76 (s, 1H), 8.32 (s, 1H), 7.88 (s, 1H), 7.68 (t, 1H, J=6.1 Hz), 7.51-7.48 (m, 2H), 7.39-7.29 (m, 4H), 7.20 (d, 1H, J=8.5 Hz), 5.30 (app t, 1H, J=6.4 and 7.1 Hz), 5.02 (d, 1H, J=7.1 Hz), 4.19 (d, 2H, J=6.1 Hz), 3.29 (dd, 1H, J=6.4 and 17.3 Hz), 3.08 (d, 1H, J=17.3 Hz), 2.14 (s, 3H).

16: 5-Chloro-N4-[4-[[N-(cyclopropylsulfonyl)amino]methyl]phenyl]-N2-[(3aS,8aR)-2-oxo-3,3a,8,8a-tetrahydro-2H-indeno[1,2-d]oxazol-5-yl]-2,4-pyrimidinediamine LCMS: purity: 97%; MS (m/e): 528 (MH$^+$); $^1$H NMR (DMSO-d6): δ 9.80 (s, 1H), 9.31 (s, 1H), 8.31 (s, 1H), 8.19 (s, 1H), 7.65 (t, 1H, J=6.4 Hz), 7.57 (d, 2H, J=8.2 Hz), 7.46-7.38 (m, 2H), 7.34-7.25 (m, 3H), 7.14 (d, 1H, J=8.2 Hz), 5.28 (t, 1H, J=6.4 and 7.0 Hz), 5.01 (d, 1H, J=7.0 Hz), 4.19 (d, 2H, J=6.2 Hz), 3.26 (dd, 1H, J=6.1 and 17.8 Hz), 3.03 (d, 1H, J=17.8 Hz), 2.47-2.46 (m, 1H), 0.89-0.85 (m, 4H).

17: 5-Chloro-N4-[4-[[N-(cyclopropylsulfonyl)amino]methyl]-2-methylphenyl]-N2-[(3aS,8aR)-2-oxo-3,3a,8,8a-tetrahydro-2H-indeno[1,2-d]oxazol-5-yl]-2,4-pyrimidinediamine LCMS: Purity: 96%; MS (m/e): 542 (MH$^+$); $^1$H NMR (DMSO-d6): δ 9.32 (s, 1H), 8.73 (s, 1H), 8.22 (s, 1H), 8.06 (s, 1H), 7.65 (t, 1H, 6.4 Hz), 7.39 (s, 1H), 7.33-7.30 (d, 2H, J=8.2 Hz), 7.24-7.21 (m, 2H), 6.97 (d, 1H, J=8.5 Hz), 5.24 (app t, 1H, J=6.4 and 7.0 Hz), 4.92 (d, 1H, J=6.4 Hz), 4.18 (d, 2H, J=6.4 Hz), 3.19 (dd, 1H, J=6.4 and 18.2 Hz), 2.97 (d, 1H, J=18.2 Hz), 2.53-2.52 (m, 1H), 2.15 (s, 3H), 0.90-0.88 (m, 4H).

18: N4-[4-[[N-(Cyclopropylsulfonyl)amino]methyl]-5-methyl-N2-[(3aS,8aR)-2-oxo-3,3a,8,8a-tetrahydro-2H-indeno[1,2-d]oxazol-5-yl]-2,4-pyrimidinediamine LCMS: Purity: 99%; MS (m/e): 520 (MH$^+$); $^1$H NMR (DMSO-d6): δ 10.32 (s, 1H), 9.72 (s, 1H), 8.25 (s, 1H), 7.84 (s, 1H), 7.69 (t, 1H, 6.4 Hz), 7.28 (s, 3H), 7.21 (d, 1H, J=8.5 Hz), 7.14 (s, 1H), 7.06 (d, 1H, J=8.5 Hz), 5.27 (app t, 1H, J=6.7 and 7.0 Hz), 4.92 (d, 1H, J=6.4 Hz), 4.21 (d, 2H, J=6.4 Hz), 3.22 (dd, 1H, J=6.7 and 17.8 Hz), 3.03 (d, 1H, J=18.2 Hz), 2.53-2.52 (m, 1H), 2.15 (s, 6H), 0.91-0.84 (m, 4H).

19: 5-Chloro-N4-(indan-4-yl]-5-methyl-N2-[(3aS,8aR)-2-oxo-3,3a,8,8a-tetrahydro-2H-indeno[1,2-d]oxazol-5-yl]-2,4-pyrimidinediamine LCMS: Purity: 94%; MS (m/e): 434 (MH$^+$); $^1$H NMR (DMSO-d6): δ 9.31 (s, 1H), 8.64 (s, 1H), 8.20 (s, 1H), 8.06 (s, 1H), 7.43-7.41 (m, 2H), 7.25-7.12 (m, 3H), 6.93 (d, 1H, J=8.5 Hz), 5.25 (app t, 1H, J=6.4 and 7.0 Hz), 4.93 (d, 1H, J=6.4 Hz), 3.21 (dd, 1H, J=6.4 and 17.6 Hz), 2.97 (d, 1H, J=17.6 Hz), 2.88 (t, 2H, J=7.3 Hz), 2.74-2.67 (m, 2H), 1.91 (q, 2H, J=7.3 Hz).

20: N4-(Indan-4-yl)-5-methyl-N2-[(3aS,8aR)-2-oxo-3,3a,8,8a-tetrahydro-2H-indeno[1,2-d]oxazol-5-yl]-2,4-pyrimidinediamine LCMS: Purity: 93%; MS (m/e): 414 (MH$^+$); $^1$H NMR (DMSO-d6): δ 8.93 (s, 1H), 8.20 (s, 1H), 8.02 (s, 1H), 7.81 (s, 1H0, 7.52 (s, 1H), 7.49 (d, 1H, J=8.2 Hz), 7.26 (d, 1H=7.6 Hz), 7.14 (t, 1H, J=7.6 Hz), 7.08 (app d, 1H, J=8.5 Hz), 6.92 (d, 1H, J=8.2 Hz), 5.25 (app t, 1H, J=6.7 Hz), 4.94 (d, 1H, J=7.3 Hz), 3.21 (dd, 1H, J=6.4 and 17.8 Hz), 2.96 (d, 1H, J=17.8 Hz), 2.88 (t, 2H, J=17.6 Hz), 2.71 (t, 2H, J=7.6 Hz), 2.07 (s, 3H), 1.91 (q, 2H, J=7.6 Hz).

21: 5-Chloro-N2-[(3aS,8aR)-2-oxo-3,3a,8,8a-tetrahydro-2H-indeno[1,2-d]oxazol-5-yl]-N4-(5,6,7,8-tetrahydronaphthalen-1-yl)2,4-pyrimidinediamine LCMS: Purity: 98%; MS (m/e): 448 (MH$^+$).

22: 5-Methyl-N2-[(3aS,8aR)-2-oxo-3,3a,8,8a-tetrahydro-2H-indeno[1,2-d]oxazol-5-yl]-N4-(5,6,7,8-tetrahydronaphthalen-1-yl)-2,4-pyrimidinediamine LCMS: Purity: 98%; MS (m/e): 428 (MH$^+$); $^1$H NMR (DMSO-d6): δ 8.87 (s, 1H), 8.18 (s, 1H), 7.91 (s, 1H), 7.77 (s, 1H), 7.46-7.44 (m, 2H), 7.19-7.10 (m, 2H), 6.98 (d, 1H, J=7.3 Hz), 6.88 (d, 1H, J=8.8 Hz), 5.24 (app t, 1H, J=6.4 and 7.0 Hz), 4.92 (d, 1H, J=7.0 Hz), 3.20 (dd, 1H, J=6.4 and 17.3 Hz), 2.95 (d, 1H, J=17.3 Hz), 2.75 (br s, 2H), 2.57-2.54 (m, 2H), 2.06 (s, 3H), 1.64 (br s, 4H).

23: N4-(1,4-Benzodioxan-5-yl)-5-chloro-N2-[(3aS,8aR)-2-oxo-3,3a,8,8a-tetrahydro-2H-indeno[1,2-d]oxazol-5-yl]-2,4-pyrimidinediamine LCMS: Purity: 99%; MS (m/e): 452 (MH$^+$).

24: N4-(1,4-Benzodioxan-5-yl)-5-methyl-N2-[(3aS,8aR)-2-oxo-3,3a,8,8a-tetrahydro-2H-indeno[1,2-d]oxazol-5-yl]-2,4-pyrimidinediamine LCMS: Purity: 95%; MS (m/e): 432 (MH$^+$); $^1$H NMR (DMSO-d6): δ 10.32 (s, 1H), 9.58 (s, 1H), 8.24 (s, 1H), 7.86 (s, 1H), 7.39 (d, 1H, J=8.5 Hz), 7.17 (s, 1H), 7.02 (d, 1H, J=8.2 Hz), 7.01-6.95 (m, 1H), 6.94-6.88 (m, 2H), 5.28 (app t, 1H, J=6.7 and 7.4 Hz), 4.98 (d, 1H, J=7.4 Hz), 4.15-4.09 (m, 4H), 3.26 (dd, 1H, J=6.7 and 18.8 Hz), 3.04 (d, 1H, J=18.8 Hz), 2.12 (s, 3H).

25: 5-Chloro-N4-(2,2-difluoro-1,3-benzodioxol-4-yl)-N2-[(3aS,8aR)-2-oxo-3,3a,8,8a-tetrahydro-2H-indeno[1,2-d]oxazol-5-yl]-2,4-pyrimidinediamine LCMS: Purity: 98%; MS (m/e): 474 (MH$^+$).

26: 5-Fluoro-N2-[(3aR,8aS)-2-oxo-3,3a,8,8a-tetrahydro-2H-indeno[1,2-d]oxazol-5-yl]-N4-[4-(pyridin-2-ylmethoxy)phenyl]-2,4-pyrimidinediamine LCMS: Purity: 99%; MS (m/e): 485 (MH$^+$); $^1$H NMR (DMSO-d6): δ 9.80 (s, 1H), 9.69 (s, 1H), 8.61 (d, 1H, J=5.0 Hz), 8.29 (s, 1H), 8.11 (d, 1H, J=4.4 Hz), 7.91 (t, 1H, J=7.9 Hz), 7.62-7.56 (m, 3H), 7.48-7.40 (m, 3H), 7.13 (d, 1H, J=8.2 Hz), 7.00 (d, 2H, J=9.1 Hz), 5.29 (t, 1H, J=6.7 Hz), 5.21 (s, 2H), 5.00 (d, 1H, J=7.0 Hz), 3.29 (dd, 1H, J=6.7 and 17.6 Hz), 3.05 (d, 1H, J=17.6 Hz).

27: 5-Methyl-N2-[(3aR,8aS)-2-oxo-3,3a,8,8a-tetrahydro-2H-indeno[1,2-d]oxazol-5-yl]-N4-[4-(pyridin-2-ylmethoxy)phenyl]-2,4-pyrimidinediamine LCMS: Purity: 99%; MS (m/e): 481 (MH$^+$); $^1$H NMR (DMSO-d6): δ 10.25 (s, 1H), 9.68 (s, 1H), 8.85 (d, 1H, J=4.5 Hz), 8.28 (s, 1H), 7.86 (dt, 1H, J=1.7 and 9.1 Hz), 7.81 (s, 1H), 7.54 (d, 1H, J=7.9 Hz), 7.43-7.35 (m, 4H), 7.23 (s, 1H), 7.13 (d, 1H, J=7.9 Hz), 7.04 (d, 2H, J=8.8 Hz), 5.31 (t, 1H, J=6.7 and 7.2 Hz), 5.21 (s, 2H), 4.98 (d, 1H, J=7.2 Hz), 3.29 (dd, 1H, J=6.7 and 17.8 Hz), (s, 1H), 3.07 (d, 1H, J=17.8 Hz), 2.13 (s, 3H).

28: 5-Methyl-N2-[(3aS,8aR)-2-oxo-3,3a,8,8a-tetrahydro-2H-indeno[1,2-d]oxazol-5-yl]-N4-[4-(pyridin-2-ylmethoxy)phenyl]-2,4-pyrimidinediamine LCMS: Purity: 99%; MS (m/e): 481 (MH$^+$); $^1$H NMR (DMSO-d6): 810.26 (s, 1H), 9.68 (s, 1H), 8.59 (d, 1H, J=4.9 Hz), 8.28 (s, 1H), 7.87 (dt, 1H, J=1.7 and 9.1 Hz), 7.81 (s, 1H), 7.54 (d, 1H, J=7.9 Hz), 7.43-7.35 (m, 4H), 7.23 (s, 1H), 7.13 (d, 1H, J=7.9 Hz), 7.04 (d, 1H, J=8.8 Hz), 5.31 (app t, 1H, J=6.7 and 7.2 Hz), 5.21 (s, 2H), 4.98 (d, 1H, J=6.7 Hz), 3.29 (dd, 1H, J=6.7 and 17.8 Hz), 3.07 (d, 1H, J=17.8 Hz), 2.13 (s, 3H).

29: 5-Fluoro-N2-[(3aR,8aS)-2-oxo-3,3a,8,8a-tetrahydro-2H-indeno[1,2-d]oxazol-5-yl]-N4-[4-[2-(pyridin-4-yl)ethyl]phenyl]-2,4-pyrimidinediamine LCMS: Purity: 98%; MS (m/e): 483 (MH$^+$); $^1$H NMR (DMSO-d6): δ 9.41 (s, 1H), 9.36 (s, 1H), 8.74 (s, 1H), 8.72 (s, 1H), 8.72 (s, 1H), 8.28 (s, 1H), 8.09 (d, 1H, J=3.7 Hz), 7.82 (s, 1H), 7.81 (s, 1H), 7.68 (d, 2H, J=7.9 Hz), 7.6 1 (s, 1H), 7.50 (d, 1H, J=8.2 Hz), 7.18 (d, 2H, J=8.8 Hz), 5.30 (t, 1H, J=6.7 and 7.0 Hz), 5.02 (d, 1H, J=7.0 Hz), 3.28 (dd, 1H, J=6.7 and 17.5 Hz), 3.15 (t, 2H, J=7.3 Hz), 3.10 (d, 1H, J=17.5 Hz), 3.01 (dd, 2H, J=7.3 and 16.2 Hz).

30: 5-Fluoro-N2-[(3aS,8aR)-2-oxo-3,3a,8,8a-tetrahydro-2H-indeno[1,2-d]oxazol-5-yl]-N4-[4-(pyridin-2-ylmethoxy)phenyl]-2,4-pyrimidinediamine LCMS: Purity: 99%; MS (m/e): 485 (MH$^+$); $^1$H NMR (DMSO-d6): δ 9.74 (s, 1H), 9.63 (s, 1H), 8.62 (d, 1H, J=4.7 Hz), 8.29 (s, 1H), 8.11 (d, 1H, J=4.7 Hz), 7.91 (t, 1H, J=7.9 Hz), 7.63-7.56 (m, 3H), 7.49-7.39 (m, 3H), 7.13 (d, 1H, J=8.5 Hz), 7.00 (d, 2H, J=8.8 Hz), 5.29 (app t, 1H, J=6.4 and 7.0 Hz), 5.21 (s, 2H), 5.00 (d, 1H, J=7.0 Hz), 3.29 (dd, 1H, J=6.7 and 17.8 Hz), 3.05 (d, 1H, J=17.8 Hz).

31: 5-Methyl-N2-[(3aR,8aS)-2-oxo-3,3a,8,8a-tetrahydro-2H-indeno[1,2-d]oxazol-5-yl]-N4-[4-(pyridin-3-ylmethoxy)phenyl]-2,4-pyrimidinediamine LCMS: Purity: 99%; MS (m/e): 481 (MH$^+$); $^1$H NMR (DMSO-d6): δ 10.35 (s, 1H), 9.69 (s, 1H), 8.79 (s, 1H), 8.65 (s, 1H), 8.28 (s, 1H), 8.12-8.10 (m, 1H), 7.83 (s, 1H), 7.66-7.63 (m, 1H), 7.46-7.37 (m, 3H), 7.25 (s, 1H), 7.15-7.13 (m, 1H), 7.07-7.04 (m, 2H), 5.30 (m, 1H), 5.23 (s, 2H), 4.98 (s, 1H), 3.30 (d, 1H, J=17.3 Hz), 3.08 (d, 1H, J=17.3 Hz), 2.13 (s, 3H), (s, 2H), 4.98 (d, 1H, J=7.2 Hz), 3.29 (dd, 1H, J=6.7 and 17.8 Hz), (s, 1H), 3.07 (d, 1H, J=17.8 Hz), 2.13 (s, 3H).

32: 5-Methyl-N2-[(3aS,8aR)-2-oxo-3,3a,8,8a-tetrahydro-2H-indeno[1,2-d]oxazol-5-yl]-N4-[4-(pyridin-3-ylmethoxy)phenyl]-2,4-pyrimidinediamine LCMS: Purity: 99%; MS (m/e): 481 (MH+); $^1$H NMR (DMSO-d6): δ 10.23 (s, 1H), 9.66 (s, 1H), 8.74 (s, 1H), 8.61 (d, 1H, J=4.7 Hz), 8.28 (s, 1H), 8.00 (d, 1H, J=7.9 Hz), 7.81 (s, 1H), 7.55 (d, 1H, J=1.7 and 8.2 Hz), 7.43 (d, 2H, J=8.5 Hz), 7.35 (d, 1H, J=7.9 Hz), 7.25 (s, 1H), 7.14 (d, 1H, J=8.2 Hz), 7.05 (d, 2H, J=8.5 Hz), 5.30 (app t, 1H, J=6.4 and 7.3 Hz), 5.20 (s, 2H), 4.99 (d, 1H, J=7.3 Hz), 3.31 (dd, 1H, J=6.4 and 17.3 Hz), 3.07 (d, 1H, J=17.3 Hz), 2.13 (s, 3H).

33: 5-Fluoro-N2-[(3aS,8aR)-2-oxo-3,3a,8,8a-tetrahydro-2H-indeno[1,2-d]oxazol-5-yl]-N4-[4-[2-(pyridin-4-yl)ethyl]phenyl]-2,4-pyrimidinediamine LCMS: Purity: 99%; MS (m/e): 483 (MH+); $^1$H NMR (DMSO-d6): δ 9.42 (s, 1H), 9.37 (s, 1H), 8.74 (s, 1H), 8.72 (s, 1H), 8.28 (s, 1H), 8.09 (d, 1H, J=3.8 Hz), 7.82 (s, 1H), 7.81 (s, 1H), 7.68 (d, 2H, J=8.5 Hz), 7.61 (s, 1H), 7.50 (d, 1H, J=8.5 Hz), 7.18 (d, 2H, J=8.5 Hz), 7.11 (d, 1H, J=8.2 Hz), 5.30 (app t, 1H, J=6.4 and 7.3 Hz), 5.02 (d, 1H, J=7.0 Hz), 3.28 (dd, 1H, J=6.4 and 17.8 Hz), 3.15 (t, 2H, J=7.3 Hz), 3.10 (d, 1H, J=17.8 Hz), 2.99 (dd, 2H, J=7.3 and 16.2 Hz).

34: 5-Chloro-N4-(indan-4-yl)-5-methyl-N2-[(3aR,8aS)-2-oxo-3,3a,8,8a-tetrahydro-2H-indeno[1,2-d]oxazol-5-yl]-2,4-pyrimidinediamine LCMS: Purity: 97%; MS (m/e): 434 (MH+); $^1$H NMR (DMSO-d6): δ 9.36 (s, 1H), 8.71 (s, 1H), 8.20 (s, 1H), 8.08 (s, 1H), 7.43-7.41 (m, 2H), 7.25-7.12 (m, 3H), 6.93 (d, 1H, J=9.1 Hz), 5.25 (app t, 1H, J=6.4 and 7.0 Hz), 4.94 (d, 1H, J=7.0 Hz), 3.21 (dd, 1H, J=6.4 and 17.8 Hz), 2.97 (d, 1H, J=17.8 Hz), 2.88 (t, 2H, J=7.3 Hz), 2.74-2.70 (m, 2H), 1.91 (q, 2H, J=7.0 Hz).

35: N4-(Indan-4-yl)-5-methyl-N2-[(3aR,8aS)-2-oxo-3,3a,8,8a-tetrahydro-2H-indeno[1,2-d]oxazol-5-yl]-2,4-pyrimidinediamine LCMS: Purity: 99%; MS (m/e): 414 (MH+); $^1$H NMR (DMSO-d6): δ 10.27 (s, 1H), 9.69 (s, 1H), 8.22 (s, 1H), (s, 1H), 7.84 (s, 1H), 7.52 (s, 1H), 7.49 (d, 1H, J=8.2 Hz), 7.26 (d, 1H=7.6 Hz), 7.14 (t, 1H, J=7.6 Hz), 7.08 (app d, 1H, J=8.5 Hz), 6.92 (d, 1H, J=8.2 Hz), 5.25 (app t, 1H, J=6.7 Hz), 4.94 (d, 1H, J=7.3 Hz), 3.21 (dd, 1H, J=6.4 and 17.8 Hz), 2.96 (d, 1H, J=17.8 Hz), 2.88 (t, 2H, J=17.6 Hz), 2.71 (t, 2H, J=7.6 Hz), 2.07 (s, 3H), 1.91 (q, 2H, J=7.6 Hz).

36: 5-Chloro-N2-[(3aR,8aS)-2-oxo-3,3a,8,8a-tetrahydro-2H-indeno[1,2-d]oxazol-5-yl]-N4-(5,6,7,8-tetrahydronaphthalen-1-yl)2,4-pyrimidinediamine LCMS: Purity: 99%; MS (m/e): 448 (MH+); $^1$H NMR (DMSO-d6): δ 10.27 (s, 1H), 9.69 (s, 1H), 8.22 (s, 1H), (s, 1H), 7.84 (s, 1H), 7.52 (s, 1H), 7.49 (d, 1H, J=8.2 Hz), 7.26 (d, 1H=7.6 Hz), 7.14 (t, 1H, J=7.6 Hz), 7.08 (app d, 1H, J=8.5 Hz), 6.92 (d, 1H, J=8.2 Hz), 5.25 (app t, 1H, J=6.7 Hz), 4.94 (d, 1H, J=7.3 Hz), 3.21 (dd, 1H, J=6.4 and 17.8 Hz), 2.96 (d, 1H, J=17.8 Hz), 2.88 (t, 2H, J=17.6 Hz), 2.71 (t, 2H, J=7.6 Hz), 2.07 (s, 3H), 1.91 (q, 2H, J=7.6 Hz).

37: 5-Methyl-N2-[(3aR,8aS)-2-oxo-3,3a,8,8a-tetrahydro-2H-indeno[1,2-d]oxazol-5-yl]-N4-(5,6,7,8-tetrahydronaphthalen-1-yl)-2,4-pyrimidinediamine LCMS: Purity: 99%; MS (m/e): 428 (MH+); $^1$H NMR (DMSO-d6): δ 10.28 (s, 1H), 9.57 (s, 1H), 8.21 (s, 1H), 7.83 (s, 1H), 7.29-7.23 (m, 2H), 7.19-7.10 (m, 2H), 6.98 (d, 1H, J=7.3 Hz), 6.88 (d, 1H, J=8.8 Hz), 5.24 (app t, 1H, J=6.4 and 7.0 Hz), 4.92 (d, 1H, J=7.0 Hz), 3.20 (dd, 1H, J=6.4 and 17.3 Hz), 2.95 (d, 1H, J=17.3 Hz), 2.75 (br s, 2H), 2.57-2.54 (m, 2H), 2.06 (s, 3H), 1.64 (br s, 4H).

38: 5-Methyl-N2-[(4aR,9aS)-3-oxo-2,3,4,4a,9a-hexahydroindeno[2,1-b][1,4]oxazin-6-yl]-N4-(2,2,4-trimethyl-3-oxo-benz[1,4]oxazin-6-yl)-2,4-pyrimidinediamine LCMS: Purity: 98%; MS (m/e): 501 (MH+); $^1$H NMR (DMSO-d6): δ 10.07 (s, 1H), 9.47 (s, 1H), 8.81 (d, 1H, J=3.8 Hz), 7.83 (s, 1H), 7.37 (d, 1H, J=8.5 Hz), 7.31 (d, 1H, J=1.8 Hz), 7.25 (s, 1H), 7.20 (dd, 1H, J=1.8 and 8.8 Hz), 7.03 (d, 1H, J=8.8 Hz), 6.92 (d, 1H, J=8.5 Hz), 4.62 (app t, 1H, J=4.4 Hz), 4.46 (t, 1H, J=4.4 Hz), 3.95 (AB qt, 2H, J=16.2 Hz), 3.09-3.04 (m, 4H), 2.74 (d, 1H, J=16.4 Hz), 2.13 (s, 3H), 1.39 (s, 6H).

39: N4-[4-[[N-(Cyclopropylsulfonyl)amino]methyl]phenyl]-5-methyl-N2-[(4aR,9aS)-3-oxo-2,3,4,4a,9a-hexahydroindeno[2,1-b][1,4]oxazin-6-yl]-2,4-pyrimidinediamine LCMS: Purity: 98%; MS (m/e): 521 (MH+); $^1$H NMR (DMSO-d6): δ 9.92 (s, 1H), 9.35 (s, 1H), 8.82 (s, 1H), 7.81 (s, 1H), 7.61 (t, 1H, J=6.4 Hz), 7.56 (d, 2H, J=8.5 Hz), 7.37 (d, 1H, J=8.5 Hz), 7.30-7.28 (m, 3H), 7.17 (d, 1H, J=8.5 Hz), 4.66 (app t, 1H, J=3.8 Hz), 4.48 (t, 1H, J=3.8 Hz), 4.16 (d, 2H, J=6.4 Hz), 3.92 (AB qt, 2H, J=16.2 Hz), 3.13 (dd, 1H, J=3.8 and 16.9 Hz), 2.84 (d, 1H, J=16.9 Hz), 2.44-2.41 (m, 1H), 2.13 (s, 3H0, 0.88-0.84 (m, 4H).

40: 5-Chloro-N4-[4-[[N-(cyclopropylsulfonyl)amino]methyl]phenyl]-N2-[(4aR,9aS)-3-oxo-2,3,4,4a,9a-hexahydroindeno[2,1-b][1,4]oxazin-6-yl]-2,4-pyrimidinediamine LCMS: Purity: 99%; MS (m/e): 542 (MH+); $^1$H NMR (DMSO-d6): δ 9.26 (s, 1H), 8.76 (d, 1H, J=3.5 Hz), 8.74 (s, 1H), 8.09 (s, 1H), 7.67 (d, 2H, J=8.2 Hz), 7.58 (t, 1H, J=6.2 Hz), 7.47 (d, 2H, J=8.5 Hz), 7.26 (d, 2H, J=8.2 Hz), 7.08 (d, 1H, J=8.2 Hz), 4.62 (app t, 1H, J=4.5 Hz), 4.44 (t, 1H, J=4.5 Hz), 4.15 (d, 2H, J=6.2 Hz), 3.91 (AB qt, 2H, J=16.4 Hz), 3.08 (dd, 1H, J=4.5 and 16.4 Hz), 2.79 (d, 1H, J=16.4 Hz), 2.43-2.42 (m, 1H), 0.89-0.85 (m, 4H).

Example 2

Proliferation Assays

Reagents and Buffers
Dimethyl Sulfoxide (DMSO) (Sigma-Aldrich, Cat No. D2650) (Control)
Iscove's DMEM, ATCC Catalog #30-2005
1 M HEPES, Cellgro Catalog #25-060-CI (100 mL)
100 mM Sodium Pyruvate, Cellgro Catalog #25-000-CI (100 mL)
Penicillin/Streptomycin, 10000 U/mL each, Cellgro Catalog #30-002-CI (100 mL)

RPMI 1640 (Cellgro, Cat No. 10-040-CM)
Fetal Bovine Serum (JRH, Cat No. 12106-500M)
Donor Equine Serum, Hyclone Catalog #SH30074.02 (100 mL)
50 μM hydrocortisone solution, Sigma Catalog #H6909-10 ml (10 mL)

Culture Conditions

BaF3 V617F cells are maintained and plated in RPMI with 10% FBS. Plating density for these cells is $1\times10^5$ cells/mL.

Methods

The cells were resuspended in a corresponding medium at a required cell density (see above). 100μ of cell suspension was added to each well of a flat bottom 96 well white plate. The compound was serially diluted in DMSO from 5 mM in 3-fold dilutions, and then diluted 1:250 in the RPMI 1640 medium containing 5% FBS and pen/strep. 100 μL of resulting 2× compound solution was added per well in duplicate and the cells were allowed to proliferate for 72 hours at 37° C.

Proliferation was measured using Cell Titer-Glo. The substrate was thawed and allowed to come to room temperature. After removal of top 100 μL of medium from each well, 100 μL of the premixed Cell Titer-Glo reagent was added to each well. The plates were mixed on an orbital shaker for three minutes to induce lysis and incubated at ambient temperature for an additional five minutes to allow the signal to equilibrate. The Luminescence was read on the Wallac Plate Reader.

The results of the ability of the compounds of the invention to inhibit JAK2 activity, when tested in the above assay, are shown in the following Table 2 wherein the level of activity (i.e., the $IC_{50}$) for each compound is indicated in Table 2. The compound numbers in Table 2 refers to the compounds disclosed herein as being prepared by the methods disclosed herein. In Table 2 the activity is indicated by the following ranges: "A" represents compounds having an $IC_{50}<0.25$ μM; "B" represents compounds having an $IC_{50}\geq0.25$ μM and $<0.5$ μM; "C" represents compounds having an $IC_{50}\geq0.5$ μM and $<1$ μM; "D" represents compounds having activity $\geq1$ μM and $<5$ μM; and "E" represents compounds having activity $\geq5$ μM.

TABLE 2

| Compound # | $IC_{50}$ (μM) |
|---|---|
| 1 | D |
| 2 | A |
| 3 | C |
| 4 | C |
| 5 | A |
| 6 | B |
| 7 | A |
| 8 | A |
| 9 | B |
| 10 | A |
| 11 | B |
| 12 | B |
| 13 | D |
| 14 | C |
| 15 | D |
| 16 | D |
| 17 | D |
| 18 | D |
| 19 | E |
| 20 | A |
| 21 | C |
| 22 | B |
| 23 | D |
| 24 | A |
| 25 | E |
| 26 | D |
| 27 | B |
| 28 | B |
| 29 | B |
| 30 | D |
| 31 | B |
| 32 | B |
| 33 | B |
| 34 | E |
| 35 | A |
| 36 | B |
| 37 | A |
| 38 | B |
| 39 | B |
| 40 | A |

Example 3 pSTAT5 Assay using Primary Human T-Cell or Mouse T-Cell Leukaemia CTLL-2 Cells Stimulated with IL-2

Stimulation of the pre-activated primary human T-cells or mouse CTLL-2 cells with Interleukin-2 (IL-2) signals to JAK-1 and JAK-3 tyrosine kinases to phosphorylate their immediate downstream target, transcription factor STAT5. The effects can then be quantified using FACS.

Human primary T cells are prepared as described in Biological example 2. CTLL-2 cells are grown in RPMI containing 10% FBS and 10% T-STIM with Con A (Becton Dickinson).

Either CTLL-2 or primary T-cells are washed twice with PBS to remove the IL-2 and resuspended in RPMI with 10% FBS medium at $2\times10^6$ cells/mL 40 μL of T cells and 50 μL of 2× compound are added to each well of the 96-well round-bottom plate and mixed. After 1 hour incubation with the compound at 37° C., the cells are stimulated by addition of 10 μL per well of 10× IL2 (400 U/ml) so that the final concentration is 40 U/ml. Cells are incubated further at 37° C. for 15 min. Stimulation is stopped and cells are fixed by addition of 100 μL per well of 3.2% para-formaldehyde and incubation for 10 min at RT. Following a wash, cells are permeabilized by addition of 150 μL per well of ice-cold methanol and incubation at 4° C. for 30 min. Pelleted cells are washed once with 150 μL per well FACS buffer (PBS+2% FCS) and stained with 50 μL per well of anti-phospho-Stat5 AlexaFluor488 1:100 in FACS buffer. Following overnight incubation at RT, the samples are analyzed by FACS after initial wash with FACS buffer.

Example 4 pSTAT5 Assay of Unstimulated Human Erythroleukaemia Cells SET2 and Mouse pre-B Ba/F3 Cells Expressing Human V617F JAK2 Kinase Both cell lines express constitutively active form of JAK2 containing mutation V617F in a pseudokinase domain of the enzyme, leading to constitutive phosphorylation of STAT5 transcription factor in the absence of any stimulation.

40 μL of corresponding cell suspension and 50 μL of 2× compound are mixed together in each well of the 96-well round-bottom plate and incubated for 1 hr at 37° C. The reaction is stopped by addition of 100 μL per well of 3.2% para-formaldehyde for 10 min followed by permeabilization step with 150 ml of ice-cold methanol at 4° C. for 30 min.

After a wash, the cells are stained with 50 μL per well of anti-phospho-Stat5 AlexaFluor488 1:100 in FACS buffer. Following overnight incubation at RT, the samples are analyzed by FACS.

What is claimed is:

1. A compound of formula I:

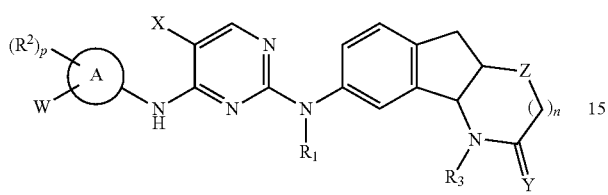

I a tautomer, N-oxide, or salt thereof, wherein:
ring A is aryl or heteroaryl;
n is 0 or 1;
p is 0, 1, 2 or 3 when ring A is monocyclic aryl or heteroaryl or p is 0, 1, 2, 3, 4, or 5 when ring A is bicyclic or tricyclic aryl or heteroaryl;
X is selected from the group consisting of alkyl, substituted alkyl, hydroxy, alkoxy, substituted alkoxy, amino, substituted amino, carboxyl, carboxyl ester, cyano, halo, nitro, alkenyl, substituted alkenyl, alkynyl, and substituted alkynyl;
Y is O or S;
Z is O;
W is hydrogen, —$SO_2N(R^4)R^5$, -alk-$SO_2N(R^4)R^5$, —$N(R^4)SO_2R^5$, or -alk-$N(R^4)SO_2R^5$;
-alk- is selected from the group consisting of straight or branched chain $C_{1-6}$ alkylene group, and straight or branched chain substituted $C_{1-6}$ alkylene group;
$R^1$ is hydrogen or $C_{1-3}$ alkyl;
each $R^2$ independently is selected from the group consisting of alkyl, substituted alkyl, alkoxy, substituted alkoxy, alkenyl, substituted alkenyl, alkynyl, substituted alkynyl, cycloalkenyl, substituted cycloalkenyl, alkynyloxy, amino, substituted amino, aryl, substituted aryl, aryloxy, substituted aryloxy, cyano, cycloalkyl, substituted cycloalkyl, cycloalkoxy, substituted cycloalkoxy, heteroaryl, substituted heteroaryl, heteroaryloxy, substituted heteroaryloxy, heterocyclic, substituted heterocyclic, heterocyclyloxy, substituted heterocyclyloxy, aminocarbonyl, aminocarbonyloxy, carboxyl, carboxyl ester, (carboxyl ester)oxy, nitro, halo, and oxo, wherein if $R^2$ is oxo, then the oxo substituent is attached to a nonaromatic portion of ring A; or
$R^3$ is hydrogen or $C_{1-3}$ alkyl;
$R^4$ is selected from the group consisting of hydrogen, alkyl, substituted alkyl, cycloalkyl, substituted cycloalkyl, heterocyclic, substituted heterocyclic, aryl, substituted aryl, heteroaryl, substituted heteroaryl, acyl and $M^+$, wherein $M^+$ is a counterion selected from the group consisting of $K^+$, $Na^+$, $Li^+$ and $^+N(R^8)_4$, wherein each $R^8$ is independently hydrogen or alkyl, and the nitrogen of —$SO_2N(R^4)R^5$ or —$N(R^4)SO_2R^5$ is $N^-$; and
$R^5$ is selected from the group consisting of hydrogen, alkyl, substituted alkyl, amino, alkylamino, dialkylamino, cycloalkylamino, cycloalkyl, substituted cycloalkyl, heterocyclic, substituted heterocyclic, aryl, substituted aryl, heteroaryl, substituted heteroaryl, and acyl; or
$R^4$ and $R^5$ together with the intervening atom or atoms bound thereto form a heterocyclic or a substituted heterocyclic group.

2. The compound of claim 1, wherein $R^1$ is hydrogen.

3. The compound of claim 2, wherein Y is O and $R^3$ is hydrogen.

4. The compound of claim 3, wherein W is hydrogen.

5. The compound of claim 4, according to formula IIa or IIb:

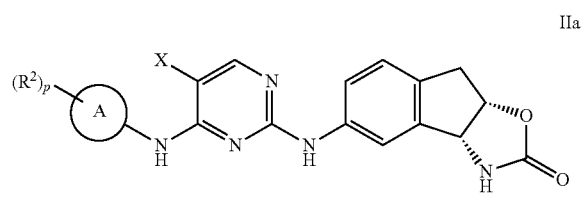

IIa

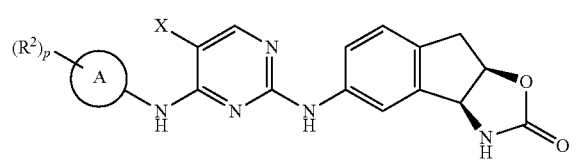

IIb

6. The compound of claim 5, wherein ring A is bicyclic heteroaryl.

7. The compound of claim 6, wherein X is alkyl or halo.

8. The compound of claim 7, wherein X is selected from the group consisting of methyl, chloro, and fluoro.

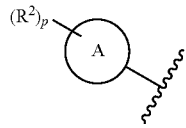

9. The compound of claim, wherein is:

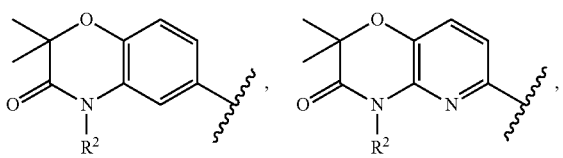

,

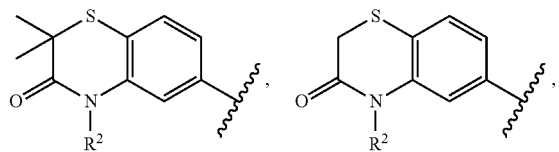

,

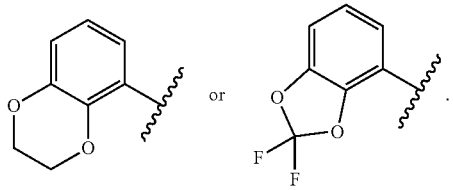

.

10. The compound of claim 5, wherein ring A is monocyclic or bicyclic aryl.

11. The compound of claim 10, wherein X is alkyl or halo.

12. The compound of claim 11, wherein X is selected from the group consisting of methyl, chloro, and fluoro.

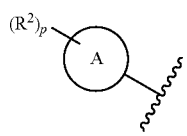

13. The compound of claim 12, wherein is:

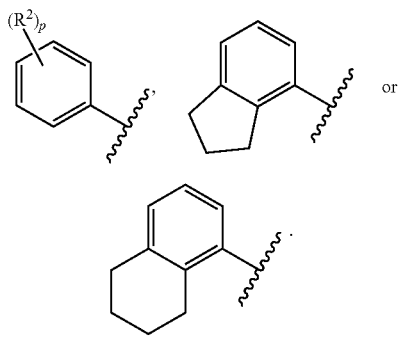

14. The compound of claim 3, according to formula IIa or IIb:

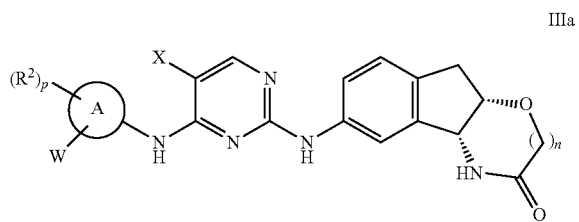

wherein W is not hydrogen.

15. The compound of claim 14, wherein ring A is phenyl.

16. The compound of claim 15, wherein X is alkyl or halo.

17. The compound of claim 16, wherein X is methyl or chloro.

18. The compound of claim 17, wherein is -alk-N(R$^4$)SO$_2$R$^5$.

19. The compound of claim 18, wherein alk is —CH$_2$— or —CH$_2$CH$_2$—.

20. The compound of claim 19, according to formula IVa or IVb:

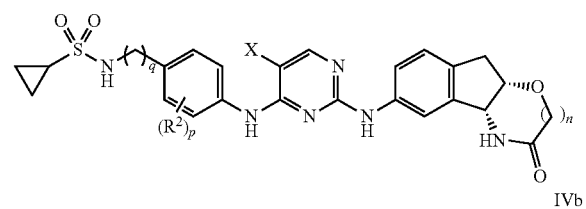

wherein q is 1 or 2.

21. The compound of claim 20, wherein p is 1 and R$^2$ is methyl.

22. The compound of claim 14, wherein W is —SO$_2$N(R$^4$)R$^5$.

23. A compound selected from the group consisting of:
5-Chloro-N4-[4-[2-[N-(cyclopropylsulfonyl)amino]ethyl]phenyl]-N2-[(3 aR,8aS)-2-oxo-3,3a,8,8a-tetrahydro-2H-indeno[1,2-d]oxazol-5-yl]-2,4-pyrimidinediamine;
5-Methyl-N2-[(3aR,8aS)-2-oxo-3,3a,8,8a-tetrahydro-2H-indeno[1,2-d]oxazol-5-yl]-N4-(2,2,4-trimethyl-3-oxo-benz[1,4]oxazin-6-yl)-2,4-pyrimidinediamine;
N4-(2,2-Dimethyl-3-oxo-4H-benz[1,4]oxazin-6-yl)-5-methyl-N2-[(3aR,8aS)-2-oxo-3,3a,8,8a-tetrahydro-2H-indeno[1,2-d]oxazol-5-yl]-2,4-pyrimidinediamine;
5-Methyl-N4-(4-methyl-3-oxo-2H-benz[1,4]thiazin-6-yl)-N2-[(3aR,8aS)-2-oxo-3,3a,8,8a-tetrahydro-2H-indeno[1,2-d]oxazol-5-yl]-2,4-pyrimidinediamine;
5-Methyl-N2-[(3aR,8aS)-2-oxo-3,3a,8,8a-tetrahydro-2H-indeno[1,2-d]oxazol-5-yl]-N4-(2,2,4-trimethyl-3-oxo-5-pyrido[1,4]oxazin-6-yl)-2,4-pyrimidinediamine;
5-Methyl-N4-(4-propyl-3-oxo-2H-benz[1,4]oxazin-6-yl)-N2-[(3aR,8aS)-2-oxo-3,3a,8,8a-tetrahydro-2H-indeno[1,2-d]oxazol-5-yl]-2,4-pyrimidinediamine;
5-Methyl-N2-[(3aR,8aS)-2-oxo-3,3a,8,8a-tetrahydro-2H-indeno[1,2-d]oxazol-5-yl]-N4-(2,2,4-trimethyl-3-oxo-benz[1,4]thiazin-6-yl)-2,4-pyrimidinediamine;
5-Chloro-N4-[4-[[N-(cyclopropylsulfonyl)amino]methyl]phenyl]-N2-[(3aR,8aS)-2-oxo-3,3a,8,8a-tetrahydro-2H-indeno[1,2-d]oxazol-5-yl]-2,4-pyrimidinediamine;
5-Methyl-N2-[(3aS,8aR)-2-oxo-3,3a,8,8a-tetrahydro-2H-indeno[1,2-d]oxazol-5-yl]-N4-(2,2,4-trimethyl-3-oxo-benz[1,4]oxazin-6-yl)-2,4-pyrimidinediamine;
5-Chloro-N2-[(3aS,8aR)-2-oxo-3,3a,8,8a-tetrahydro-2H-indeno[1,2-d]oxazol-5-yl]-N4-(2,2,4-trimethyl-3-oxo-benz[1,4]oxazin-6-yl)-2,4-pyrimidinediamine;
N4-(2,2-Dimethyl-4-ethyl-3-oxo-benz[1,4]oxazin-6-yl)-5-methyl-N2-[(3aS,8aR)-2-oxo-3,3a,8,8a-tetrahydro-2H-indeno[1,2-d]oxazol-5-yl]-2,4-pyrimidinediamine;
5-Chloro-N4-(2,2-dimethyl-4-ethyl-3-oxo-benz[1,4]oxazin-6-yl)-N2-[(3aS,8aR)-2-oxo-3,3a,8,8a-tetrahydro-2H-indeno[1,2-d]oxazol-5-yl]-2,4-pyrimidinediamine;

N4-(2,2-Dimethyl-3-oxo-4H-benz[1,4]oxazin-6-yl)-5-methyl-N2-[(3aS,8aR)-2-oxo-3,3a,8,8a-tetrahydro-2H-indeno[1,2-d]oxazol-5-yl]-2,4-pyrimidinediamine;

5-Chloro-N4-[3-[[(1,1-dimethylethyl)amino]sulfonyl]phenyl]-N2-[(3aS,8aR)-2-oxo-3,3a,8,8a-tetrahydro-2H-indeno[1,2-d]oxazol-5-yl]-2,4-pyrimidinediamine;

N4-[4-[[N-(Cyclopropylsulfonyl)amino]methyl]phenyl]-5-methyl-N2-[(3aS,8aR)-2-oxo-3,3a,8,8a-tetrahydro-2H-indeno[1,2-d]oxazol-5-yl]-2,4-pyrimidinediamine;

5-Chloro-N4-[4-[[N-(cyclopropylsulfonyl)amino]methyl]phenyl]-N2-[(3aS,8aR)-2-oxo-3,3a,8,8a-tetrahydro-2H-indeno[1,2-d]oxazol-5-yl]-2,4-pyrimidinediamine;

5-Chloro-N4-[4-[[N-(cyclopropylsulfonyl)amino]methyl]-2-methylphenyl]-N2-[(3aS,8aR)-2-oxo-3,3a,8,8a-tetrahydro-2H-indeno[1,2-d]oxazol-5-yl]-2,4-pyrimidinediamine;

N4-[4-[[N-(Cyclopropylsulfonyl)amino]methyl]-5-methyl-N2-[(3aS,8aR)-2-oxo-3,3a,8,8a-tetrahydro-2H-indeno[1,2-d]oxazol-5-yl]-2,4-pyrimidinediamine;

5-Chloro-N4-(indan-4-yl)-5-methyl-N2-[(3aS,8aR)-2-oxo-3,3a,8,8a-tetrahydro-2H-indeno[1,2-d]oxazol-5-yl]-2,4-pyrimidinediamine;

N4-(Indan-4-yl)-5-methyl-N2-[(3aS,8aR)-2-oxo-3,3a,8,8a-tetrahydro-2H-indeno[1,2-d]oxazol-5-yl]-2,4-pyrimidinediamine;

5-Chloro-N2-[(3aS,8aR)-2-oxo-3,3a,8,8a-tetrahydro-2H-indeno[1,2-d]oxazol-5-yl]-N4-(5,6,7,8-tetrahydronaphthalen-1-yl)2,4-pyrimidinediamine;

5-Methyl-N2-[(3aS,8aR)-2-oxo-3,3a,8,8a-tetrahydro-2H-indeno[1,2-d]oxazol-5-yl]-N4-(5,6,7,8-tetrahydronaphthalen-1-yl)-2,4-pyrimidinediamine;

N4-(1,4-Benzodioxan-5-yl)-5-chloro-N2-[(3aS,8aR)-2-oxo-3,3a,8,8a-tetrahydro-2H-indeno[1,2-d]oxazol-5-yl]-2,4-pyrimidinediamine;

N4-(1,4-Benzodioxan-5-yl)-5-methyl-N2-[(3aS,8aR)-2-oxo-3,3a,8,8a-tetrahydro-2H-indeno[1,2-d]oxazol-5-yl]-2,4-pyrimidinediamine;

5-Chloro-N4-(2,2-difluoro-1,3-benzodioxol-4-yl)-N2-[(3aS,8aR)-2-oxo-3,3a,8,8a-tetrahydro-2H-indeno[1,2-d]oxazol-5-yl]-2,4-pyrimidinediamine;

5-Fluoro-N2-[(3aR,8aS)-2-oxo-3,3a,8,8a-tetrahydro-2H-indeno[1,2-d]oxazol-5-yl]-N4-[4-(pyridin-2-ylmethoxy)phenyl]-2,4-pyrimidinediamine;

5-Methyl-N2-[(3aR,8aS)-2-oxo-3,3a,8,8a-tetrahydro-2H-indeno[1,2-d]oxazol-5-yl]-N4-[4-(pyridin-2-ylmethoxy)phenyl]-2,4-pyrimidinediamine;

5-Methyl-N2-[(3aS,8aR)-2-oxo-3,3a,8,8a-tetrahydro-2H-indeno[1,2-d]oxazol-5-yl]-N4-[4-(pyridin-2-ylmethoxy)phenyl]-2,4-pyrimidinediamine;

5-Fluoro-N2-[(3aR,8aS)-2-oxo-3,3a,8,8a-tetrahydro-2H-indeno[1,2-d]oxazol-5-yl]-N4-[4-[2-(pyridin-4-yl)ethyl]phenyl]-2,4-pyrimidinediamine;

5-Fluoro-N2-[(3aS,8aR)-2-oxo-3,3a,8,8a-tetrahydro-2H-indeno[1,2-d]oxazol-5-yl]-N4-[4-(pyridin-2-ylmethoxy)phenyl]-2,4-pyrimidinediamine;

5-Methyl-N2-[(3aR,8aS)-2-oxo-3,3a,8,8a-tetrahydro-2H-indeno[1,2-d]oxazol-5-yl]-N4-[4-(pyridin-3-ylmethoxy)phenyl]-2,4-pyrimidinediamine;

5-Methyl-N2-[(3aS,8aR)-2-oxo-3,3a,8,8a-tetrahydro-2H-indeno[1,2-d]oxazol-5-yl]-N4-[4-(pyridin-3-ylmethoxy)phenyl]-2,4-pyrimidinediamine;

5-Fluoro-N2-[(3aS,8aR)-2-oxo-3,3a,8,8a-tetrahydro-2H-indeno[1,2-d]oxazol-5-yl]-N4-[4-[2-(pyridin-4-yl)ethyl]phenyl]-2,4-pyrimidinediamine;

5-Chloro-N4-(indan-4-yl]-5-methyl-N2-[(3aR,8aS)-2-oxo-3,3a,8,8a-tetrahydro-2H-indeno[1,2-d]oxazol-5-yl]-2,4-pyrimidinediamine;

N4-(Indan-4-yl)-5-methyl-N2-[(3aR,8aS)-2-oxo-3,3a,8,8a-tetrahydro-2H-indeno[1,2-d]oxazol-5-yl]-2,4-pyrimidinediamine;

5-Chloro-N2-[(3aR,8aS)-2-oxo-3,3a,8,8a-tetrahydro-2H-indeno[1,2-d]oxazol-5-yl]-N4-(5,6,7,8-tetrahydronaphthalen-1-yl)2,4-pyrimidinediamine;

5-Methyl-N2-[(3aR,8aS)-2-oxo-3,3a,8,8a-tetrahydro-2H-indeno[1,2-d]oxazol-5-yl]-N4-(5,6,7,8-tetrahydronaphthalen-1-yl)-2,4-pyrimidinediamine;

5-Methyl-N2-[(4aR,9aS)-3-oxo-2,3,4,4a,9a-hexahydroindeno[2,1-b][1,4]oxazin-6-yl]-N4-(2,2,4-trimethyl-3-oxo-benz[1,4]oxazin-6-yl)-2,4-pyrimidinediamine;

N4-[4-[[N-(Cyclopropylsulfonyl)amino]methyl]phenyl]-5-methyl-N2-[(4aR,9aS)-3-oxo-2,3,4,4a,9a-hexahydroindeno[2,1-b][1,4]oxazin-6-yl]-2,4-pyrimidinediamine; and 5-Chloro-N4-[4-[[N-(cyclopropylsulfonyl)amino]methyl]phenyl]-N2-[(4aR,9aS)-3-oxo-2,3,4,4a,9a-hexahydroindeno[2,1-b][1,4]oxazin-6-yl]-2,4-pyrimidinediamine.

24. A pharmaceutical formulation comprising the compound as in claim 1, and a pharmaceutically acceptable carrier.

* * * * *